(12) United States Patent
Di Fiore et al.

(10) Patent No.: US 8,747,867 B2
(45) Date of Patent: Jun. 10, 2014

(54) CANCER MARKERS

(75) Inventors: Pier Paolo Di Fiore, Milan (IT); Francesco Nicassio, Milan (IT); Fabrizio Bianchi, Milan (IT)

(73) Assignee: IFOM Fondazione Instituto Firc Di Oncologia Molecolare, Milan (IT)

( * ) Notice: Subject to any disclaimer, the term of this patent is extended or adjusted under 35 U.S.C. 154(b) by 778 days.

(21) Appl. No.: 12/576,812

(22) Filed: Oct. 9, 2009

(65) Prior Publication Data
US 2010/0152058 A1    Jun. 17, 2010

Related U.S. Application Data

(63) Continuation of application No. PCT/GB2007/001343, filed on Apr. 12, 2007, which is a continuation-in-part of application No. 11/664,137, filed as application No. PCT/EP2005/010153 on Sep. 20, 2005, now Pat. No. 7,901,876.

(30) Foreign Application Priority Data

Sep. 30, 2004 (GB) .................................. 0421838.4

(51) Int. Cl.
*A61K 35/12* (2006.01)
(52) U.S. Cl.
USPC ...................................... 424/277.1; 435/7.23
(58) Field of Classification Search
None
See application file for complete search history.

(56) References Cited

U.S. PATENT DOCUMENTS

| | | | |
|---|---|---|---|
| 7,171,311 | B2 | 1/2007 | Dai et al. |
| 2003/0068803 | A1 | 4/2003 | Reed et al. |
| 2005/0272061 | A1 | 12/2005 | Petroziello et al. |
| 2006/0019256 | A1* | 1/2006 | Clarke et al. ............... 435/6 |

FOREIGN PATENT DOCUMENTS

| | | |
|---|---|---|
| WO | 02/103320 | 12/2002 |
| WO | 2003/088910 | 10/2003 |
| WO | 2004/081564 | 9/2004 |
| WO | 2006/034278 A2 | 3/2006 |
| WO | 2006/037462 | 4/2006 |
| WO | 2006/138275 | 12/2006 |

OTHER PUBLICATIONS

Bepler et al, J Clin Onco 22: 1878-1885, 2004.*
Ma et al, PNAS 100:5974-5979 2003.*
Imai et al, J Cancer Res Clin Oncol, 130:320-6, 2004.*
Dehan et al, Lung cancer 56:175-184, Epub Jan. 25, 2007.*
A. Horie et al., generation of a monoclonal antibody against the mouse Sf3b1 (SAP155) gene product for U2 snRNP component of spliceosome, Hybrid Hybridomics, 22(2):117-119 (2003).

Alevizopoulos et al. "A novel function of adenovirus E1A is required to overcome growth arrest by the CDK2 inhibitor p27Kip1" EMBO Journal 17(20):5987-5997 (1998).
Alevizopoulos et al. "Conserved region 2 of adenovirus E1A has a function distinct from pRb binding required to prevent cell cycle arrest by p16INK4a or p27Kip1" Oncogene 19:2067-2074 (2000).
Attwooll et al. "The E2F family: specific functions and overlapping interests" EMBO Journal 23:4709-4716 (2004).
Beer et al. "Gene-expression profiles predict survival of patients with lung adenocarcinoma" Nature Medicine 8 (8):816-824 (2002).
Bepler et al. "Ribonucleotide reductase M1 gene promoter activity, polymorphisms, population frequencies, and clinical relevance" Lung Cancer 47:183-192 (2005).
Bertucci et al. "Gene expression profiles of poor-prognosis primary breast cancer correlate with survival" Human Molecular Genetics 11(8):863-872 (2002).
Bhattacharjee et al. "Classification of human lung carcinomas by mRNA expression profiling reveals distinct adenocarcinoma subclasses" Proc. Natl. Acad. Sci. USA 98(24):13790-13795 (2001).
Bianchi et al. "Survival prediction of stage I lung adenocarcinomas by expression of 10 genes" Journal of Clinical Investigation 117(11):3436-3444 (2007).
Bild et al. "Oncogenic pathway signatures in human cancers as a guide to targeted therapies" Nature 439(19):353-357 (2006).
Blow et al. "Preventing re-replication of chromosomal DNA" Nature Reviews Molecular Cell Biology 6:476-486 (2005).
Bonapace et al. "Np95 is regulated by E1A during mitotic reactivation of terminally differentiated cells and is essential for S phase entry" Journal of Cell Biology 157(6):909-914 (2002).
Buttitta et al. "Int6 expression can predict survival in early-stage non-small cell lung cancer patients" Clinical Cancer Research 11(9):3198-3204 (2005).
Caldas et al. "The molecular outlook" Nature 415(6871):484-485 (2002).
Carter et al. "A signature of chromosomal instability inferred from gene expression profiles predicts clinical outcome in multiple human cancers" Nature Genetics 38(9):1043-1048 (2006).
Chang et al. "Gene expression signature of fibroblast serum response predicts human cancer progression: similarities between tumors and wounds" Plos Biology 2(2):E7 (2004).
Chen et al. "A five-gene signature and clinical outcome in non—small-cell lung cancer" New England Journal of Medicine 356(1):11-20 (2007).
Chen et al. "Global analysis of gene expression in invasion by a lung cancer model" Cancer Research 61:5223-5230 (2001).
Coller et al. "Expression analysis with oligonucleotide microarrays reveals that MYC regulates genes involved in growth, cell cycle, signaling, and adhesion" Proc. Natl. Acad. Sci. USA 97(7):3260-3265 (2000).
Crescenzi et al. "Adenovirus infection induces reentry into the cell cycle of terminally differentiated skeletal muscle cells" Annals New York Academy of Sciences 752:9-18 (1995).
Davidson et al. "An increase in the expression of ribonucleotide reductase large subunit 1 is associated with gemcitabine resistance in non-small cell lung cancer cell lines" Cancer Research 64:3761-3766 (2004).

(Continued)

*Primary Examiner* — Lei Yao
(74) *Attorney, Agent, or Firm* — Morgan, Lewis & Bockius LLP

(57) ABSTRACT

The invention relates to methods of diagnosis and prognosis of cancer, and in particular NSCLC, the methods comprising determining the expression level of one or more genes. In some embodiments the invention relates to prognosis of early stage NSCLC.

20 Claims, 25 Drawing Sheets

(56) References Cited

OTHER PUBLICATIONS de Hoog et al. "RNA and RNA binding proteins participate in early stages of cell spreading through spreading initiation centers" Cell 117:649-662 (2004).
Deleu et al. "Recruitment of TRRAP required for oncogenic transformation by E1A" Oncogene 20:8270-8275 (2001).
Dorsman et al. "The N-terminal region of the adenovirus type 5 E1A proteins can repress expression of cellular genes via two distinct but overlapping domains" Journal of Virology 698(5):2962-2967 (1995).
Duxbury et al. "RNA interference targeting the M2 subunit of ribonucleotide reductase enhances pancreatic adenocarcinoma chemosensitivity to gemcitabine" Oncogene 23:1539-1548 (2004).
Endoh et al. "Prognostic model of pulmonary adenocarcinoma by expression profiling of eight genes as determined by quantitative real-time reverse transcriptase polymerase chain reaction" Journal of Clinical Oncology 22:811-819 (2004).
Fambrough et al. "Diverse signaling pathways activated by growth factor receptors induce broadly overlapping, rather than independent, sets of genes" Cell 97:727-741 (1999).
Ferrari et al. "Epigenetic reprogramming by adenovirus e1a" Science 321:1086-1088 (2008).
Ferreira et al. "The three members of the pocket proteins family share the ability to repress E2F activity through recruitment of a histone deacetylase" Proc. Natl. Acad. Sci. USA 95:10493-10498 (1998).
Fuchs et al. "The p400 complex is an essential E1A transformation target" Cell 106:297-307 (2001).
Fukuse et al. "Expression of proliferating cell nuclear antigen and CD44 variant isoforms in the primary and metastatic sites of nonsmall cell lung carcinoma with intrapulmonary metastases" Cancer 86(7):1174-1181 (1999).
Garber et al. "Diversity of gene expression in adenocarcinoma of the lung" Proc. Natl. Acad. Sci. USA 98 (24):13784-13789 (2001).
Goan et al. "Overexpression of ribonucleotide reductase as a mechanism of resistance to 2,2-difluorodeoxycytidine in the human kb cancer cell line" Cancer Research 59:4204-4207 (1999).
Hallstrom et al. "An E2F1-dependent gene expression program that determines the balance between proliferation and cell death" Cancer Cell 13:11-22 (2008).
Hausen "Oncogenic DNA viruses" Oncogene 20:7820-7823 (2001).
Iyer et al. "The transcriptional program in the response of human fibroblasts to serum" Science .283:83-87 (1999).
Jeon et al. "Clinicopathologic features and prognostic implications of epidermal growth factor receptor (EGFR) gene copy number and protein expression in non-small cell lung cancer" Lung Cancer 54:387-398 (2006).
Jiang et al. "Joint analysis of two microarray gene-expression data sets to select lung adenocarcinoma marker genes" BMC Bioinformatics 5:81 (2004).
Kawai et al. "Estrogen Receptor α and β are Prognostic Factors in Non-Small Cell Lung Cancer" Clinical Cancer Research 11(14):5084-5089 (2005).
Lau et al. "Three-Gene Prognostic Classifier for Early-Stage Non—Small-Cell Lung Cancer" Journal of Clinical Oncology 25(35):5562-5569 (2007).
Lei "The MCM complex: Its role in DNA replication and implications for cancer therapy" Current Cancer Drug Targets 5:365-380 (2005).
Lu et al. "A Gene Expression Signature Predicts Survival of Patients with Stage I Non-Small Cell Lung Cancer" Plos Medicine 3(12): e467 (2006).
Marchetti et al. "Down regulation of high in normal-1 (HIN-1) is a frequent event in stage I non-small cell lung cancer and correlates with poor clinical outcome" Clinical Cancer Research 10:1338-1343 (2004).
Matsuoka et al. "Prognostic factors in patients with pathologic T1-2N1M0 disease in non-small cell carcinoma of the lung" Journal of Thoracic Oncology 2:1098-1102 (2007).
Muller et al. "E2Fs regulate the expression of genes involved in differentiation, development, proliferation, and apoptosis" Genes & Development 15:267-285 (2001).
Nicassio et al. "A cancer-specific transcriptional signature in human neoplasia" Journal of Clinical Investigation 115 (11):3015-3025 (2005).
Nicassio et al. "A cancer-specific transcriptional signature present at high frequency in human neoplasia" CSHL Symposium: Molecular Approaches to Controlling Cancer (2005).
Pajalunga et al. "E2F activates late-G1 events but cannot replace E1A in inducing S phase in terminally differentiated skeletal muscle cells" Oncogene 18:5054-5062 (1999).
Potti et al. "A genomic strategy to refine prognosis in early-stage non—small-cell lung cancer" New England Journal of Medicine 355:570-580 (2006).
Ramaswamy et al. "A molecular signature of metastasis in primary solid tumors" Nature Genetics 33:49-54 (2003).
Ramaswamy et al. "Multiclass cancer diagnosis using tumor gene expression signatures"Proc. Natl. Acad. Sci. USA 98 (26):15149-15154 (2001).
Raponi et al. "Gene expression signatures for predicting prognosis of squamous cell and adenocarcinomas of the lung" Cancer Research 66(15):7466-7472 (2006).
Rhodes et al. "Large-scale meta-analysis of cancer microarray data identifies common transcriptional profiles of neoplastic transformation and progression" Proc. Natl. Acad. Sci. USA 101(25):9309-9314 (2004).
Rosell et al. "Gene expression as a predictive marker of outcome in stage IIB-IIIA-IIIB non-small cell lung cancer after induction gemcitabine-based chemotherapy followed by resectional surgery" Clinical Cancer Research 10:4215s-4219s (2004).
Rosell et al. "Ribonucleotide reductase messenger RNA expression and survival in gemcitabine/cisplatin-treated advanced non-small cell lung cancer patients" Clinical Cancer Research 10:1318-1325 (2004b).
Sandmoller et al. "A novel E1A domain mediates skeletal-muscle-specific enhancer repression independently of pRB and p300 binding" Molecular and Cellular Biology 16(10):5846-5856 (1996).
Seville et al. "Modulation of pRb/E2F functions in the regulation of cell cycle and in cancer" Current Cancer Drug Targets 5:159-170 (2005).
Shelton et al. "Microarray analysis of replicative senescence" Current Biology 9:939-945 (1999).
Shen et al. "Genome-wide examination of myoblast cell cycle withdrawal during differentiation" Developmental Dynamics 226:128-138 (2003).
Shimizu et al. "Differential expressions of cyclin A and the retinoblastoma gene product in histological subtypes of lung cancer cell lines" J Cancer Res Clin Oncol 123:533-538 (1997).
Singhal et al. "Prognostic implications of cell cycle, apoptosis, and angiogenesis biomarkers in non -small cell lung cancer: a review" Clinical Cancer Research 11(11):3974-3986 (2005).
Subramanian et al. "An N-terminal region of adenovirus E1a essential for cell transformation and induction of an epithelial cell growth factor" Oncogene 2(2):105-112 (1988).
Suzuki et al. "Prognostic factors in clinical stage I non—small cell lung cancer" Ann Thorac Surg 67:927-932 (1999).
Tiainen et al. "Expression of E1A in terminally differentiated muscle cells reactivates the cell cycle and suppresses tissue-specifi genes by separable mechanisms" Molecular and Cellular Biology 16(10):5302-5312 (1996).
Tiainen et al. "Terminally differentiated skeletal myotubes are not confined to G0 but can enter G1, upon growth factor stimulation" Cell Growth & Differentiation 7:1039-1050 (1996).
Valladares et al. "Genetic expression profiles and chromosomal alterations in sporadic breast cancer in Mexican women" Cancer Genetics and Cytogentics 170:147-151 (2006).
van de Vijver et al. "A gene-expression signature as a predictor of survival in breast cancer" New England Journal of Medicine 347(25):1999-2009 (2002).
Van't Veer et al. "Gene expression profiling predicts clinical outcome of breast cancer" Nature 415(6871):530-536 (2002).

(56) References Cited

OTHER PUBLICATIONS

Vasseur et al. "Gene expression profiling of tumours derived from rasV12/E1A-transformed mouse embryonic fibroblasts to identify genes required for tumour development" Molecular Cancer 4:4 (2005).

Vernell et al. "Identification of Target Genes of the p16INK4A-pRB-E2F Pathway" Journal of Biological Chemistry 14:46124-46137 (2003).

Volm et al. "Prognostic value of ERBB-1, VEGF, cyclin A, FOS, JUN and MYC in patients with squamous cell lung carcinomas" British Journal of Cancer 77(4):663-669 (1998).

Vooijs et al. "Flp-mediated tissue-specific inactivation of the retinoblastoma tumor suppressor gene in the mouse" Oncogene 17:1-12 (1998).

Wang et al. "hTERT expression is a prognostic factor of survival in patients with stage I non-small cell lung cancer" Clinical Cancer Research 8:2883-2889 (2002).

Wang et al. "Identification of specific adenovirus EIA N-terminal residues critical to the binding of cellular proteins and to the control of cell growth" Journal of Virology 67(1):476-488 (1993).

White et al. "Association between an oncogene and an anti-oncogene; the adeno virus E1A proteins bind to the retinoblastoma gene product" Nature 334:124-129 (1988).

Wigle et al. "Molecular profiling of non-small cell lung cancer and correlation with disease-free survival" Cancer Research 62:3005-3008 (2002).

Yanagisawa et al. "A 25-signal proteomic signature and outcome for patients with resected non—small-cell lung cancer" J Natl Cancer Inst 99:858-867 (2007).

Yanagisawa et al. "Proteomic patterns of tumour subsets in non-small-cell lung cancer" Lancet 362:433-439 (2003).

Yang et al. "CML66, a broadly immunogenic tumor antigen, elicits a humoral immune response associated with remission of chronic myelogenous leukemia" Proc. Natl. Acad. Sci. USA 98(13):7492-7497 (2001).

Zhou et al. "Overexpression of ribonucleotide redactase in transfected human KB cells increases their resistance to hydroxyurea: M2 but not MI is sufficient to increase resistance to hydroxyurea in transfected cells" Cancer Research 55:1328-1333 (1995).

Zuber et al. "A genome-wide survey of RAS transformation targets" Nature Genetics (2000).

\* cited by examiner

| ACC. N° (mouse) | NAME AND DESCRIPTION (mouse) | HUMAN HOMOLOG | ACC. N° (human) | SHORT NAME | E1A C2C12 | SD | MYB C2C12 | SD | E1A MSC | SD | MYB MSC | SD |
|---|---|---|---|---|---|---|---|---|---|---|---|---|
| NM_009830 | CCNE2:cyclin E2 | CCNE2 | NM_004702 | CCNE2 | 24.4 | 1.79 | 7.4 | 0.02 | 84.5 | 4.45 | 11.3 | 1.21 |
| NM_008567 | MIS5/MCM6 minichromosome maintenance deficient 6 | MCM6 | NM_005915 | MCM6 | 16.9 | 2.05 | 11.3 | 0.65 | 70.3 | 1.03 | 46.7 | 0.91 |
| NM_010931 | Np95: nuclear protein 95 | UHRF1 | NM_013282 | NP95 | 19.1 | 0.79 | 22.3 | 1.21 | 54.2 | 3.45 | 47.2 | 2.54 |
| NM_007633 | CCNE1:cyclin E1 | CCNE1 | NM_001238 | CCNE1 | 11.1 | 0.23 | 3.7 | 0.022 | 9.6 | 2.60 | 18.6 | 1.00 |
| NM_008568 | cdc47/MCM7: minichromosome maintenance deficient 7 | MCM7 | NM_005916 | MCM7 | 10.8 | 0.04 | 4.4 | 0.02 | 33.2 | 3.57 | 16.0 | 0.62 |
| NM_008565 | cdc21/MCM4: minichromosome maintenance deficient 4 | MCM4 | NM_005914 | MCM4 | 8.8 | 0.38 | 8.7 | 0.08 | 21.7 | 1.90 | 20.9 | 1.02 |
| NM_178683 | XTP1: HBxAg transactiv. Prot. 1 | XTP1 | NM_018369 | XTP1 | 7.9 | 1.21 | 14.3 | 1.71 | 12.7 | 0.24 | 10.5 | 1.74 |
| NM_016777 | Nasp (somatic): nuclear autoantigenic sperm prot. | NASP(somatic) | NM_152298 | NASPs | 7.3 | 0.63 | 8.9 | 0.18 | 16.9 | 0.66 | 11.0 | 0.21 |
| NM_026115 | Hat1: histidine aminotransferase 1 | HAT1 | NM_003642 | HAT1 | 6.8 | 0. | 12.3. | 10.01 | 15.3 | 0.5 | 27.5 | 0.40 |
| NM_133815 | Lbr: lamin B receptor | LBR | NM_002296 | LBR | 9.4 | 1.50 | 3.6 | 0.58 | 15.8 | 1.01 | 10.5 | 0.77 |
| NM_007891 | E2f1: E2F transcription factor 1 | E2F1 | NM_005225 | E2F1 | 6.7 | 0.50 | 2.2 | 0.05 | 57. | 12.79 | 28.5 | 0.86 |
| NM_177784 | RIKEN cDNA C130068N17 | MGC22679 | NM_144711 | MGC22679 | 10.4 | 1.03 | 1.7 | 0.25 | 4.6 | 0.09 | 2.1 | 0.08 |
| NM_009104 | Rrm2: ribonucleotide reductase | M2 RRM2 | NM_001034 | RRM2 | 3.0 | 0.18 | 2.5 | 0.02 | 19.8 | 0.591 | 6.5 | 0.80 |
| NM_176972 | C330008N13Rik: ubiquitin spec. protease 37 | KIAA1594 | NM_020935 | K1594 | 6.0 | 0.72 | 6.6 | 0.12 | 7.2 | 0.62 | 5.2 | 0.22 |
| XM_130287 | 4930432B04Rik/mKIAA0097 | KIAA0097/ch-TOG | NM_014756 | Ch-TOG | 5.7 | 0.34 | 2.3 | 0.02 | 4.9 | 0.21 | 5.7 | 0.08 |
| XM_358357 | 9030416H16Rik/mouse | KIAA0648 KIAA0648 | NM_015200 | K0648 | 5.3 | 0.38 | 2.4 | 0.17 | 3.4 | 0.36 | 3.7 | 0.45 |
| NM_031179 | SAP150: splicing factor 3b, subunit 1 | SF3B1 | NM_012433 | SF3B1 | 3.5 | 0.41 | 1.0 | 0.02 | 7.4 | 0.58 | 3.7 | 0.22 |
| NM_026149 | 4921S2K09Rik/mouse CML_66 | CML66 | NM_032869 | CML66 | 3.6 | 0.13 | 1.8 | 0.04 | 4.2 | 0.41 | 4.2 | 0.26 |
| NM_171826 | 1110019C08Rik/mouse C3Orf_4 | C3orf4 | NM_019895 | C3orf4 | 2.3 | 0.19 | 1.6 | 0.07 | 4.5 | 0.22 | 4.1 | 0.99 |
| NM_145959 | BC033609 unknown/mouse SKIN | FLJ23790: SKIN | NM_144963 | SKIN | 2.0 | 0.23 | 2.8 | 0.41 | 3.7 | 0.02 | 7.9 | 2.03 |
| NM_011816 | G3BP2: Ras-GTPase-activating protein | G3BP2 | AB014560 | G3BP2 | 3.3 | 0.29 | 1.5 | 0.08 | 3.3 | 0.39 | 2.2 | 0.09 |
| XM_129997 | Taf3: TAF3 RNA polymerase II | TAF3 | NM_291729 | TAF3 | 2.5 | 0.60 | 1.1 | 0.09 | 3.8 | 0.11 | 11.6 | 4.65 |
| NM_019550 | Ptbp2:polypyrimidine tract binding protein 2 | PTBP2 | NM_021190 | PTBP2 | 3.3 | 0.43 | 2.3 | 0.18 | 2.9 | 0.22 | 2.7 | 0.32 |
| NM_181278 | RIKEN cDNA B230219D22 | FLJ37562 | NM_152409 | FLJ37562 | 2.7 | 0.15 | 0.8 | 0.42 | 3.6 | 0.26 | 3.0 | 0.52 |
| NM_019693 | Bat1a:HLA-B-associated transcript 1A | BAT1 | NM_004640 | BAT1 | 2.6 | 0.25 | 2.7 | 0.05 | 3.8 | 0.06 | 5.4 | 0.11 |
| NM_019666 | Syncrip: synaptotagmin binding | NSAP1 | NM_006372 | NSAP1 | 3.7 | 0.18 | 2.4 | 0.05 | 2.2 | 0.05 | 3.1 | 0.13 |
| NM_019553 | DDX21:DEAD box polypeptide | 21 DDX21 | BC004182 | DDX21 | 2.0 | 0.05 | 2.1 | 0.03 | 2.3 | 0.02 | 2.4 | 0.21 |
| NM_019828 | Trpc4ap: transient receptor pot. Cat. channel 4 ass. Prot. | TRPC4AP | BC013144 | TRPC4AP | 2.0 | 0.02 | 0.9 | 0.29 | 3.0 | 0.09 | 1.9 | 0.29 |
| NM_021535 | RIKEN cDNA 2610203K23 | SMU-1 | BC002876 | SMU-1 | 2.0 | 0.03 | 1.4 | 0.01 | 2.3 | 0.05 | 2.7 | 0.10 |

CLASS A

| ACC. Ni | Short Name | YH47 | E2F | Rb rem. | Ratio 24h/36h | TIMING |
|---|---|---|---|---|---|---|
| NM_026115 | HAT1 | 0.07 ± 0.0 | 0.24 ± 0.0 | 0.91 ± 0.2 | 0.54 ± 0.3 | EARLY |
| NM_133815 | LBR | 0.20 ± 0.1 | 0.34 ± 0.1 | 2.06 ± 0.2 | 0.48 ± 0.0 | EARLY |
| NM_178683 | XTP1 | 0.07 ± 0.1 | 0.53 ± 0.1 | 0.43 ± 0.1 | 0.41 ± 0.0 | EARLY |
| NM_007633 | CCNE1 | 0.04 ± 0.0 | 0.69 ± 0.2 | 2.99 ± 0.3 | 1.02 ± 0.6 | EARLY |
| NM_009104 | RRM2 | -0.05 ± 0.0 | 0.82 ± 0.1 | 1.53 ± 0.2 | 0.49 ± 0.0 | EARLY |
| NM_009830 | CCNE2 | 0.03 ± 0.0 | 0.73 ± 0.2 | 1.49 ± 0.2 | 0.56 ± 0.2 | EARLY |
| NM_007891 | E2F1 | 0.03 ± 0.0 | 19.17 ± 8.4 | 1.09 ± 0.1 | 0.67 ± 0.3 | EARLY |

CLASS B

| ACC. Ni | Short Name | YH47 | E2F | Rb rem. | Ratio 24h/36h | TIMING |
|---|---|---|---|---|---|---|
| NM_010931 | NP95 | 0.01 ± 0.0 | 0.17 ± 0.1 | 1.34 ± 0.2 | 0.75 ± 0.3 | EARLY |
| NM_177784 | MGC22679 | 0.18 ± 0.1 | -0.03 ± 0.1 | 2.39 ± 0.2 | 0.68 ± 0.0 | EARLY |
| NM_176972 | K1594 | 0.12 ± 0.7 | 0.02 ± 0.0 | 0.82 ± 0.1 | 0.47 ± 0.1 | EARLY |
| NM_016777 | NASPs | 0.07 ± 0.1 | 0.10 ± 0.1 | 0.90 ± 0.1 | 0.46 ± 0.1 | EARLY |
| NM_008568 | MCM7* | 0.02 ± 0.0 | 0.07 ± 0.0 | 1.16 ± 0.1 | 0.84 ± 0.2 | EARLY |
| NM_008565 | MCM4* | 0.03 ± 0.0 | 0.11 ± 0.0 | 0.73 ± 0.1 | 0.60 ± 0.3 | EARLY |
| NM_008567 | MCM6* | 0.04 ± 0.0 | 0.14 ± 0.0 | 0.64 ± 0.1 | 0.77 ± 0.0 | EARLY |

Fig. 2

| CLASS C | | | | | | |
|---|---|---|---|---|---|---|
| ACC. Ni | Short Name | YH47 | E2F | Rb rem. | Ratio 24h/36h | TIMING |
| NM_171826 | C3orf4 | 0.30 ± 0.1 | 0.08 ± 0.0 | 1.27 ± 0.1 | 0.21 ± 0.1 | LATE |
| NM_011816 | G3BP2 | 0.40 ± 0.1 | 0.05 ± 0.1 | 0.71 ± 0.1 | 0.26 ± 0.0 | LATE |
| XM_120027 | TAF3 | 0.44 ± 0.2 | 0.07 ± 0.0 | 0.98 ± 0.1 | 0.36 ± 0.1 | LATE |
| NM_026140 | CML66 | 0.53 ± 0.0 | 0.06 ± 0.0 | 0.60 ± 0.1 | 0.35 ± 0.0 | LATE |
| XM_358357 | K0648 | 0.60 ± 0.0 | 0.46 ± 0.1 | 2.97 ± 0.5 | 0.27 ± 0.2 | LATE |
| NM_019666 | NSAP1 | 0.60 ± 0.2 | 0.19 ± 0.2 | 2.13 ± 0.2 | 0.02 ± 0.1 | LATE |
| NM_181228 | FLJ37562 | 0.61 ± 0.1 | 0.04 ± 0.3 | 0.75 ± 0.1 | 0.19 ± 0.2 | LATE |
| NM_019493 | BAT1 | 0.62 ± 0.3 | 0.06 ± 0.3 | 0.80 ± 0.2 | 0.33 ± 0.0 | LATE |
| NM_019550 | PTB2 | 0.70 ± 0.1 | 0.15 ± 0.1 | 1.65 ± 0.1 | 0.10 ± 0.2 | LATE |

| CLASS D | | | | | | |
|---|---|---|---|---|---|---|
| ACC. Ni | Short Name | YH47 | E2F | Rb rem. | Ratio 24h/36h | TIMING |
| NM_021535 | SML-1 | 0.44 ± 0.2 | 0.20 ± 0.2 | 0.29 ± 0.1 | 0.38 ± 0.1 | LATE |
| NM_031179 | SF3B1 | 0.47 ± 0.1 | 0.19 ± 0.3 | 0.55 ± 0.1 | 0.07 ± 0.0 | LATE |
| XM_130287 | Ch-TOG | 0.51 ± 0.2 | 0.32 ± 0.1 | 0.30 ± 0.2 | 0.19 ± 0.1 | LATE |
| NM_145959 | SKIN | 0.68 ± 0.4 | 0.13 ± 0.3 | 0.01 ± 0.1 | 0.27 ± 0.2 | LATE |
| NM_019828 | TRPC4AP | 0.81 ± 0.6 | 0.02 ± 0.2 | 0.18 ± 0.1 | 0.36 ± 0.2 | LATE |
| NM_019553 | DDX21 | 1.11 ± 0.3 | 0.20 ± 0.2 | 0.26 ± 0.1 | 0.28 ± 0.2 | LATE |

Fig. 2 Continued

| | Breast | Colon | Kidney | Larynx | Lung | Prost. | Stom. | Uterus | Melan. | Brain |
|---|---|---|---|---|---|---|---|---|---|---|
| SF3B1 %(n) | 23%(13) | 77%(13) | 0%(13) | 6%(18) | 35%(31) | 0%(20) | 12%(26) | 21%(19) | 0%(12) | 7%(15) |
| Ch-TOG %(n) | 21%(19) | 71%(24) | 0%(7) | 44%(9) | 18%(22) | 0%(6) | 50%(12) | 19%(21) | 13%(13) | 32%(19) |
| SKIN %(n) | 21%(67) | 87%(33) | 0%(8) | 71%(17) | 29%(41) | 0%(20) | 29%(23) | 36%(25) | 88%(17) | 13%(16) |
| TRCP4AP %(n) | 56%(16) | 54%(13) | 4%(25) | 4%(23) | 28%(36) | 5%(19) | 37%(30) | 11%(18) | 63%(8) | 0%(13) |
| SMU-1 %(n) | 27%(15) | 31%(13) | 0%(21) | 7%(27) | 13%(31) | 0%(21) | 10%(30) | 12%(17) | 0%(8) | 0%(15) |
| DDX21 %(n) | 88%(9) | 77%(13) | 0%(25) | 52%(21) | 56%(34) | 0%(13) | 55%(29) | 33%(18) | 33%(9) | 0%(15) |

| Symbol | PUBMED ID | N (log2 median) | T (log2 median) | p-value | site | N total | T total |
|---|---|---|---|---|---|---|---|
| SMU-1 | 11742071 | -0,989 | -0,614 | 0,024 | multi-cancer | 90 | 218 |
| SF3B1 | 11742071 | -0,371 | 1,163 | 0,041 | pancreas | 21 | 11 |
| ch-TOG | 11707567 | -0,638 | 0,083 | 0,005 | lung | 17 | 139 |
| ch-TOG | 12058060 | -1,156 | -0,825 | <0,001 | liver | 76 | 104 |
| ch-TOG | 12368205 | -0,678 | 0,277 | <0,001 | salivary gland | 6 | 16 |
| DDX21 | 11158614 | -0,207 | 0,289 | 0,027 | ovary | 4 | 28 |
| DDX21 | 11742071 | -1,023 | 0,33 | 0,032 | brain | 20 | 10 |

| Symbol | PUBMED ID | T (log2 median) | M (log2 median) | p-value | site | T total | M total |
|---|---|---|---|---|---|---|---|
| SF3B1 | 12154061 | -0,066 | 0,138 | 0,001 | prostate | 23 | 9 |
| SF3B1 | 11707567 | -0,52 | -0,213 | 0,021 | lung | 123 | 16 |
| ch-TOG | 11707567 | 0,056 | 0,288 | 0,011 | lung | 123 | 16 |

Fig. 7

| CELL LINE | RNA level | COPIES | chr. 8 | PLOIDY |
|---|---|---|---|---|
| MCF10A | 1.04 ± 0.2 | 4 | 2 | 2 |
| WI38 | 1.22 ± 0.0 | 4 | 2 | 2 |
| HMEC | 2.03 ± 0.2 | 4 | 2 | 2 |
| SK-MEL-28 | 1.56 ± 0.1 | 10-12 | 5 | 2 |
| DLD-1 | 1.89 ± 0.1 | 6 | 3 | 2 |
| SW-480 | 2.47 ± 0.1 | 8 | 4 | 2 |
| TE671 | 2.91 ± 0.2 | 8-10* | 3 | 3-4 |
| COLO 800 | 4.25 ± 0.2 | 6* | 2 | >3 |
| MDA-MB-361 | 4.31 ± 0.2 | 5* | 3 | >3 |
| MCF7 | 4.77 ± 0.4 | >10* $ | 4 | >4 |
| SK-MEL-5 | 4.84 ± 0.1 | 12-14 # | 6 | >5 |
| HT-29 | 9.26 ± 0.9 | 4 # | 2 | >6 |
| SKBR3 | 9.64 ± 0.6 | 8* # $ | 3 | >6 |

CANCER MARKERS

This is a continuation application of International Application No. PCT/GB2007/001343 (filed Apr. 12, 2007) which is a Continuation-In-Part of U.S. application Ser. No. 11/664,137 (filed on May 29, 2007) which is a National Phase Application under 35 U.S.C. 371 of PCT/EP2005/010153 (filed on Sep. 20, 2005) which claims the benefit of United Kingdom Patent Application No. 0421838.4 (Sep. 30, 2004), all of which are hereby incorporated by reference in their entirety.

FIELD OF THE INVENTION

The present invention relates to novel markers for cancer, and the use of these markers in assessment of disease conditions and particularly in prognosis and in therapy.

BACKGROUND TO THE INVENTION

A significant amount of work has been carried out in the art to identify "cancer signatures", which can be used in patient management or which can identify the targets subverted in neoplasia. These efforts are mainly concentrated on unbiased screening of cancer transcriptomes. For example, one approach is to identify genes whose expression is significantly modified in tumours as compared to normal cells, or in tumours of different grades (e.g., Beer, D. G., et al. 2002, *Nature Medicine* Vol. 8, No. 8, 816-824) and to select from these a subset which are associated with survival. A difficulty of this approach is that the resultant signatures often represent the end point of complex upstream interactions, and cannot readily be allocated to particular molecular pathways.

Another approach has been used in Brown P O et al (Chang, H. Y., et al. 2004, *PloS Biol.* 2004 Feb. 2(2): E7). Here, gene expression profiles were obtained from fibroblasts, in response to serum exposure. Genes which formed part of this fibroblast common serum response were found to be regulated in many human tumours. It was proposed that this is due to similarity in the molecular mechanism of cancer progression and wound healing.

Signatures produced in the prior art are often not highly robust, and often fail to provide good results from datasets that have been obtained in different clinical environments and from different patients. Additionally, prior art signatures often include a large number of genes, which increases the cost and difficulty of clinical screening in patients. In a clinical setting the use of small signatures is desirable as analysis is rendered much easier. For instance, smaller numbers of genes are amenable to analysis with readily available technology such as Real Time PCR.

Therefore, there is a continuing need to develop new approaches to identifying cancer signatures, so as to identify new diagnostic, prognostic or therapeutic markers.

SUMMARY OF THE INVENTION

The present inventors have developed an approach which uses well defined molecular tools capable of forcing terminally differentiated cells in culture to re-enter the cell cycle.

The present invention is therefore based in part on a biased method of identifying cancer signatures, in which the examination of the cancer transcriptome is biased towards (or indeed, focused primarily or entirely on) genes which have been shown to be modulated in response to agents which force re-entry of terminally differentiated cells into the cell cycle. This is based on the hypothesis that the molecular tools mimic pathways subverted in naturally occurring tumours and that a limited number of altered signalling pathways lead to the malignant state.

The inventors have found that the signatures obtained by the method, and in particular by focusing on genes modulated in response to E1A, can provide good indicators for the assessment of cancer and cancer progression.

In addition, the genes identified in such a screen can be more readily reverse engineered into signalling pathways, and thus, pathways of particular interest in human cancers can be identified.

The inventors have identified E1A-modulated genes which are strongly associated with human cancers. Thus, one aspect of the invention concerns methods of assessment of cancer which comprise assessing the status of such genes.

One particular class of E1A-modulated genes of interest are genes whose expression is not strongly modulated, e.g., induced, by inactivation of a pocket protein, preferably Rb, and which are significantly modulated (e.g., induced) by an E1A pocket binding mutant, particularly the E1A pocket binding mutant YH47. The mutant is described in Wang H G et al, "Identification of specific adenovirus E1A N-terminal residues critical to the binding of cellular proteins and to the control of cell growth", J Virol. 1993 January; 67(1): 476-88.

The inventors have shown that genes in this class, e.g., DDX21, SF3B1, ch-TOG, SKIN, TRPC4AP and SMU-1, are upregulated in a significant proportion of human cancers (relative to normal tissue), and can also be used as predictors of cancer progression. Moreover, this E1A induced pathway appears to represent a useful therapeutic target. The inhibition of expression of an example of this class of genes, SKIN, is able to dramatically reduce proliferation in cancer cell lines overexpressing SKIN while having no effect on normal cells.

The inventors have also identified other classes of genes which are induced by E1A and which can be used as predictors of cancer progression.

The classes of genes are genes whose expression is
  (a) strongly modulated, e.g., induced, by inactivation of a pocket protein, preferably Rb, not modulated (e.g., induced) by an E1A pocket binding mutant, particularly the E1A pocket binding mutant YH47 and strongly induced by E2F1 overexpression
  (b) strongly modulated, e.g., induced, by inactivation of a pocket protein, preferably Rb, not modulated (e.g., induced) by an E1A pocket binding mutant, particularly the E1A pocket binding mutant YH47 and not (or scarcely) induced by E2F1 overexpression
  (c) strongly modulated, e.g., induced, by inactivation of a pocket protein, preferably Rb, modulated (e.g., induced) by an E1A pocket binding mutant, particularly the E1A pocket binding mutant YH47 and not (or scarcely) induced by E2F1 overexpression.

Examples of genes included in these classes are represented in FIG. 2.

Thus, in one embodiment, the present invention provides a method for the assessment of cancer in a subject, the method comprising:
  providing an assay sample obtained from said subject;
  determining the expression level in the sample of one or more genes from FIG. 2.

Preferably the method involves determining the expression level of a plurality of genes from FIG. 2 (i.e., two or more genes), most preferably 3, 4, 5 or more genes. In some embodiments the method may comprise determining the expression level of 10 or more or 15 or more genes.

In a preferred embodiment, the cancer is breast cancer. In this embodiment, the method may comprise determining the expression level in the sample of at least one (preferably at least two or three) of the ch-TOG, SKIN, and TRPC4AP genes. In respect of breast cancer, the invention may also relate to method for the assessment of cancer in a subject, the method comprising:

providing an assay sample obtained from said subject;
determining the expression level in the sample of one or more genes (preferably 2, 3, 4, 5, 8, 10, 11, 12 or all genes) from table 1.

In another preferred embodiment, the cancer is colon cancer. In this embodiment, the method may comprise determining the expression level in the sample at least one (preferably at least two or three) of SKIN, SMU-1 and ch-TOG.

In another embodiment, the cancer is non-small cell lung carcinoma (NSCLC).

In a further embodiment, the invention provides a method for assessment of NSCLC (non small cell lung cancer) in a subject, and preferably a method for assigning a prognosis to the subject, comprising:

providing an assay sample obtained from said subject;
determining the expression level in said sample of at least one gene from table 2 and/or table 3.

It is preferred that the above methods comprise determining the expression level of at least 2, 3, 4, 5, 8, 10, 11, 12 or more, or all, of the genes in table 2 and/or 3. In some embodiments, in the case of the genes of table 3, the method may comprise determining the expression level of at least 15 or 20 of the genes in that table.

The present inventors have also used an integrated strategy for analysing the cancer transciptome, which integrates meta-analysis of microarray expression data and expression profiling of E1A modulated genes. In doing so, the present inventors have identified further signatures as set out in tables 8, 8a, 8b and 9, associated with NSCLC.

Accordingly, the present invention also relates to a method for assessment of NSCLC in a subject, and preferably a method for assigning a prognosis to the subject, comprising:

providing an assay sample obtained from said subject;
determining the expression level in said sample of at least one gene from table 8, preferably a plurality of genes.

Preferably, the method comprises determining the expression level of a plurality of genes from table 8, i.e., at least 2, 3, 4, 5, 6, 7, 8, 9 or 10 of said genes. In some embodiments the method may comprise determining the expression level of at least 15, 20, 25 or 30 of said genes.

In some embodiments, it may be preferred that the method comprises determining the expression level of at least 2, 3, 4, 5, 6, 7, 8, 9 or 10 genes from table 8a. Preferred genes of table 8a may be or include E2F1, MCM6, SF3B1, RRM2 and/or NUDCD1.

It may alternatively or additionally be preferred that the method comprises determining the expression level of at least 2, 3, 4, 5, 6, 7, 8, 9 or 10 genes from table 8b. Preferred genes of table 8b may be or include HOXB7, SerpinB5, E2F4, and/or HSPG2.

It may be preferred that the method comprises determining the expression level of at least 2, 3, 4, 5, 6, 7, 8, 9 or 10 genes from table 2, 3 or 9.

Other genes which may be used in some embodiments are those marked with the symbol † in table 8. In some embodiments, the genes for use in the method may include any one of these—e.g., the methods may comprise measuring the expression level of any 5, 8, 10 or more of the genes of table 8 including any one (or 2, 3, 4, 5 etc) of the genes marked with the symbol †.

In another aspect, the present invention relates to a kit/apparatus suitable for carrying out any of the above methods.

The present invention provides a kit for use in assessing cancer in a subject, and preferably a method for assigning a prognosis to the subject, based on a sample obtained therefrom, the kit comprising specific binding partners capable of binding to an expression product of:

one or more genes (preferably each of a plurality of genes, more preferably 2, 3, 4, 5, 10, 15 or more genes) from FIG. 2;
one or more genes (preferably each of a plurality of genes, more preferably 2, 3, 4, 5, 8, 10, 11, 12 or more genes) from table 2;
one or more genes (preferably each of a plurality of genes, more preferably 2, 3, 4, 5, 8, 10, 11, 12 or more genes) from table 3;
one or more genes (preferably each of a plurality of genes, more preferably 2, 3, 4, 5, 8, 10, 15, 20 or more genes) from table 8; and/or
one or more genes (preferably each of a plurality of genes, more preferably at least 2, 3, 4, 5, 7, 8 or 9, or all 10 genes) from table 9.

In the case of kits for FISH, the binding partners may be nucleic acids which bind the gene itself, and which are detectably labelled.

The present invention also provides an apparatus comprising a solid support bearing binding partners capable of binding to an expression product of:

one or more genes (preferably each of a plurality of genes, more preferably 2, 3, 4, 5, 10, 15 or more genes) from FIG. 2;
one or more genes (preferably each of a plurality of genes, more preferably 2, 3, 4, 5, 8, 10, 11, 12 or more genes) from table 2;
one or more genes (preferably each of a plurality of genes, more preferably 2, 3, 4, 5, 8, 10, 11, 12 or more genes) from table 3;
one or more genes (preferably each of a plurality of genes, more preferably 2, 3, 4, 5, 8, 10, 15, 20 or more genes) from table 8; and/or
one or more genes (preferably each of a plurality of genes, more preferably at least 2, 3, 4, 5, 7, 8 or 9, or all 10 genes) from table 9.

Preferred features with regards to the methods described above apply equally to the kit/apparatus.

In following the above-described integrated strategy, the present inventors have identified genes which provide a high prognostic power in NSCLC, and in particular which provide a remarkably high prognostic power with a relatively small number of genes.

The inventors have compared the newly-identified signature to the 21 gene signature of table 3 (also described in co-pending application PCT/EP2005/010153). As shown in example 5, unexpectedly, the reduced gene set actually showed an increased prognostic power (sensitivity, accuracy and/or specificity) as compared to the 21-gene set.

Accordingly, in one aspect, the present invention relates to a method for the assessment of NSCLC in a subject, most preferably for assigning a prognosis to a subject having NSCLC, comprising:

providing an assay sample obtained from said subject; and
determining the expression level in said sample of a plurality of genes from table 9 (preferably 5 or more; in some embodiments 6, 7, 8 or 9 or more genes, or all ten genes).

It may be preferred that the genes measured in the method consist of:

no more than 14 (or 13, 12, 11 or 10) genes from table 3, including at least 6 (or 7, 8, 9 or 10) genes from table 9;

optionally other genes (e.g., prognostic genes) not listed in either table 3 or table 9 (in some embodiments, not listed in table 8); and optionally control genes (controls genes being those not associated with assessment of cancer in the method).

The present invention also relates to a method for assigning a prognosis to a subject having NSCLC, the method comprising measuring in a sample taken from said subject the expression level of prognostic genes, wherein said prognostic genes include no more than 14 genes from table 3 and wherein said prognostic genes include at least 6 genes from table 9.

Preferably, the prognostic genes include at least 7, 8 or 9, and more preferably, all ten of the genes from table 9.

It may be preferred that the prognostic genes include no more than 13, 12, 11 or no more than 10 genes from table 3. Where the prognostic genes include no more than 13, 12, 11 or genes from table 3, it may be preferred that at least 8 are from table 9; more preferably this includes 9 or all ten from table 9. Where said prognostic genes comprises no more than 10 genes from table 3, these ten genes may be all ten genes from table 9.

Of course, the method may also comprise measuring genes as controls, wherein in the course of said method no association is made between the expression level of the controls and prognosis.

Moreover, the assignment of a prognosis may take account of other factors and clinical parameters such as tumour size, tumour grading, tumour infiltration, and degree of metastasis of the tumour.

The prognostic genes may optionally include, in addition, other genes which are not listed in either table 3 or 9, in order to further increase prognostic power (e.g., accuracy, sensitivity and/or specificity). Optionally, the additional genes may be genes other than those listed in table 8. For instance, the prognostic genes may also include p53, KRAS or other markers: e.g., selected from RB, EGFR, MYC, APC, CDH13, RARB, DAPK1, DAPK2, FHIT, RASSF1A, BCL2, ERBB2 (Her2/Neu), GRP, KIT, p21, p27, p16, FAS, CASP3 (Caspase 3), BIRC5 (Survivin), VEGF, PDGF, FGF2, COL18A1 (Collagen XVIII), CCNB1, CCND1, TERT, SEMA3B, PTEN, hOGG1, BAP1, TIMP3, MGMT, FUS1, ROBO1, TSLC1, NPRL2, CYB561D2, GSTP1 and/or MGMT. Accordingly, the prognostic genes measured may consist of: no more than 14 (or 13, 12, 11 or 10) genes from table 3 including at least 6 (or 7, 8, 9 or 10) genes from table 9; plus optionally other genes not listed in either table 3 or table 9 (in some embodiments, not listed in table 8). The genes measured in the method may consist of: no more than 14 (or 13, 12, 11 or 10) genes from table 3, including at least 6 (or 7, 8, 9 or 10) genes from table 9; plus optionally other genes not listed in either table 3 or table 9 (in some embodiments, not listed in table 8); plus optionally control genes (control genes being those not associated with assessment of cancer in the method).

A useful feature of the present invention is that it provides a small, and hence more clinically useful, signature. Accordingly, it may be preferred that the total number of prognostic genes whose expression levels are measured is 50 or less, more preferably 30 or less, 25 or less, 20 or less, or 19, 18, 17, 16, 15 or less. In some embodiments, the total number of prognostic genes measured may be only 14, 13, 12, 11 or 10 (or less). Of course, in any one of these embodiments, the prognostic genes may include 7, 8, 9 or all ten of the genes from table 9.

In any of the methods mentioned above where the expression levels of genes from table 9 are measured, the genes from table 9 may in some embodiments include one or more, e.g., 2, 3 or all of HOXB7, SerpinB5, E2F4, and/or HSPG2. Additionally or alternatively, the genes from table 9 may in some embodiments include two or more, e.g., 3, 4 or all of E2F1, MCM6, SF3B1, RRM2 and/or NUDCD1. In some embodiments, it may be preferred that the genes from table 9 include HOXB7, SerpinB5, E2F4, HSPG2, E2F1, MCM6 and RRM2, and optionally also SF3B1.

In another aspect, the present invention provides a kit/apparatus suitable for use in any one of the above methods.

The invention provides a kit for use in assigning a prognosis to a subject based on a sample obtained therefrom, the kit comprising specific binding partners capable of binding to an expression product of each of a set of prognostic genes, wherein said prognostic genes include no more than 14 (optionally no more than 13, 12, 11 or 10) genes from table 3 and wherein said prognostic genes include at least 6 genes (optionally at least 7, 8, 9 or all ten genes) from table 9.

In the case of kits for FISH, the binding partners may be nucleic acids which bind the gene itself, and which are detectably labelled.

The set of prognostic genes may comprise no more than 50, 30, 25, 20, 19, 18, 17, 16, 15, 14, 13, 12, 11 or 10 genes.

As mentioned above, the kit could also comprise binding members for controls (genes not associated with prognosis). Thus, in terms of its specific binding partners, the kit may consist of specific binding partners for each of: no more than 14 (or 13, 12, 11 or 10) genes from table 3, including at least 6 (or 7, 8, 9 or 10) genes from table 9; optionally other genes not listed in either table 3 or table 9 (in some embodiments, not listed in table 8); and optionally control genes (controls genes being those not associated with assessment of cancer in the method)

Optionally, the total number of genes for which binding partners are provided in the kit, including any controls, may be fewer than 50, 30, 25, 20, 19, 18, 17, 16, 15, 14, 13, 12, 11 or 10 genes (including 6, 7, 8, 9, or 10 genes from table 9, optionally 1, 2, 3 or 4 other genes from table 3, plus optionally other prognostic markers and/or controls).

The invention also provides an apparatus comprising a solid support bearing binding partners capable of binding to an expression product of each of a set of prognostic genes, wherein said prognostic genes include no more than 14 genes from table 3 (optionally no more than 13, 12, 11 or 10 genes) and wherein said prognostic genes include at least 6 genes (optionally at least 7, 8, 9 or all ten genes) from table 9. The apparatus may consist of said solid support bearing binding members for 6, 7, 8, 9 or 10 genes from table 9, plus optionally 0, 1, 2, 3, or 4 other genes from table 3, plus optionally up to 30, 20, 10, 5, 4, 3, 2 or 1 other genes (other prognostic markers not listed in table 3 or 9 and preferably not in table 8 and/or controls).

Generally, preferred features of the methods relate equally to the kits/apparatus suitable for use in such a method.

It is noted that the prognostic genes of tables 3 and 9 include RRM2. RRM2 is associated with resistance of a variety of chemotherapeutic agents, including gemcitabine (Zhou, B. S et al. 1995, *Cancer Res* 55:1328-1333, Goan, Y. G., et al. 1999, *Cancer Res* 59:4204-4207). In pancreatic adenocarcinomas, direct targeting of RRM2 by siRNA enhanced chemosensitivity to gemcitabine both in vitro and in vivo (Duxbury, M. S et al 2004, *Oncogene* 23:1539-1548). In NSCLC, gemcitabine is one of the most active chemotherapeutic agents (Natale, R. 2005, *Lung Cancer* 50 Suppl 1:S2-4). Thus, the finding that RRM2 is overexpressed in NSCLC suggests that the status of RRM2 might influence the decision regarding alternative treatment options in place of gemcitabine.

Thus, the present invention also provides a method of determining whether or not to treat a subject identified as having NSCLC with gemcitabine or with an agent which inhibits RRM2 protein or which downregulates RRM2 expression (e.g., an antibody, or a nucleic acid inhibitor of expression such an antisense, ribozyme or siRNA molecule), the method comprising determining the status/expression level of RRM2 in a sample obtained from said subject. Preferably, the subject has a stage I tumour, e.g., a stage IA or stage IB tumour.

Overexpression of RRM2 may suggest that the subject should not be treated with gemcitabine, or should be treated with an agent which inhibits RRM2 protein or which downregulates RRM2 expression (e.g., in conjunction with treatment with gemcitabine).

The method may be used in conjunction with any of the methods for assessment/prognosis of NSCLC described herein (in which case, RRM2 should obviously be one of the prognostic genes whose expression level is examined). For instance, the invention provides a method of determining whether a patient would benefit from adjuvant therapy (by assigning a prognosis to the patient), and at the same time determining whether the adjuvant therapy should comprise the use of gemcitabine or an agent which inhibits RRM2 protein/downregulates RRM2 expression.

The invention will now be described in detail, and with reference to the following drawings:

FIG. 1 shows genes induced by E1A, and the results of RTQ-PCR in E1A (dl520) infected TD C2C12 myotubes, proliferating (MYB) C2C12 myoblasts, E1A (dl520) infected TD MSC (mouse satellite cells) and proliferating (MYB) MSC myoblasts. The first column gives the mouse accession number. The second column gives the name and description in mouse. The fourth column gives the accession number of the human sequence.

FIG. 2 shows E1A induced genes allocated to classes A, B, C or D according to their mechanism of regulation. The columns show the ratio of induction under the named conditions with induction with wild type E1A. The column headed "Ratio 24 h/36 h" shows the ratio of induction at 24 h and 36 h.

FIG. 3.

3a shows the percentage of positive tumour samples for the named genes in different tissues.

FIG. 3b shows bright field and dark field microscope analysis showing the specific signal from the cancer cells of tumour samples (T) compared to a matched normal counterpart (N). FIG. 3c shows a cell cycle plot of relative mRNA levels of 4 E1A induced genes in G0 synchronized serum starved NIH 3T3 cells stimulated by serum addition and HeLa cells released after nocodazole induced G2/M arrest. Almost all the class D genes are not cell cycle regulated in both serum response dependent and independent manner, while all the class A and B genes are cell cycle regulated and the class C genes marginally cell cycle regulated. ClassA-XTP1 (filled squares); classB-MGC22679 (empty squares); classD-TRPC4AP (empty circles); classD-SKIN (filled circles).

FIG. 4.

A) All the six class D genes result strongly overexpressed in tumours (47% to 76%) of colon cancer progression by in situ hybridization on colon specific tissue microarrays (TMA) (N=normal epithelia, I=hyperplastic polyps, A=adenomas T=adenocarcinomas).

The number on top of each column indicates the percentage of positive samples. Numbers in brackets represent the total samples tested for each stage of the progression.

B) Bright field and dark field microscope analysis matches the probe signal to the correspondent histological section.

FIG. 5.

FIGS. 5 A-C show that selected class D genes predict disease outcome in breast cancer.

Three class-D genes (SKIN, TRPC4AP and Ch-TOG) were used together as a predictor of prognostic outcome on two independent data sets, one generated by the inventors (A) and another from van't Veer (van't Veer, L. J., et al. 2002, Nature 415, 530-6) (B). Data are shown as the probability of remaining free of metastatic relapse, in a Kaplan-Meier plot, as a function of a "favourable" (dashed line), or "unfavourable" (continuous line) signature. (C). Q-RT-PCR analysis of the three predictive class-D genes was performed on 15 randomly selected breast tumour patients (all lymph node negative at diagnosis), which were all homogeneous for estrogen receptor status (ER pos). Five were N0 patients (5-years disease-free patients) and 15 were N0+ patients (patients relapsed with metastatic disease within 5 years). Q-RT-PCR values were normalized to patient 1 (assumed as 1.0). A 50th percentile value was then established for each gene and a matrix was built based on the 50th percentile value, by assigning scores of 0 or 1 to values below of above the threshold, respectively. The sum of the two matrix scores was then used to assign "favourable" (score 0-1) or unfavourable (score 2-3) labels. Probability of remaining metastasis free is shown in the Kaplan-Meier plot as a function of the presence of the "favourable" (dashed line), or "unfavourable" (continuous line) signature. In A-C, the p-values were calculated with the log-rank test.

FIG. 5D shows the probability of remaining free of distant metastasis for a patient having a good or bad prognosis based on the Class A, B and C genes predictor.

Class A, B and C were used together as a predictor of prognostic outcome on a subgroup of breast tumours with no lymph nodes involvement at surgery, which either developed metastatic disease (N0+ patients) or stayed disease-free (N0– patients) over a 5 year follow up period analysed by Affymetrix.

FIG. 6.

SKIN knock down by siRNA reduces proliferation in different tumour cell lines.

Six different tumour cell lines (as indicated) were treated with SKIN-specific siRNA (empty circles in A; RNAi in B and C), or a control scrambled oligo (filled triangles in A; scr. in B and C) or mock-treated (filled squares in A; mock in B and C). Twenty-four hours after treatment, cells were re-plated to measure cell growth (A), or analyzed for SKIN transcript levels by Q-RT-PCR (B). A. Cells, re-plated in standard growth medium, were counted at the indicated time points. Data are expressed relative to the number of cells present in the plate 24 h after re-plating (assumed as 1). B. Q-RT-PCR data are expressed relative to those detected in growing MCF10A cells, to allow for comparison among cell lines. C. In the case of DLD1 and HT-29 cells, levels of SKIN were also measured by Western Blot with an anti-SKIN antibody.

FIG. 7 shows the results of an ONCOMINE analysis of Class-D genes. The genes which pass the statistical filter (p-value<0.05 with Bonferroni correction) are shown together with their log 2 median value in every class considered, where: "N" stands for normal samples; "T" for primary tumours and "M" for distant metastasis.

A. Summary of amplification data obtained by FISH analysis of metaphase-blocked tumour cell lines with MCF10A (normal human epithelial cells) as control: "RNA level", SKIN transcripts measured by Q-RT-PCR and normalized to values in MCF10A cells; "copies", number of signals with the SKIN RP11-1139F3 probe; "chr. 8", number of signals with the 8q RP11-1031I1 probe; "ploidy", ratio between SKIN signals and chr. 8 signals. In the column "copies", additional features are marked as follows: *, tandem repeats; $, extra-chromosomal copies, #, hsr (homogenously stained region).

B. Graphical representation of results obtained by FISH analysis of human colon cancer specimens of SKIN and chromosome 8. The average number of SKIN signals/cells was counted, and normalized to the number of signals with chr.8 probe. Samples were considered amplified if >50% of the epithelial cells presented >4 signals/cell. Examples are shown: N, normal epithelium (copies/cell=2); tumour not amplified (copies/cell<4); tumour amplified (copies/cell>4). The bar graph shows the % of SKIN-overexpressing samples (evaluated by ISH) in various colon specimens (m, number of analyzed samples).

FIG. 9 shows the probability of remaining metastasis-free of patients with a good (dashed line) or poor (solid line) expression signature based on the inventor's NSCLC predictor (12 and 21 genes). P-values were calculated with the log-rank test. FIG. 9A shows the results for the 12 gene predictor for the dataset (Michigan cohort) of Beer et al. (Beer, D. G., et al, 2002. Gene-expression profiles predict survival of patients with lung adenocarcinoma. *Nat Med*, 8: 816-824), and FIG. 9B shows the results for the 12 gene predictor for the dataset (Harvard cohort) of Bhattacharjee, et al. (Bhattacharjee, A., et al, 2001. Classification of human lung carcinomas by mRNA expression profiling reveals distinct adenocarcinoma subclasses. *Proc Natl Acad Sci USA*, 98: 13790-13795). FIG. 9C shows the results of Q-RT-PCR analysis of the 12 genes predictor performed on an independent set of 30 patients, all with stage I NSCLC adenocarcinomas. Wide dashed line=undetermined. FIG. 9D shows the results of Q-RT-PCR analysis of the 21 genes predictor performed on an independent set of 30 patients, all with stage I NSCLC adenocarcinomas.

Figure 10:
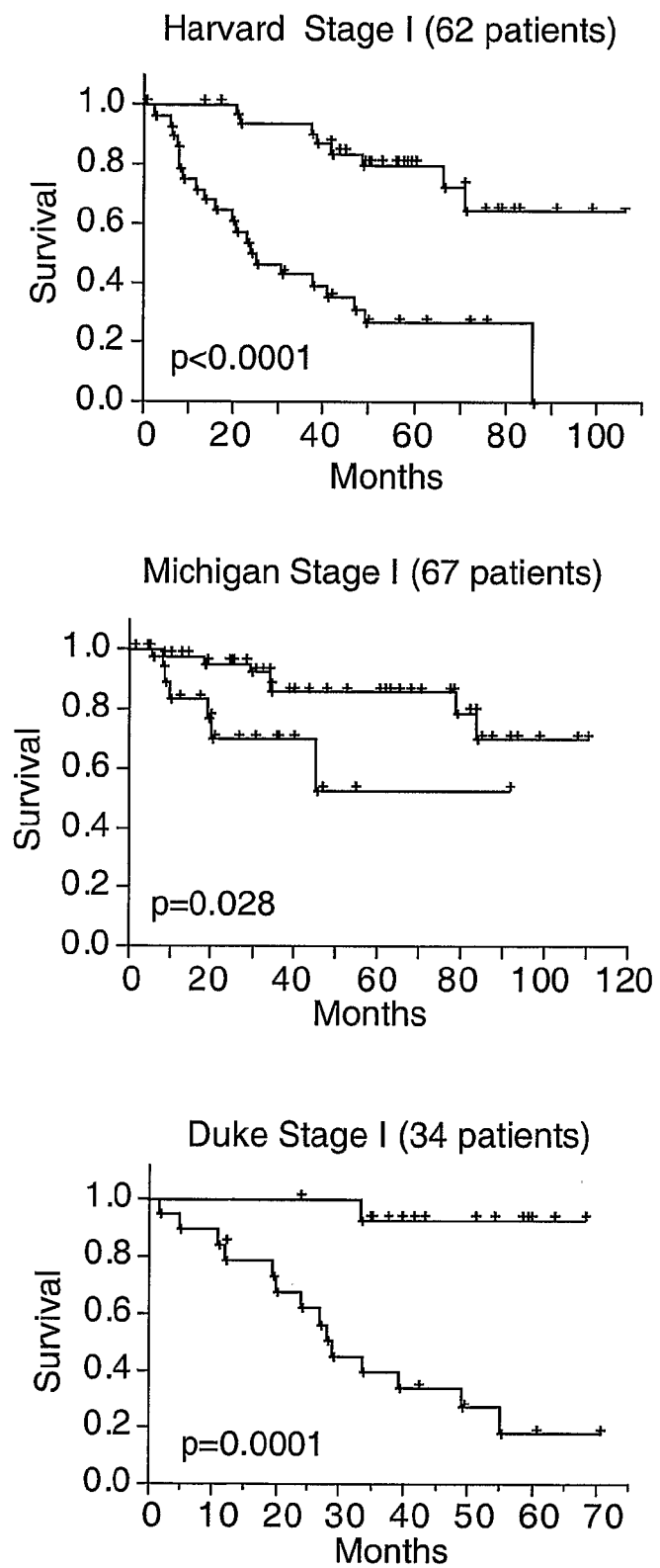

FIG. 10. The 49-gene model predicts overall survival. The 49-gene model of table 8b was used to predict overall survival in the Stage I subset of lung adenocarcinomas from the Michigan (67 of the 86 patients of the original datasets), Harvard (62 of the 84 patients of the original datasets) and Duke (34 patients) cohorts (Bild, A. H., et al, 2006. Oncogenic pathway signatures in human cancers as a guide to targeted therapies. *Nature* 439:353-357). Data are shown as the probability of survival, in a Kaplan-Meier plot, as a function of a "favorable" (upper line), or "unfavorable" (lower line) signature.

FIG. 11. The 28-gene biased signature and the 80-gene model predict overall survival. The 28-gene biased signature (A) and the 80-gene model (B) were used to predict overall survival in Stage I lung adenocarcinomas of the Duke cohort (34 patients). Data are shown as the probability of survival, in a Kaplan-Meier plot, as a function of a "favorable" (upper line), or "unfavorable" (lower line) signature.

FIG. 12. The 10-gene model predicts overall survival. The 10-gene model was tested to predict overall survival in the indicated cohorts of Stage I (A) and Stage IA (B) lung adenocarcinomas. Data are shown as the probability of survival, in a Kaplan-Meier plot, as a function of a "favorable" (upper line), or "unfavorable" (lower line) signature.

Figure 13A:
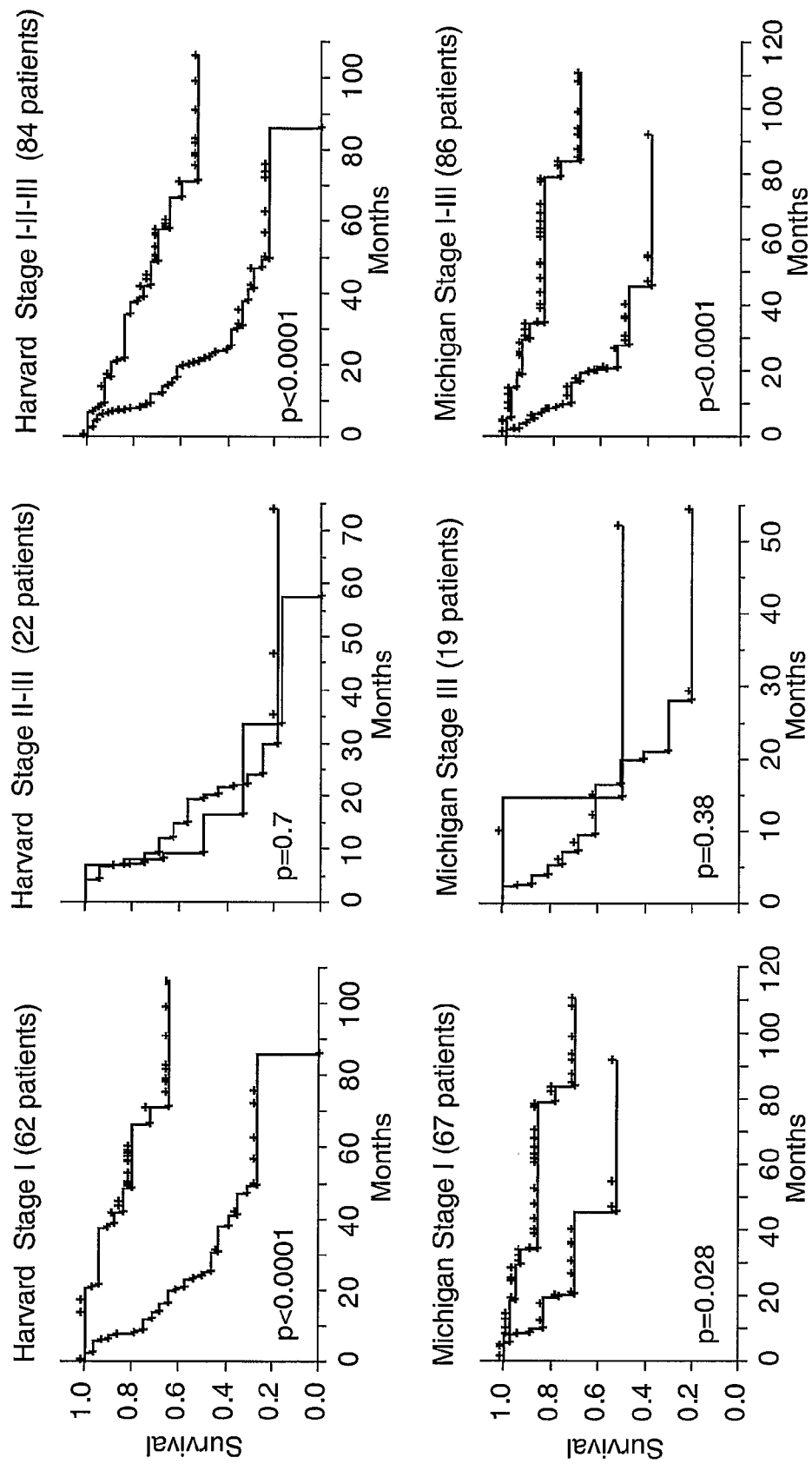

FIG. 13. Performance of the 49-gene model. In A, the 49-gene model was used to predict overall survival in lung adenocarcinoma patients of the Harvard and Michigan cohorts, as shown. Patients were divided according to tumor stage, and Kaplan-Meyer analyses are shown for Stage I patients, Stage II-III patients, and for the entire cohort (Stage I-II-III). As shown, the 49-gene model had no predictive power in Stage II-III adenocarcinomas. In B, the performance of the 49-gene model is compared to those of the 50- and 100-gene signature of Beer et al. (1) in the prediction of overall patient survival, in the Duke cohort, by Kaplan-Meyer analysis. Upper line—favorable signature; lower line—unfavorable signature (In respect of the Harvard Stage II-III group here and in FIG. 14, the favourable signature is black and the unfavourable signature is grey.)

Figure 14:
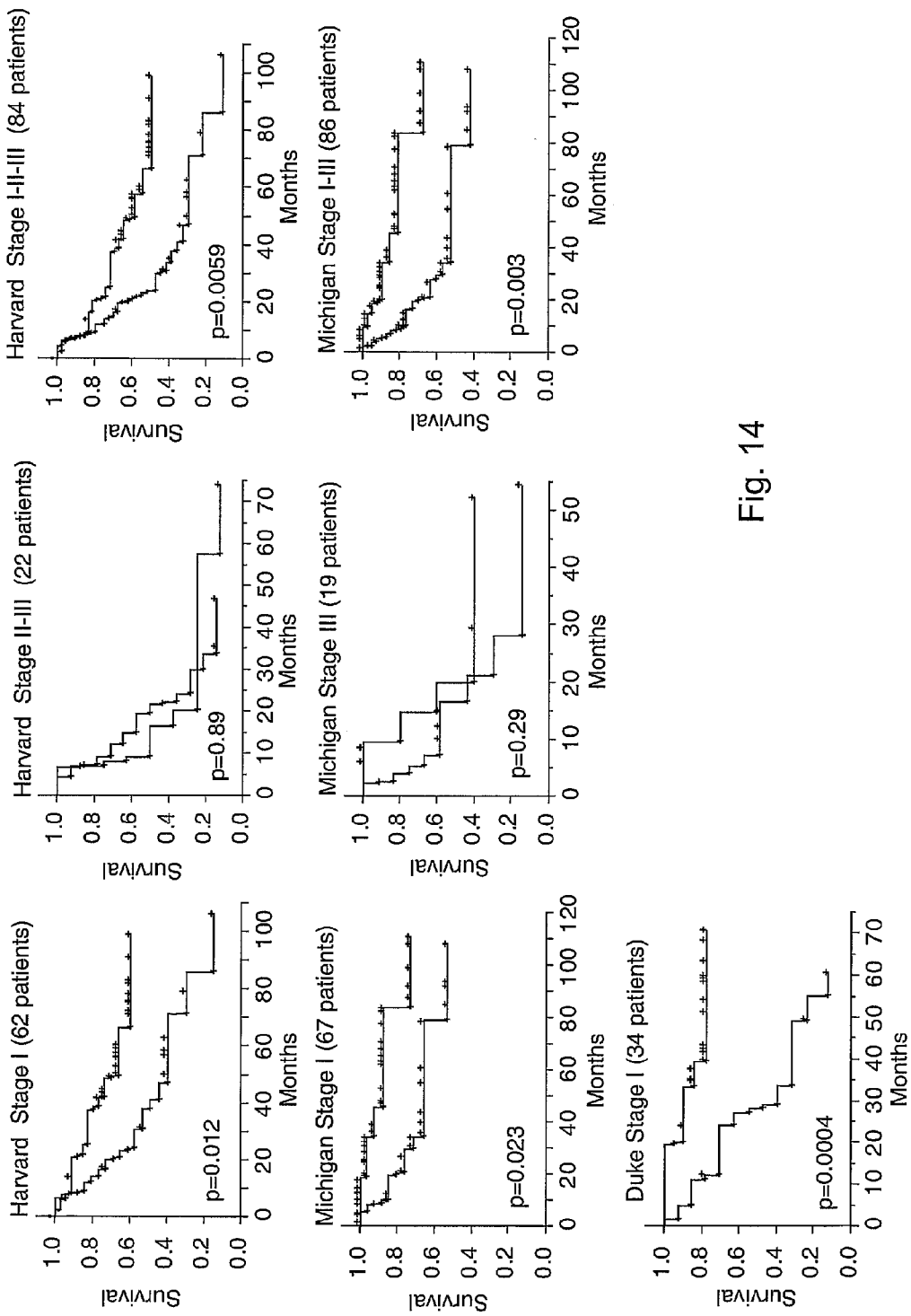

FIG. 14. Performance of the 10-gene model on the Michigan and Harvard cohorts. The 10-gene signature was used to predict overall patient survival within the Michigan and Harvard cohorts. In the case of the Michigan cohort, 7 genes could be used (SF3B1, NUDCD1 and SCGB3A1 were not present on HU6800 microarray, used in that study), in the case of the Harvard cohort, 8 genes could be used (NUDCD1 and SCGB3A1 were not present on HU95av2 microarray used in that study). Patients from the two cohorts were grouped according to the tumor stage, as described in FIG. 12. Remarkably, despite the reduction in the number of genes utilizable, the signature could still predict overall survival in patients with Stage I disease. The prediction in the Duke cohort (all 10 genes could be used in this case) is the same as in FIG. 12A and is reported for comparison.

DETAILED DESCRIPTION OF THE INVENTION

Figure 1:
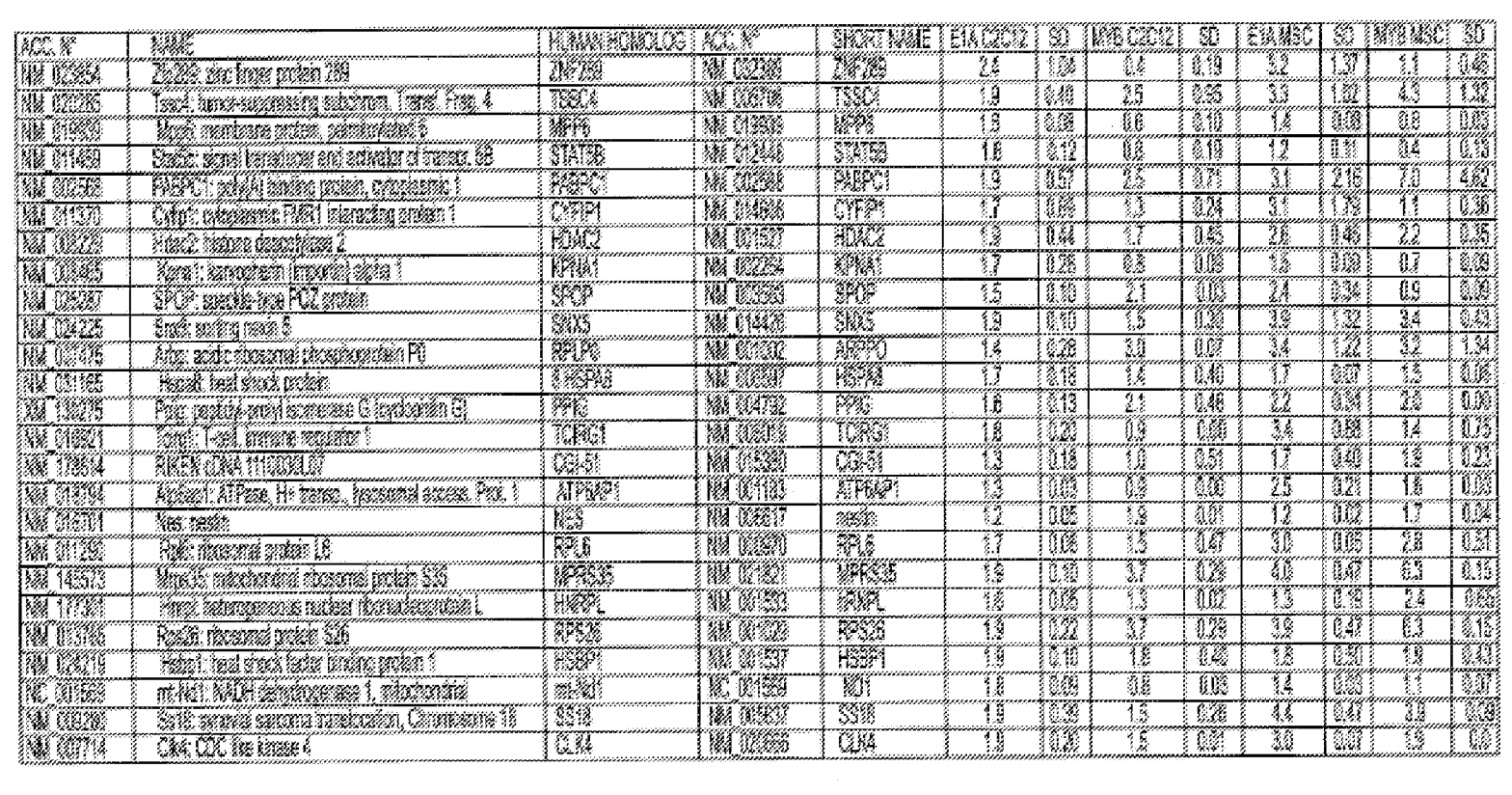

DDX21 is Deadbox polypeptide 21. SF3B1 is splicing factor 3b, subunit 1. Ch-TOG is colonic and hepatic tumour overexpressed protein and is also known as KIAA097. SKIN (similar to KIAA0493 induced in tumour) is a protein having no previously attributed function. TRPC4AP is the transient receptor potential cation channel, subfamily C, member 4 associated protein, and is also known as RRIP. SMU-1 is the Suppressor of MEC-8 and UNC-52 homolog. FIG. 1 provides the accession number for the human and mouse sequences, but reference to the gene or protein may include other mammalian sequences. The short names used herein are, for convenience, the names of the human homolog, but this is not intended to exclude other mammalian homologs. FIG. 2 provides the accession numbers for the four classes of E1A-induced genes.

Reference to E1A is intended to be reference to any adenoviral E1A expression product capable of inducing re-entry of a terminally differentiated cell into the cell cycle. Preferably, it refers to the E1A 12S mRNA product (which is the short splicing variant), or to a fragment or variant thereof which retains the biological activity.

Tables 1, 2, 3, 7, 8, 8a, 8b, and 9 provide accession numbers for the genes therein. In all cases, reference to the gene or protein may include other mammalian sequences, i.e., mammalian homologs.

Accession numbers for mRNA sequences are given above, but gene, transcript or protein may be referred to, as will be apparent from the context.

Assessment of Cancer in a Subject

A patient or subject as referred to herein is preferably a mammalian patient or subject and most preferably human.

A sample or assay sample from said patient or subject is preferably a sample of tumour tissue. In the present application, it will be understood that providing a sample obtained from a patient and determining expression levels in the sample is reference to an in vitro method practiced on a sample after removal of the sample from the body, e.g., by biopsy or during the course of surgery.

An assessment of cancer as referred to herein may be diagnosis or prognosis of the cancer. Preferably, the methods are methods of assigning a prognosis to a subject.

The assigned prognosis may be "good" or "poor" prognosis. In some embodiments, the assigned prognosis may be a probability of survival after a given period of time, e.g., at five years (categorical or numerical probability).

Cancers may be clinically assigned to various stages. The most commonly used staging system for both breast cancer and NSCLC is the TNM system, which is widely described in the art. It may be preferred that the methods are methods of assigning a prognosis to a patient having an early stage cancer.

According to the sixth edition of TNM, in breast cancer an early stage tumour is defined as a tumour that has not spread beyond the breast or the axillary lymph nodes (Tis, T1, T2, N0, M0).

In lung cancer an early stage tumour is defined as a tumour that has not lymph node metastases or spread is confined to hilar lymph nodes. This includes stage I and stage II lung cancer.

Cancer may be e.g., melanoma, or cancer of the breast, colon, kidney, larynx, lung, prostate, stomach, uterus or brain. In some embodiments, it is preferred that the cancer is NSCLC. Preferably, the cancer is an adenocarcinoma, e.g., an NSCLC adenocarcinoma.

The chance of surviving non-small cell lung carcinoma (NSCLC) is greatly increased if the disease is caught in the early stages. According to the TNM system, stage I tumours are defined as T1N0M0 (stage IA) or T2N0M0 (stage IB). T refers to the primary tumour as below:

T1—Tumour with diameter of 3 cm or smaller and surrounded by lung or visceral pleura, without bronchoscopic evidence of invasion more proximal than lobar bronchus (i.e., not in the main bronchus)

T2—Tumour with any of the following features of size or extent:
  diameter greater than 3 cm;
  invade the visceral pleura,
  extend into the main bronchus but remains more than 2 cm from the carina;
  associated with atelectasis, or obstructive pneumonitis but not involving the entire lung;

N0 refers to no lymph node involvement and M0 refers to no distant metastasis.

The treatment of choice for early stage NSCLC patients is generally surgery alone, since the majority of patients receiving adjuvant chemotherapy would be exposed to toxicity without any real benefit. Thus, tools which could determine the early stage NSCLC patients who would have the potential to benefit from adjuvant therapy would be highly desirable.

Methods of the present invention are preferably used to assign a prognosis to a patient having a stage I tumour, e.g., a stage IA or stage IB tumour. In some embodiments it may be preferred that the patient has a stage IA tumour. In some embodiments it may be preferred that NSCLC is an adenocarcinoma, e.g., a stage I (A or B) NSCLC adenocarcinoma. In some embodiments, "good" prognosis patients may be advised not to have adjuvant therapy, whereas "poor" prognosis patients may be advised to have adjuvant therapy.

Accordingly, the method may comprise assigning the patient to a treatment group, which may be a "with" or "without" adjuvant therapy group; in other words, the method may comprise determining whether a patient should have adjuvant therapy (by assigning a prognosis to the patient).

Adjuvant therapy is therapy applied in addition to a primary therapy (e.g., surgery) and is intended to reduce the risk of cancer recurrence. Examples of adjuvant therapies include chemotherapy, radiotherapy, immunotherapy, targeted therapy or hormone therapy.

The methods of the invention may also comprise comparing the protein status or expression level to that of a control sample, as explained in more detail below. When the control sample is a sample of normal cells or a sample of tumour cells having good prognosis, then a poor prognosis may be suggested by a gene status or by a level of a gene expression product which is divergent from the level in the control. When the control is associated with poor prognosis then poor prognosis may be suggested by gene status or a level of gene expression products which is in line with or similar to the control sample. Of course, as explained further below, more than one control may be used.

Poor prognosis may be associated with downregulation or upregulation of expression of a given gene, e.g., with downregulation or upregulation of a mRNA or protein expression product, relative to a reference expression level, such as a control or a good prognosis group. When a plurality of genes is measured, patients may be assigned to the poor/good prognosis group depending on the number of genes they have following the poor/good prognosis pattern. E.g., they may be put in the poor/good prognosis class if they have more than 20%, 25%, 30%, 35%, 40%, 45%, 50%, 55%, 60%, 65% or 70% of genes following a poor/good prognosis pattern. The chosen level will depend on the individual circumstances.

In all of the methods of the present invention, of course, the method may also comprise measuring genes as controls (e.g., housekeeping or universally expressed genes), wherein in the course of said method no association is made between the expression level of the controls and prognosis. The term "prognostic genes" herein is intended to exclude such controls.

Moreover, the assignment of a prognosis may take account of other factors and clinical parameters such as the tumour size, tumour grading, tumour infiltration, and degree of metastasis of the tumour.

As well as the expressly mentioned genes, the methods may include measuring other prognostic genes in order to further increase prognostic power (e.g., accuracy, sensitivity and/or specificity). For instance, the prognostic genes may also include p53, KRAS or other markers: e.g., selected from RB, EGFR, MYC, APC, CDH13, RARB, DAPK1, DAPK2, FHIT, RASSF1A, BCL2, ERBB2 (Her2/Neu), GRP, KIT, p21, p27, p16, FAS, CASP3 (Caspase 3), BIRC5 (Survivin), VEGF, PDGF, FGF2, COL18A1 (Collagen XVIII), CCNB1, CCND1, TERT, SEMA3B, PTEN, hOGG1, BAP1, TIMP3, MGMT, FUS1, ROBO1, TSLC1, NPRL2, CYB561D2, GSTP1 and/or MGMT. However, it may be preferred that the total number of prognostic genes (i.e., genes other than controls) whose expression levels are measured is 100, 75, 50 or less, more preferably 30 or less, and in some embodiments 25 or less, 20 or less, or 19, 18, 17, 16, 15 or less. In some embodiments, the total number of prognostic genes measured may be only 14, 13, 12, 11 or 10 (or less). In some embodiments, it may be preferred that the total number genes (e.g., including both prognostic and control genes) measured is 100, 75, 50 or less, more preferably 30 or less, and in some embodiments 25 or less, 20 or less, or 19, 18, 17, 16, 15 or less.

Determination of Protein, Gene or Transcript Levels

Determination of protein, gene or transcript level (to determine expression level) may be made by any of the methods known in the art.

For example, the method may comprise measuring the level of a protein or a nucleic acid, which may be DNA or mRNA.

It may be preferred that the methods comprise direct measurement of the level of a gene expression product. A gene expression product as referred to herein may be a protein or a transcript (i.e., an RNA molecule expressed by the gene).

For example, suitable methods for assessing protein levels include immunohistochemistry (e.g., immunofluorescence), western blotting, and solid phase methods such as ELISA (enzyme-linked immunoabsorbent assay).

Using immunohistochemical techniques, an assessment of protein level can be made by determining the proportion of cells showing labelling (e.g., staining or fluorescence).

Transcript level may be determined by in situ hybridisation, e.g., accompanied by assessment of the proportion of cells showing hybridisation.

Alternatively, or in addition, quantitative PCR methods may be used, e.g. based upon the ABI TaqMan™ technology, which is widely used in the art. It is described in a number of prior art publications, for example reference may be made to WO00/05409. PCR methods require a primer pair which target opposite strands of the target gene at a suitable distance apart (typically 50 to 300 bases). Suitable target sequences for the primers may be determined by reference to Genbank sequences.

Where many different gene transcripts are being examined, a convenient method is by hybridisation of the sample (either directly or after generation of cDNA or cRNA) to a gene chip array and/or micro fluidic card (Low density array). Quantitative PCR methods may use microfluidic techniques, e.g., a microfluidic card.

Thus, the method may comprise contacting the sample with a substrate bearing a plurality of nucleic acids. The substrate bears nucleic acids hybridising specifically to transcripts of each of the genes whose expression level is to be detected.

Where gene chip technology is used, the genes may be present in commercially available chips from Affymetrix, and these chips may be used in accordance with protocols from the manufacturer. Generally, examples of methods for the provision of microarrays and their use may also be found in, for example, WO84/01031, WO88/1058, WO89/01157, WO93/8472, WO95/18376/WO95/18377, WO95/24649 and EP-A-0373203 and reference may also be made to this and other literature in the art.

Where microfluidic card technology is used, the genes may for instance be present in commercially available microfluidic cards from Applied Biosystem, also known as Low Density Arrays. These cards may be used in accordance with protocol from the manufacturer.

TaqMan® Low Density Arrays are customizable, easy-to-use, 384-well micro fluidic cards for real-time PCR-based quantitative gene expression applications (ABI TaqMan™ technology). Over than 40,000 inventoried TaqMan® assays covering human, mouse, and rat genes, are commercially available.

The micro fluidic technology uses 8 sample-loading ports, each connected to 48 reaction wells.

384 well TaqMan® array is run on the Applied Biosystems 7900HT Fast Real Time PCR System.

Gene copy number may be determined using techniques known in the art, including in situ hybridisation (ISH) with nucleic acid probes which may be labelled with e.g. a fluorescent label (FISH), or PCR of genomic DNA.

Reference or Control Samples

When a method of the invention comprises determining the gene status of an assay sample obtained from a patient and/or determining the expression level, the method may also comprise comparing the determination made on that sample with a determination made on a reference or control sample.

Reference or control samples for the above methods may be a sample of normal (unaffected) cells, preferably cells of the same type as the assay sample. Alternatively, the sample may be a sample of cells affected by cancer, preferably a cancer of the same type as is in the patient or is suspected to be in the patient.

Where the aim is to distinguish between different states or different levels of aggression of a cancer (e.g., in a method of prognosis), the control sample may preferably be taken from a tumour cell having one of the states of interest. For example, the control sample may be a sample taken from a tumour from a metastatic tumour, or may be a sample from a non-metastatic tumour. For colon cancer, the control sample may be taken from one or more of hyperplastic polyps, adenomas and carcinomas. Generally, the control sample may be a sample of cells from a tissue type associated with the presence or absence of cancer, and/or from a tumour with good or with poor prognosis.

The control sample may be obtained from the patient, from another subject or from a population of subjects. Where a population of subjects is used, the comparison may be made with the average (e.g., mean or median) in samples of cells from said population.

One advantage of using a control of normal tissue from the same patient is that it accounts for any individual variation.

Where the control is from another patient (either of normal or affected tissue), this may also be a reason why results based on a population of patients may be preferred.

In some embodiments, the method may comprise the use of more than one control; for example the sample to be tested may be compared to a normal sample from the same patient and the transcript level of an affected sample from another patient or patients. In another example, the sample to be tested may be compared to one or more sample from a metastatic tumour and one or more samples from a non-metastatic tumour.

Where the assay sample is a sample of affected tissue obtained from the patient, it may be preferred that the control sample is obtained from the patient at an earlier time point, so as to provide a historical record. In one embodiment, this allows for monitoring of the progression of the condition over time.

In another embodiment, this allows for assessment of the effectiveness of a particular treatment. By comparing the severity of the condition in a patient at two time points, it is possible to determine whether a particular treatment regime is having a positive effect or not. The effectiveness of any one regime may differ from patient to patient, or during the course of the disease.

Comparison to the gene status or to the level of a gene expression product in a control sample may of course be comparison to previously determined data, and need not comprise the step of analysing the control sample.

Specific Binding Partners and Kits/Apparatus

The specific binding partner for a protein may be an antibody, as defined below, and is preferably a monoclonal antibody. The antibody may be detectably labelled.

Where the gene expression product is a transcript, the specific binding partner may be a nucleic acid sequence capable of specifically hybridising to said transcript. The nucleic acid sequence may be detectably labelled. It may be a primer or primer pair, e.g., for quantitative PCR.

By "specific" is meant a binding partner which is suitable for detection of the transcript or protein in a complex mixture. The binding partner may bind to the gene expression product preferentially over other transcripts/proteins in the same species and may have no or substantially no binding affinity for other proteins or transcripts. In the case of a transcript, the transcript is preferably capable of distinguishing the target transcript from other transcripts in the mixture at least under stringent hybridisation conditions.

In various aspects, the invention relates to a kit or an apparatus which comprise a specific binding partner for a gene expression product. In some embodiments, the specific binding partner may be immobilised on a solid support. Thus, the kit for assessment of a sample may comprise an apparatus comprising or consisting of a solid support bearing binding partners for each of the genes of interest.

Where the specific binding partner is an antibody, the kit may further comprise a detectably labelled moiety capable of binding to a complex between the protein and its specific binding partner. Additionally or alternatively, the kit may include one or more of the following reagents:
a) a reagent to fix a tissue, such as paraformaldeheyde;
b) a reagent to "unmask" cellular antigens upon fixation (such as EDTA-based solutions or citrate buffer); and/or
c) a detection system to reveal the enzymatic activity coupled to the primary antibody or the secondary moiety (e.g., secondary antibody), where the label is an enzyme, such as peroxidase.

For example, the kit may be for immunohistochemical techniques, and may comprise a first antibody capable of binding the protein to be detected, and a second, labelled antibody capable of binding said first antibody.

Alternatively, the kit may comprise a first, immobilised antibody capable of binding the protein to be detected and a second, labelled antibody capable of binding the protein when bound to the first antibody.

A label may be a radioactive, fluorescent chemiluminescent or enzyme label. Radioactive labels can be detected using a scintillation counter or other radiation counting device, fluorescent labels using a laser and confocal microscope, and enzyme labels by the action of an enzyme label on a substrate, typically to produce a colour change. After the binding reaction and any necessary separation step has taken place, the result of the assay is obtained by contacting the enzyme with a substrate on which it can act to produce an observable result such as a colour change, the extent of which depends on the amount of analyte originally in the sample. Suitable enzyme labels may give rise to detectable changes such as colorimetric, fluorometric, chemiluminescent or electrochemical changes, and include horseradish peroxidase and alkaline phosphatase, as well as lysozyme (detectable for example by lysis of organisms such as microccocus lysodeikticus), chymotrypsin, and E. coli DNA polymerase.

Other possible labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors.

Other methods may also be used to detect interaction between the protein and the antibody, including physical methods such as surface plasmon resonance, agglutination, light scattering or other means.

In another embodiment, the kit may comprise primers for PCR analysis of RNA samples or genomic DNA from patients, i.e., primers which are capable of hybridising to an RNA expression product of the gene in question, or to the gene itself, and of serving as extension primers. Optionally, the PCR may be quantitative PCR.

In other embodiments, the kit may be a gene chip array, in which case it preferably comprises a control specific for said at least one transcript; and optionally at least one control for the gene chip.

In another embodiment, the kit may comprise probes for FISH analysis of gene copy number or other genetic alterations.

E.g., the kit may comprise nucleic acids capable of binding to each of a set of prognostic genes, wherein said nucleic acids are detectably labelled (preferably fluorescently labelled).

The identification of a relatively small set of genes of use in assessing the conditions discussed above allows the provision of a small chip specifically designed to be suitable for use in the present invention.

Desirably, the number of sequences in the array will be such that where the number of nucleic acids suitable for detection of the marker transcript is n, the number of control nucleic acids specific for individual transcripts is n', where n' is from 0 to 2n, and the number of control nucleic acids (e.g. for detection of "housekeeping" transcripts, transcripts having normally high levels in the cell type being assessed, or the like) on said gene chip is m where m is from 0 to 100, preferably from 1 to 30, then n+n'+m represent at least 50%, preferably 75% and more preferably at least 90% of the nucleic acids on said chip.

The array may comprise binding partners for a total of e.g., less than 1000, 500, 400, 300, 200, 100, 50, 40, 30, 25, 20 or 15 prognostic genes.

It may be preferred in general that the kit or apparatus comprises binding partners for no more than 500, 400, 300, 200, 100, 50, 30, 25, 20, 19, 18, 17, 16, 15, 14, 13, 12, 11 or 10 prognostic genes.

As mentioned above, the kit or apparatus could also comprise binding members for controls (genes not associated with prognosis).

Optionally, the total number of genes for which binding partners are provided in the kit or apparatus, including any controls, may be fewer than 500, 400, 300, 200, 100, 50, 30, 25, 20, 19, 18, 17, 16 or 15.

Antibodies

Methods of producing antibodies are known in the art. Preferred antibodies are isolated, in the sense of being free from contaminants such as antibodies able to bind other polypeptides and/or free of serum components. Monoclonal antibodies are preferred for some purposes, though polyclonal antibodies are within the scope of the present invention.

Where the kits comprise more than one antibody, these are preferably mixtures of isolated antibodies as described above.

Antibodies may be obtained using techniques which are standard in the art. Methods of producing antibodies include immunising a mammal (e.g. mouse, rat, rabbit) with a polypeptide of the invention. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80-82, 1992).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. Another example of a suitable library is a Llama library.

Antibodies according to the present invention may be modified in a number of ways. Indeed the term "antibody" should be construed as covering any binding substance having a binding domain with the required specificity, e.g., antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with the alteration of some of the framework amino acid residues, to provide antibodies which are less immunogenic than the parent non-human antibodies, are also included within the present invention.

Assay Methods

The present invention also provides for the use of a protein selected from DDX21, SF3B1, ch-TOG, SKIN, TRPC4AP and SMU-1 or other gene listed in FIG. 2, a protein of table 2, a protein of table 3 or a protein of table 8 or 9 for screening for a candidate agent for the treatment of cancer in a patient.

In a still further embodiment, the invention provides a method of screening for a candidate agent for the treatment of cancer in a patient, comprising:
a) providing a protein selected from DDX21, SF3B1, ch-TOG, SKIN, TRPC4AP and SMU-1 or other gene listed in FIG. 2, or a protein of table 2, table 3 or table 8 or 9;
b) bringing the protein into contact with a test agent;
c) determining whether said test agent is capable of binding and/or modulating the activity of the protein.

In another aspect, the invention provides a method of screening for a candidate agent for the treatment of cancer in a patient, comprising:
identifying a gene whose expression is modulated in a terminally differentiated mammalian cell in culture by contacting the cell with E1A so as to cause its re-entry into the cell cycle;
providing a protein expressed by the gene;
bringing the protein into contact with a test agent; and
determining whether said test agent is capable of binding and/or modulating the activity of the protein.

The invention also provides a method of screening for a candidate agent for the treatment of cancer in a patient, wherein said method comprises
a) providing a transformed cell in culture;
b) bringing said cell into contact with a test agent; and
c) determining whether said test agent is capable of modulating the level of a transcript selected from DDX21, SF3B1, ch-TOG, SKIN, TRPC4AP and SMU-1 or other transcript listed in FIG. 2, or a transcript of table 2, table 3 or table 8 or 9.

In another aspect, the invention provides the use of an agent obtainable in one of the above screening methods for the manufacture of a medicament for the treatment of cancer.

The cancer may be e.g., melanoma, or cancer of the breast, colon, kidney, larynx, lung, prostate, stomach, uterus or brain. In some embodiments, it is preferred that the cancer is NSCLC. Preferably, the cancer is an adenocarcinoma, e.g., an NSCLC adenocarcinoma.

The protein used in the above assays may be a mammalian protein, preferably a human protein. It may also be a fragment or variant of the full length mammalian protein. Preferred fragments and variants are those which retain the activity of the mammalian protein. Fragments may comprise at least 10, more preferably at least 20, 30, 40 or 50 consecutive amino acids of the mammalian protein sequence. A variant may have at least 70%, 80%, 90%, 95% or 99% identity to a full length mammalian sequence, preferably to the human sequence, assessed over the full length of the mammalian sequence.

The percentage identity of amino acid sequences can be calculated using commercially available algorithms. The following programs (provided by the National Center for Biotechnology Information) may be used to determine homologies: BLAST, gapped BLAST, BLASTN and PSI-BLAST, which may be used with default parameters.

The protein for use in the assay may be fused to a heterologous sequence, e.g., a sequence allowing the protein to be isolated and/or immobilised.

The ability of a test agent to bind to the protein may be assessed by any of the methods known in the art. Binding assays may be competitive or non-competitive.

The assay method may comprise determining whether the test agent is capable of inhibiting the protein, or determining whether the test agent is capable of activating the protein.

Where the gene expression is downregulated in a human tumour, the assay is preferably for an activator of the protein, and the assay preferably involves determining whether the test agent is capable of increasing the activity of the protein. In this embodiment, the assay may be carried out under conditions where the protein normally shows low or no activity.

Where the gene expression is upregulated in a tumour, the assay is preferably for an inhibitor of the activity of the protein, and the assay preferably involves determining whether the test agent is capable of reducing the activity of the protein. In this embodiment, the assay may be carried out under conditions in which the protein is normally active.

The determination of modulation of activity will depend upon the nature of the protein being assayed. For example, proteins with enzymatic function may be assayed in the presence of a substrate for the enzyme, such that the presence of a test agent capable of modulating the activity results in a faster or slower turnover of substrate. The substrate may be the natural substrate for the enzyme or a synthetic analogue. In either case, the substrate may be labelled with a detectable label to monitor its conversion into a final product.

For proteins with a ligand binding function, such as receptors, the test agent may be examined for ligand binding function in a manner that leads to antagonism or agonism of the ligand binding property.

For proteins with DNA binding activity, such transcription regulators, the DNA binding or transcriptional activating activity may be determined, wherein a modulator is able to either enhance or reduce such activity. For example, DNA binding may be determined in a mobility shift assay. Alternatively, the DNA region to which the protein bind may be operably linked to a reporter gene (and additionally, if needed, a promoter region and/or transcription initiation region between said DNA region and reporter gene), such that transcription of the gene is determined and the modulation of this transcription, when it occurs, can be seen. Suitable reporter genes include, for example, chloramphenicol acetyl transferase or more preferably, fluorescent reporter genes such as green fluorescent protein.

Test agents may be natural or synthetic chemical compounds used in drug screening programmes. Extracts of plants, microbes or other organisms, which contain several characterised or uncharacterised components may also be used. Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. Many such libraries are commercially available and sold for drug screening programmes of the type now envisaged by the present invention.

A further class of test agents or candidate modulators are antibodies or binding fragment thereof which bind a protein target, as described above.

Another class of test agents are peptides based upon a fragment of the protein sequence to be modulated. In particular, fragments of the protein corresponding to portions of the protein which interact with other proteins or with DNA may be a target for small peptides which act as competitive inhibitors of protein function. Such peptides may be for example from 5 to 20 amino acids in length.

The peptides may also provide the basis for design of mimetics, as explained in more detail below.

In other aspects, the invention provides methods comprising the step of providing a transformed cell in culture, and determining whether a test agent is capable of modulating (inhibiting or activating) the levels of a gene transcript.

In such a method, the transformed cell may be a tumour cell, e.g., isolated from a human subject, or may be a cell which has been contacting with a transforming agent or an agent which causes re-entry of a terminally differentiated cell into the cell cycle. For example, the cell may be a cell which has been contacted with an E1A protein as described above, e.g., by infecting the cell with an adenovirus. The cell may be a terminally differentiated cell.

Cell based assay methods can be configured to determine expression of the gene either at the level of transcription or at the level of translation. Where transcripts are to be measured, then this may be determined using the methods described above, e.g. on gene chips, by multiplex PCR, or the like.

As above, where the transcript is one which is down-regulated in tumours, the assay is preferably for agents which increase the expression of the gene (e.g., by increasing the quantity of the transcript). Such an agent may comprise the coding sequence of the gene itself (i.e., it may be a gene therapy vector). Where the transcript is one which is upregulated in human tumours, the assay is preferably for agents which decrease the expression of the gene.

Cell based assay methods may be used to test agents of the sorts described above. They may also be used to screen further classes of test agents/candidate modulators, including antisense oligonucleotides. Such oligonucleotides are typically from 12 to 25, e.g. about 15 to 20 nucleotides in length, and may include or consist of modified backbone structures, e.g. methylphosphonate and phosphorothioate backbones, to help stabilise the oligonucleotide. The antisense oligonucleotides may be derived from the coding region of a target gene or be from the 5' or 3' untranslated region. Test agents may further include RNAi, i.e. short double stranded RNA molecules which are sequence specific for a gene transcript. They may also include ribozymes which specifically target the transcript mRNA, i.e., a catalytic RNA molecule which cleaves other RNA molecules of a particular nucleic acid sequence. General methods for the construction of ribozymes are known in the art.

Agents obtained in accordance with the present invention may be used in methods of treating cancer in a patient. Generally, the modulator will be formulated with one or more pharmaceutically acceptable carriers suitable for a chosen route of administration to a subject. For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, a modulator and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Routes of administration may depend upon the precise condition being treated.

Design of Mimetics

Once candidate substance have been found in the assays and screens according to the present invention, they may be used to design mimetic compounds for development as drugs. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

EXAMPLES

The following examples are provided by way of illustration.

Example 1

We used a cDNA subtraction approach to clone genes whose expression is induced by E1A, concomitantly to its induction of re-entry in the cell cycle of TD myotubes.

TD C2C12 myotubes were infected with either the adenovirus dl520 (expressing only the 12S mRNA of E1A) or the control adenovirus dl312 (expressing no E1A mRNA). Only the dl520 infected myotubes displayed 48 h p.i. S-phase re-entry phenotype (about 70%). 2 µg of time course pooled polyA$^+$ RNA from dl520 and dl312 infected myotubes was used as starting material for cDNA retro-transcription (Invitrogen) and subtraction procedures (Clonetech) to obtain a library of about 800 clones.

E1A induced library was screened by Reverse Northern. 14 filters (7 plates, 2 filter per plate) contained all the cloned sequences as single purified PCR bands and some controls (DNA ladder IX as negative control, adenoviral cDNA and NP95 sequence as positive control, GAPDH as internal standard). Each plate (2 filters) was hybridized in duplicate with two different labelled cDNA pools (dl520 and dl312 infected myotubes cDNA) to fish out by comparing the radioactive signals only the E1A (dl520) induced clones. The single positives clones were picked, then grown and sequenced to retrieve by blast analysis the corresponding gene.

Each gene was then validated by Q-RT-PCR onto RNA from E1A and mock infected myotubes.

Specifically, the Reverse Northern positive E1A induced genes are validated by SYBR GREEN based quantitative RT PCR on RNA from E1A (dl520) infected TD C2C12 myotubes, proliferating (MYB) C2C12 myoblasts, E1A (dl520) infected TD MSC (mouse satellite cells) and proliferating (MYB) MSC myoblasts.

FIG. 1 shows the results of the validation. It shows 55 non-redundant clones of which 29 (henceforth referred to as E1A-induced genes) showed reproducible, and greater than 2-fold, induction, upon E1A expression in both TD C2C12 mouse myotubes and primary TD muscle satellite cells (MSC).

All the fold values are calculated using as reference mock infected (dl312) myotubes (value 1.00) and as standard mouse GAPDH gene. The values are expressed as average of two independent experiments and standard deviation (SD).

The 29 E1A induced display different timing of induction after E1A expression onto TD C2C12 myotubes. Two time points were considered: 24 h/EARLY (soon after E1A protein starts accumulating) and 36 h/LATE (immediately before S-phase re-entry). The transcriptional activation of each gene was measured as E1A (dl520) fold induction referred to mock infected myotubes (dl312) of two independent experiments by SYBR GREEN based Q-RT-PCR. A mathematical ratio calculated between 24 h/EARLY and 36 h/LATE E1A induction defined the timing of activation. EARLY=>0.4; LATE=<0.4.

Of the 29 genes, 14 genes were early-induced and 15 were late-induced by E1A (FIG. 2).

Of interest, almost all of the E1A-induced genes, were actively transcribed in proliferating myoblasts, indicating that the E1A-induced program proceeds through the reactivation of programs switched off by terminal differentiation and withdrawal from the cell cycle (FIG. 1).

Example 2

E1A exerts pleiotropic effects on TD myotubes. It suppresses tissue-specific genes, through its binding to the transcriptional co-activators p300/CBP and MyoD, and reactivates the cell cycle, through a mechanism in which binding to pocket proteins (mainly pRb and p130) and restoration of E2F activity is pivotal. However, the ectopic expression of E2Fs in TD myotubes does not induce S phase, indicating that other E1A-activated pathways are concomitantly needed. Indeed E1A-regulated pocket/Rb-independent mechanisms are known, which involve CycE/CDK2-, CtBP-, TRAPP- or p400-regulated pathways, and other chromatin remodelling activities. While it is unclear how these activities contribute to the creation of a S-phase environment, there is evidence that some of these pocket/E2F-independent pathways contribute to E1A-mediated oncogenesis. In keeping with our initial strategy, we tried therefore to classify the E1A-induced genes according to their upstream mechanism of regulation.

We employed three strategies in TD myotubes: i) overexpression of E2F1, to identify those genes whose induction is E2F1-dependent, using Ad-E2F1 adenovirus infection (MIO 300) as described in Pajalunnga et al 1998; ii) expression of an E1A mutant (YH47/dl928) that is unable to bind to pocket proteins, to identify genes whose induction is dependent on the interference of E1A with pocket protein activity; iii) removal of the Rb gene in TD myotubes derived from MSC from Rb-floxed mice (Vooijs et al 1998). In this latter case, removal of Rb by Cre recombinase was obtained after the induction of terminal differentiation, in an attempt to mimic the effects of E1A exclusively dependent on interference with Rb.

We analysed the expression of the E1A-induced genes under these conditions using Q-RT-PCR, in comparison to the levels obtained upon expression of E1A (FIG. 2).

Total RNA was isolated with the Triazol method (Invitrogen). Two µg of RNA were used, with 100 ng of random examers, in a reverse transcription reaction (SUPERSCRIPT II, Invitrogen). One-tenth ng of cDNA was amplified, in triplicate, in a reaction volume of 20 µL with 10 pMol of each gene specific primer and the SYBR-green PCR MasterMix (Applied Biosystems). Real-time PCR was carried out on the ABI/Prism 7700 Sequence Detector System (Perkin-Elmer/Applied Biosystems), using a pre-PCR step of 10 min at 95° C., followed by 40 cycles of 15 s at 95° C. and 60 s at 60° C. Specificity of the amplified products was confirmed by melting curve analysis (DISSOCIATION CURVE™ Perkin-Elmer/Applied Biosystems) and by 6% PAGE. Preparations with RNA template without reverse transcriptase were used as negative controls. Samples were amplified with primers for each genes (for details see Q-PCR primer list below) and GAPDH as a housekeeping gene (other housekeeping genes, including rRNA 18S and beta-actin were also tested with comparable results). The Ct values were normalized to the GAPDH curve and the relative expression of each gene was expressed as the ratio relative to mock (dl312) infected myotubes.

The following major classes of genes could be identified:

Class A. Pocket-dependent (not induced by YH47, strongly induced by Rb removal), E2F1-dependent (strongly induced by E2F1 overexpression) genes (7 genes).

Class B. Pocket-dependent, E2F1-independent (or scarcely-dependent) genes (8 genes).

Class C. Pocket-indifferent (well-induced by YH47, but also activated by Rb removal). This group of 9 genes is clearly subjected to dual redundant regulation, both pocket-dependent and -independent. Almost all of these genes are E2F1-independent, with the exception of KIAA0648.

Class D. Pocket-independent (or substantially-independent) genes. This group of 6 genes is well activated by YH47 and scarcely by Rb removal. In addition almost all of them are E2F1-independent, with the marginal exception of KIAA0097.

A first genetic cluster, comprising class A and B genes, is constituted by "typical" E1A-responsive genes, whose induction is stringently pocket protein-dependent (regardless of the E2F1-dependence). All the early-induced genes belong to this group. Of interest, a subset of genes in this genetic cluster (MCM7, MCM4 and MCM6), which is widely known to be under the transcriptional control of E2F1 in non-post-mitotic cells, does not seem to be responsive to the overexpression of this protein in a TD environment, despite retaining pocket protein-dependence. This result suggests there is a difference in the transcriptional regulation of pocket/E2F genes in reversibly and irreversibly arrested cells, and provides a tentative hypothesis as to why E2Fs are unable to force the re-entry in the cell cycle of TD cells.

A second genetic cluster (class C and D) is made up of pocket-indifferent or pocket-independent genes. It is not clear why all these genes are "late" genes, albeit the correlation is too strong to be due to chance. More importantly, within this cluster, class D genes constitute a transcriptional signature, induced by a well-defined genetic alteration, through a yet unknown mechanism. Since pocket-protein/E2Fs-independent mechanisms are known to contribute to E1A-induced tumourigenesis (Alevizopoulos et al, 1998, *EMBO J.* 17: 5987-5997; Alevizopoulos et al, 2000, *Oncogene* 19: 2067-2074; Deleu et al, 2001, *Oncogene*, 20: 8270-8275; Dorsman et al, 1995, *J Virol* 69: 2962-2967; Fuchs et al, 2001, *Cell* 106: 297-307; Sandmoller et al, 1996, *Mol Cell Biol* 16: 5846-56; Subramanian et al, 1988, *Oncogene* 2: 105-112), our hypothesis would predict a major involvement of the class D gene signature in human cancers.

Example 3

Figures 3A, 3B:
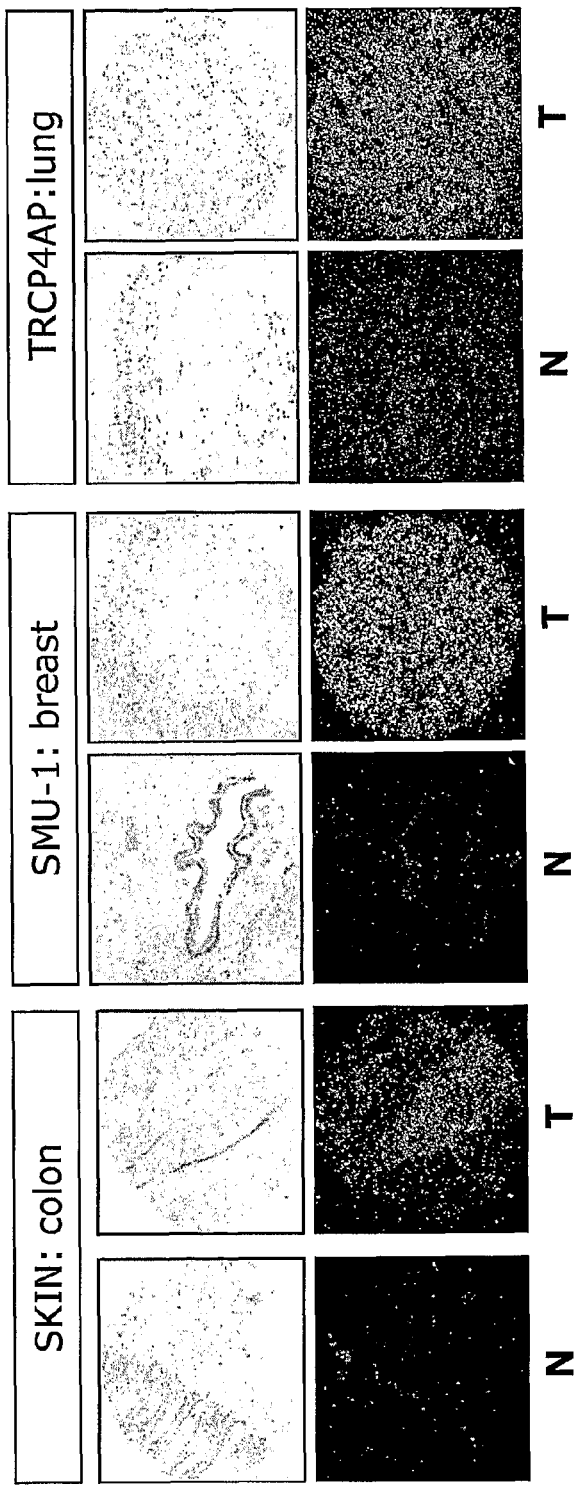
Figure 3C:
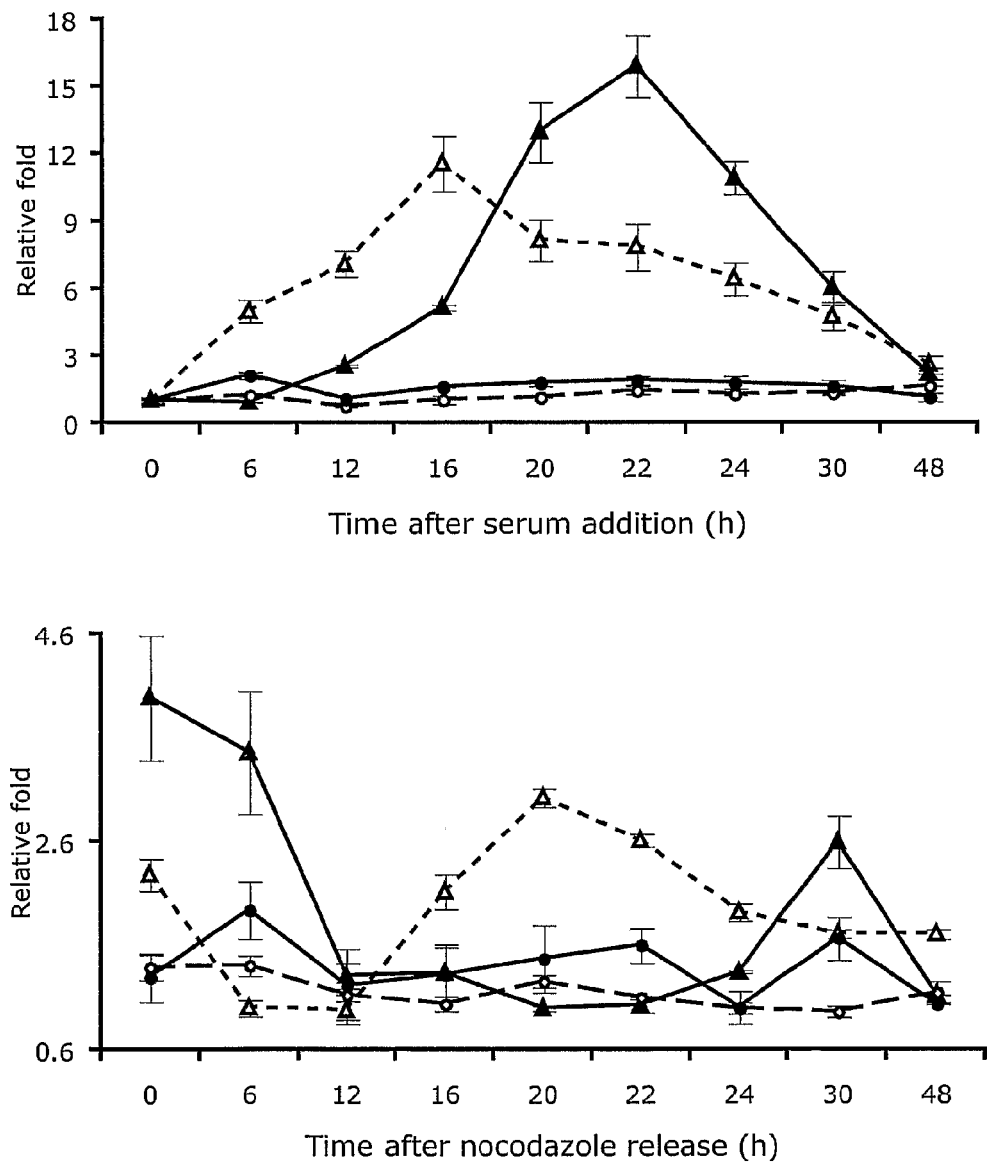

We directly tested this possibility by in situ hybridisation on tissue microarrays (TMA) containing hundreds of tumour samples derived from ten different tumours, along with their matched normal counterparts. Fifteen E1A-induced genes were tested, including representatives from all classes. Strikingly all the six class D genes were overexpressed in a significant fraction of cancers, when compared to normal matched tissues (FIG. 3a). In addition, there was no significant correlation between the tumour proliferative index (as assessed by immunostaining with anti-Ki-67) and the levels of four of six class D genes (SKIN, TRPC4AP, SMU-1 and ch-TOG/KIAA0097), indicating that the overexpression event is not the consequence of the tumour hyperproliferative state (not shown).

This contention was further supported by the finding that four of six class D genes (SKIN, DDX21, TRPC4AP and SMU-1) did not behave as cell-cycle regulated genes, while all the Class-A and class-B genes were cell cycle-regulated, and class C marginally cell cycle-regulated.

Overall, 15 E1A-induced genes, from all classes, were tested by TMA analysis. In particular, LBR, XTP1, MGC22679, KIAA1594, C3Orf4, CML66, FLJ37652 showed low or absent expression in both normal and tumour tissues, indicating that their expression level was below the detection limit of the in situ hybridization technique. Two of the class B genes tested (Np95 and Nasp), showed overexpression in tumours. However, comparably high levels of expression were detected also in the proliferating cells of the normal tissues. Thus Np95 and Nasp cannot be considered truly overexpressed, and their expression probably reflects simply the tumour hyperproliferative state. However, these data do not rule out the possibility that all these genes may still distinguish good and poor prognosis tumour samples using different techniques, especially considering the high proliferative index of very aggressive tumours. Moreover, it is possible that the protein levels of these genes are altered in tumour samples.

Figure 4A:
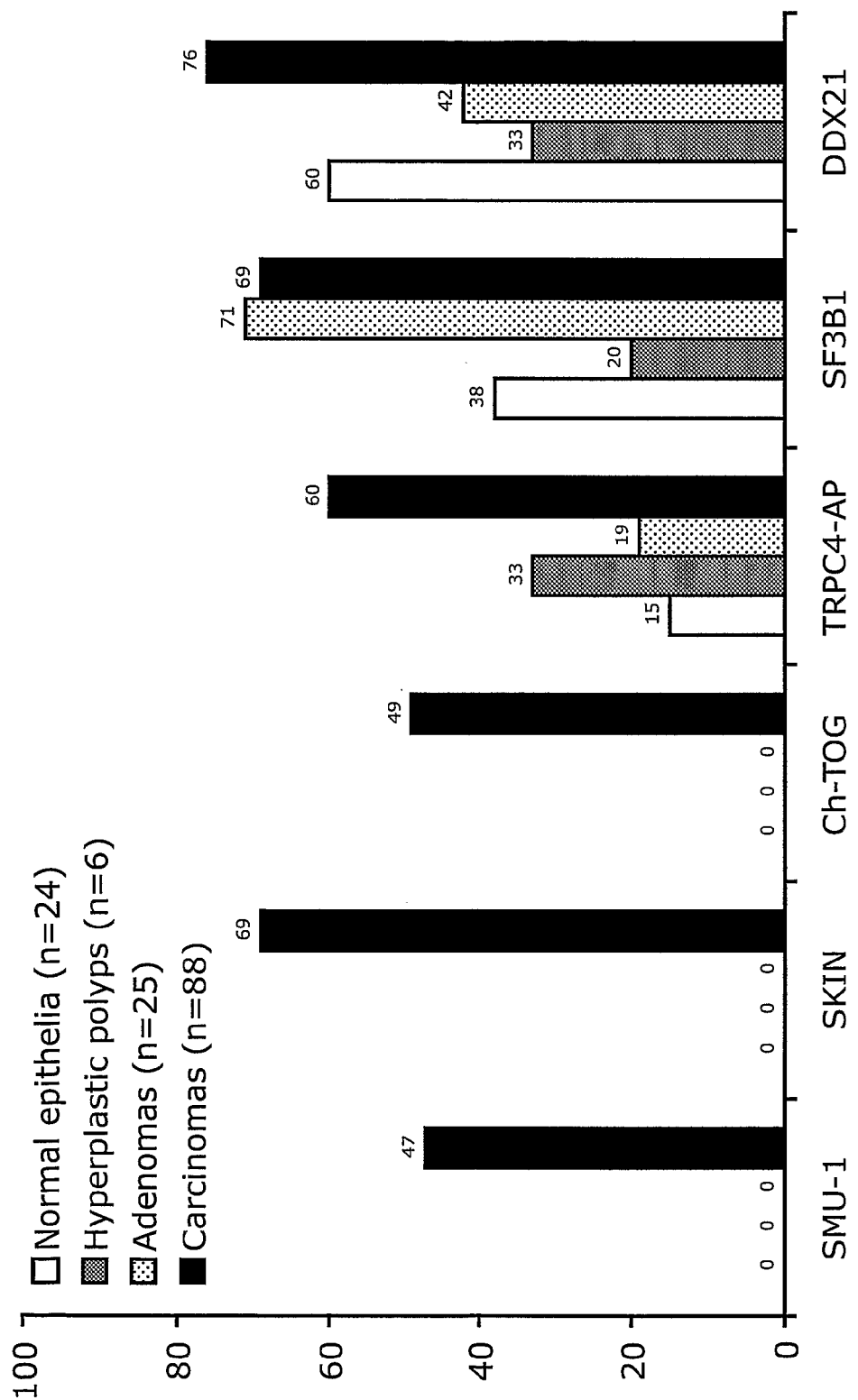
Figure 4B:
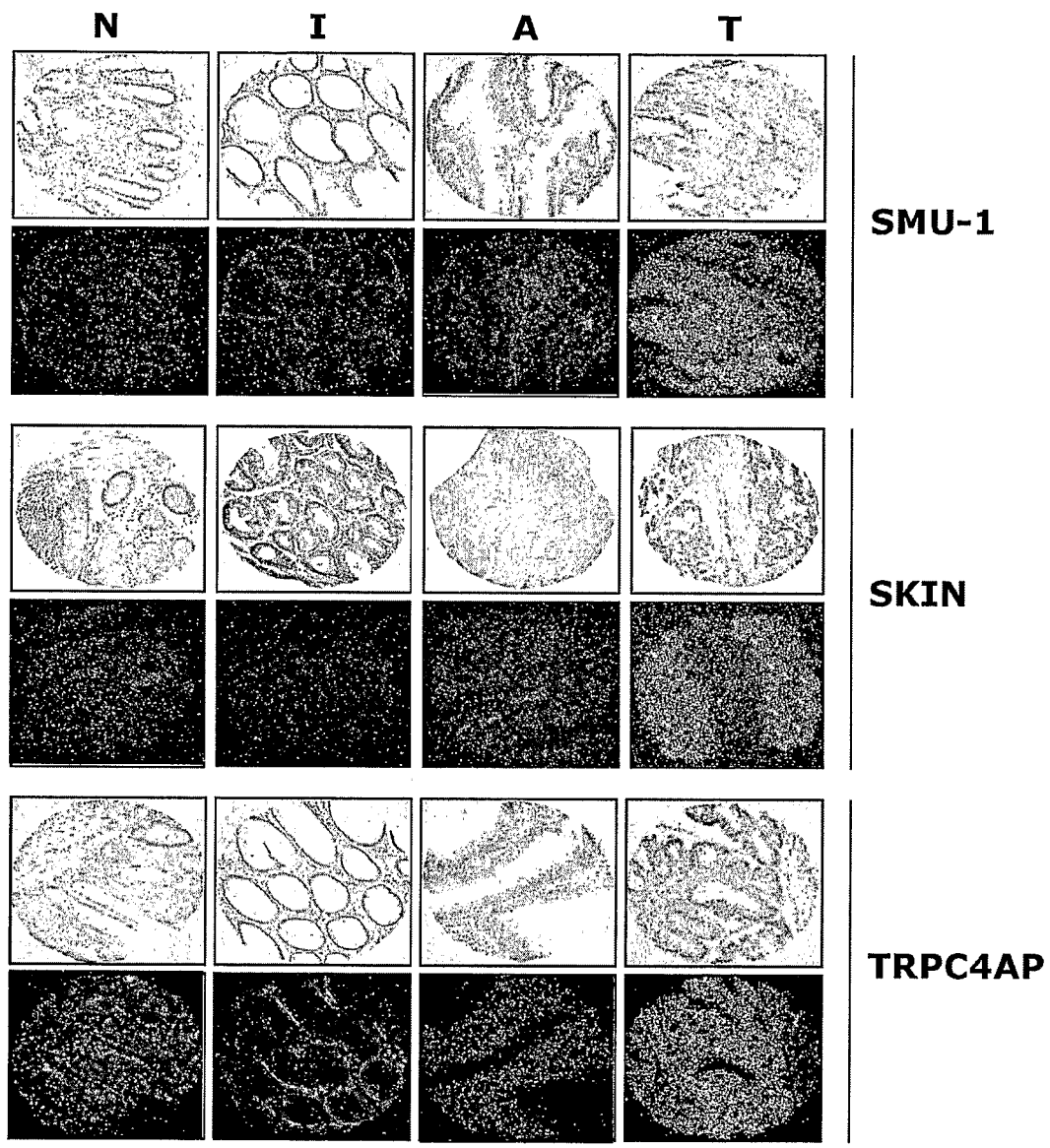
Figure 5A:
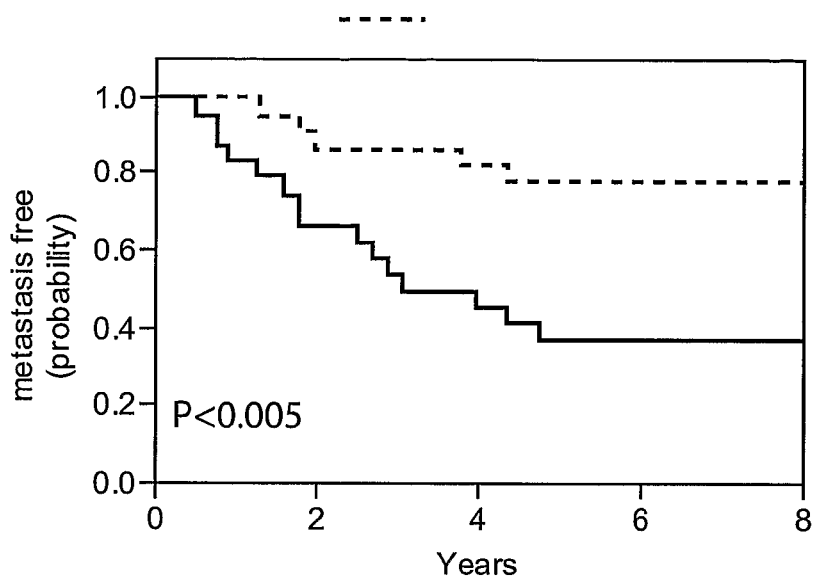
Figure 5B:
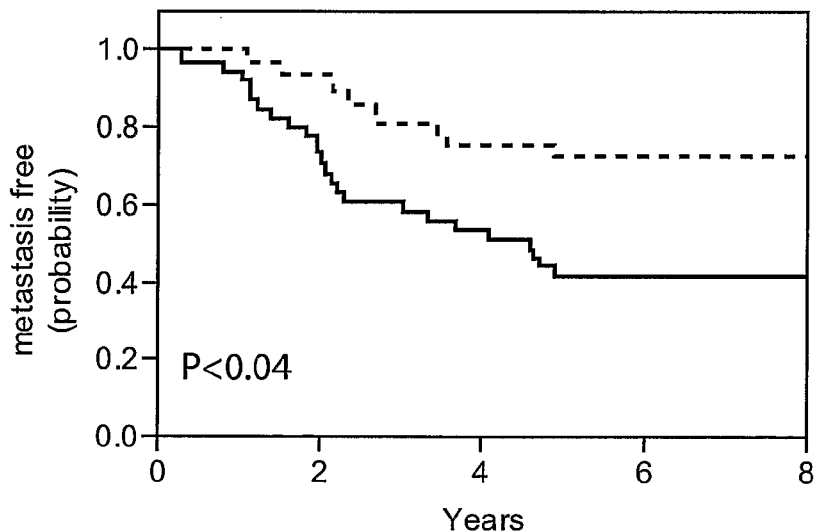
Figure 5C:
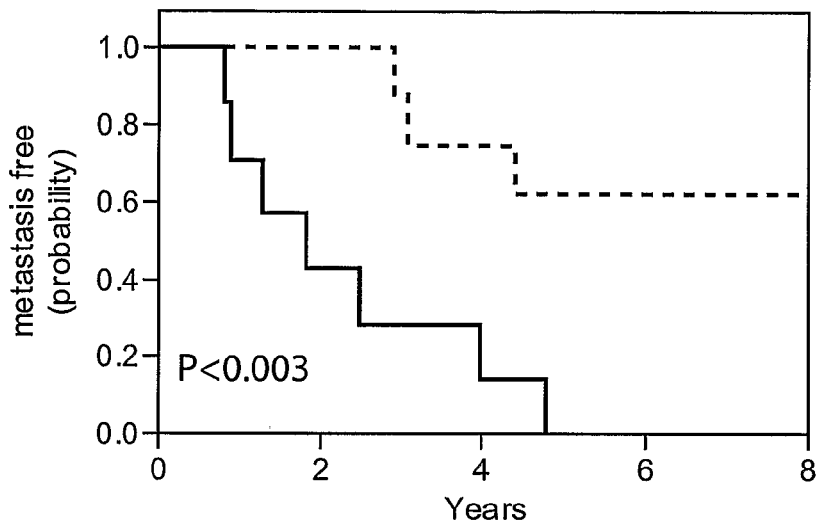
Figure 5D:
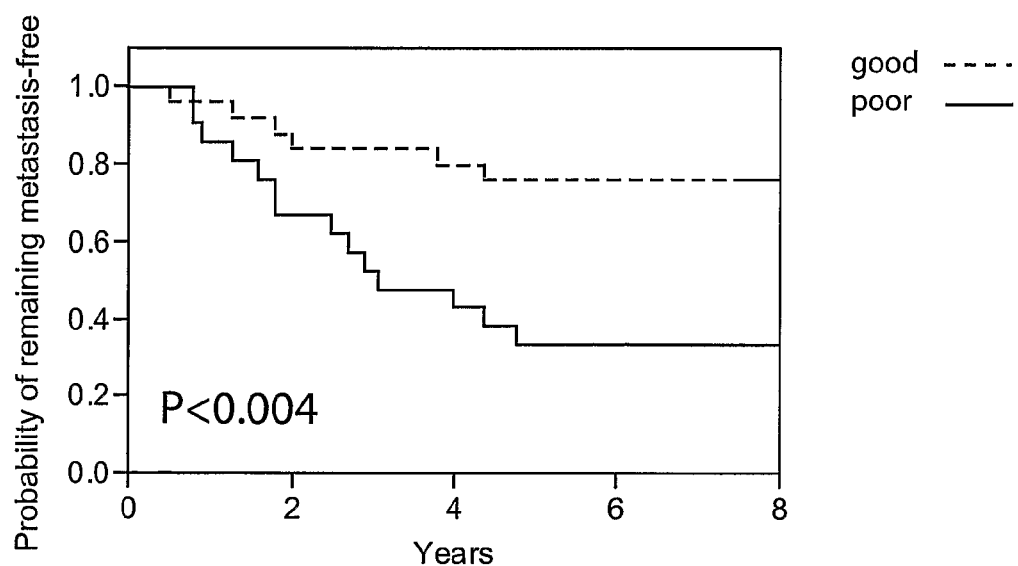

The involvement of the identified cancer signature (class D genes) in the natural history of the tumours was further validated in three sets of experiments. First, we analysed a colon cancer progression TMA containing normal epithelia, hyperplastic polyps, adenomas and adenocarcinomas. All six class D genes were overexpressed in 45-75% of adenocarcinomas. The expression of three genes (SKIN, SMU-1, Ch-TOG/KIAA0097) showed absolute correlation with frank adenocarcinomas (FIG. 4), whereas TRPC4AP was also expressed in other conditions, despite being significantly more expressed in tumours. (FIG. 4). Of note, SF3B1 was also overexpressed in adenomas (FIG. 4), albeit with overall less intense staining than in adenocarcinomas (not shown), consistent with the possibility that its overexpression represents an early event in tumour progression. DDX21 is also overexpressed in adenomas.

Second, we extracted data regarding class D E1A-induced genes from data sets of expression profile screenings performed on a large number of breast samples. Two independent data sets were employed, one published by Van't Veer et al (van't Veer, L. G., et al, 2002, *Nature* 415(31), 530-353) and one generated in-house. In particular, we focused our attention on a subgroup of tumours with no lymph nodes involvement at surgery, which either developed metastatic disease (N0+ patients) or stayed disease-free (N0– patients) over a 5 year follow-up period. Three Class D genes (SKIN, ch-TOG and TRPC4AP) were able to predict the risk of disease relapse with a ~70% accuracy (FIG. 5 A-B).

The Class D genes were able to predict the risk of disease relapse with a p-value<0.05 on the data set generated in-house and a p-value<0.04 on the data set from van't Veer. The predictive strength of the 3-genes model was further confirmed by Q-RT-PCR (p-value 0.003) on 15 randomly selected breast tumor patients (all lymph node negative at diagnosis), which were all homogeneous for estrogen receptor status (Er pos) (FIG. 5 C).

Patients having enhanced expression of ch-TOG and SKIN and a reduced expression of TRPC4AP were designated as having a poor prognosis, whereas patients with a reduced expression of ch-TOG and SKIN and an enhanced expression of TRPC4AP were designated as having a "good" prognosis.

Since the potential use of class A/B/C as prognosis predictors is a viable option, their predictive ability was tested on a subgroup of tumours with no lymph nodes involvement at surgery, which either developed metastatic disease (N0+ patients) or stayed disease-free (N0– patients) over a 5 year follow up period analysed by Affymetrix. Class A+Class B+Class C genes were able to predict the risk of disease relapse (p-value<0.004, FIG. 5D).

Figure 6A:
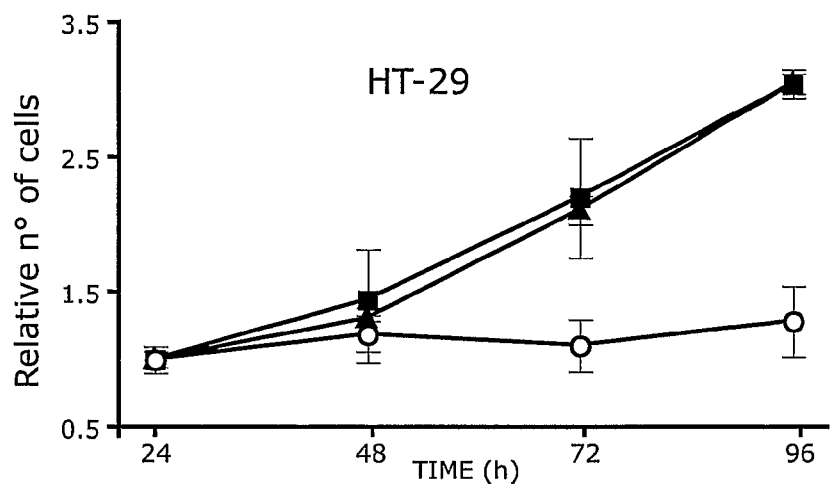
Figure 6A:
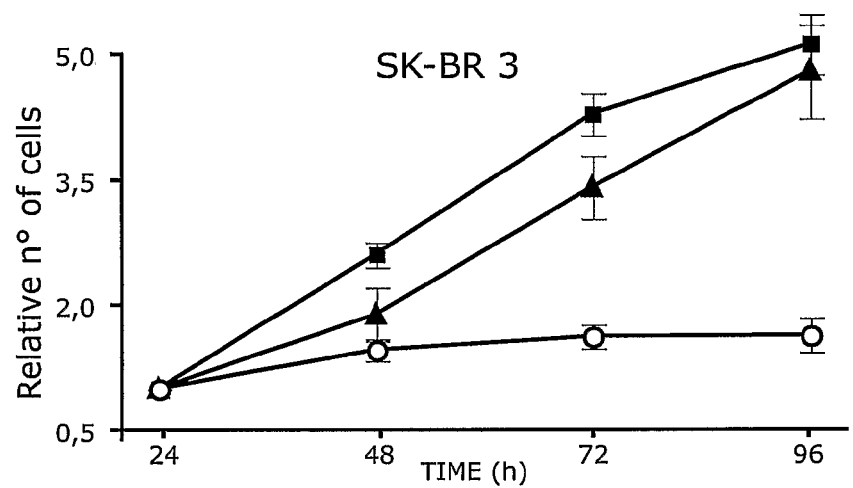
Figure 6A:
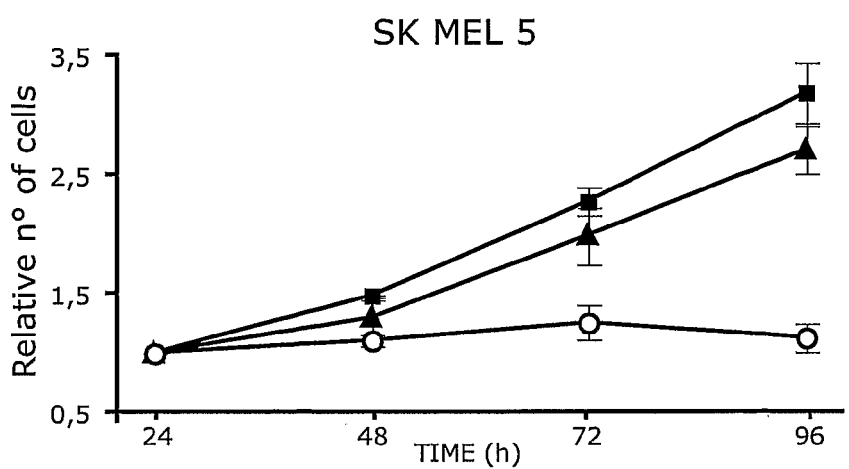
Figure 6A:
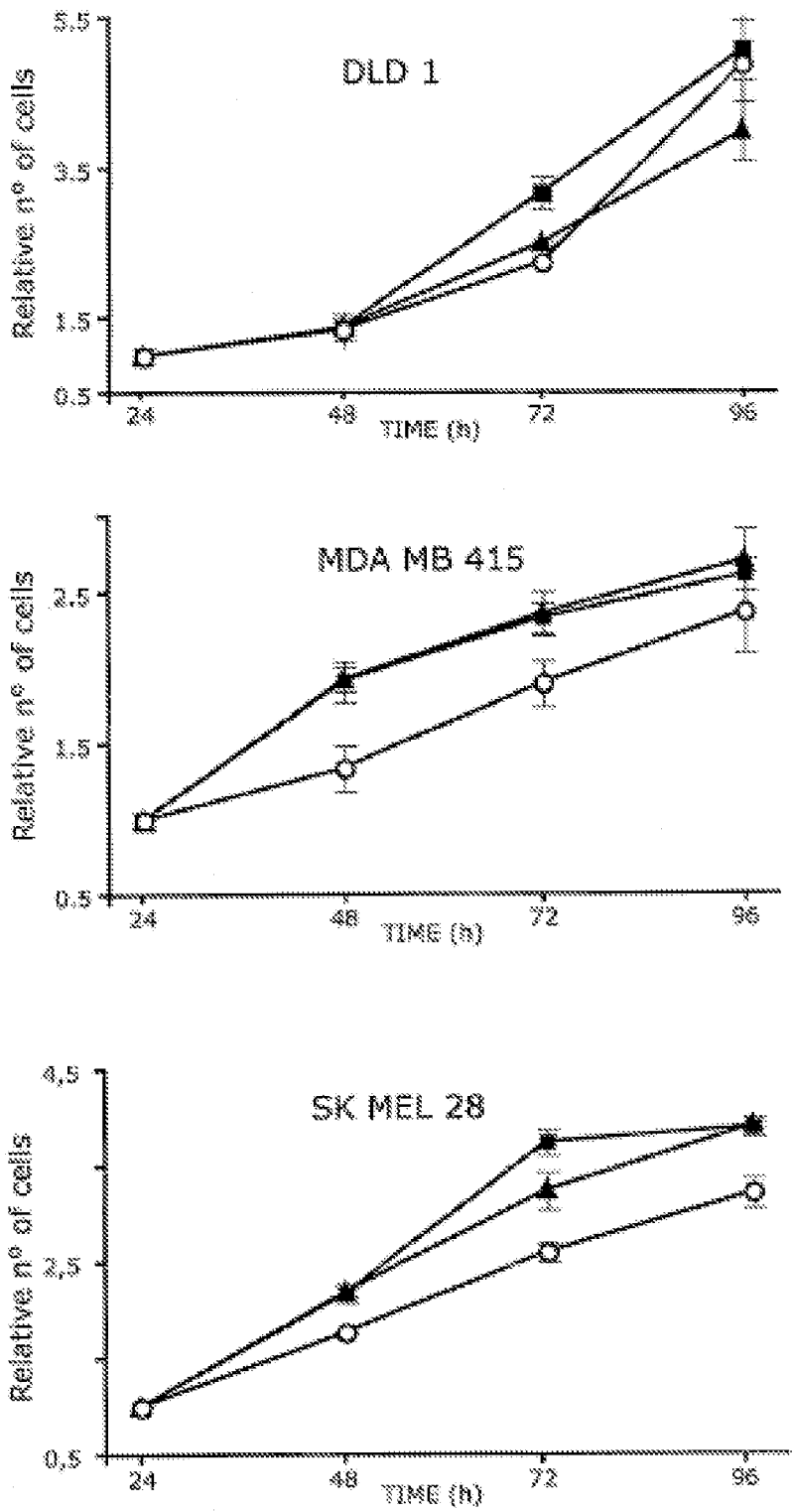
Figure 6B:
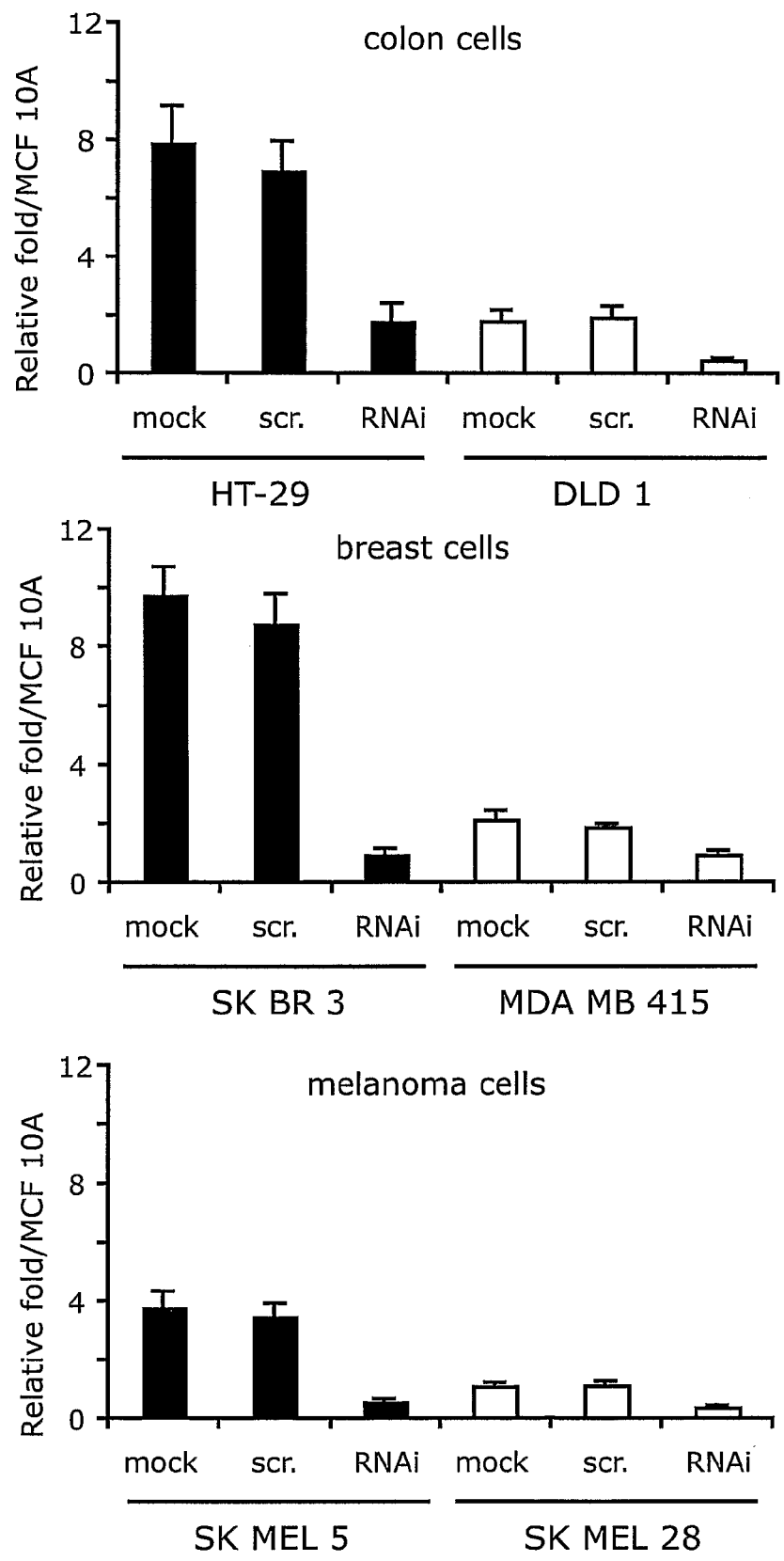
Figure 6C:
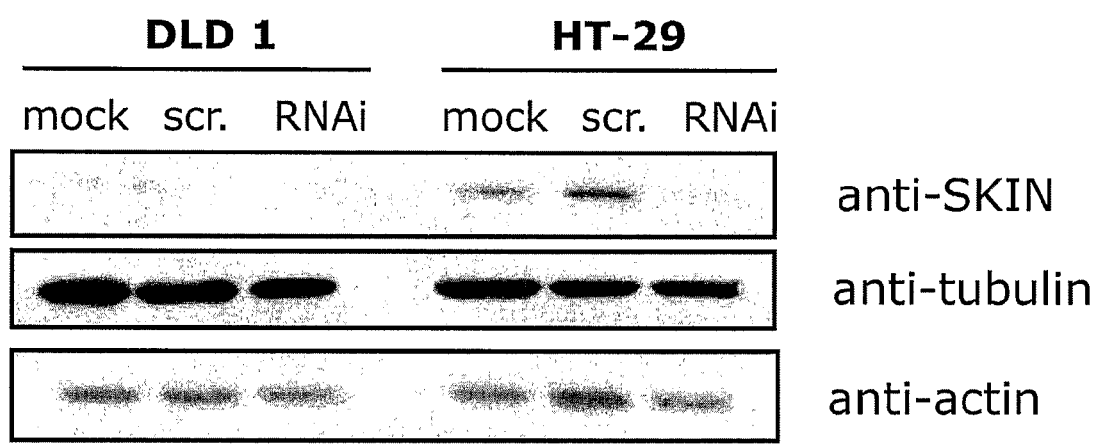

Finally we tested whether class D genes were able to confer a proliferative advantage to tumour cells. As a proof of principle, we focused on the SKIN gene, which showed the most consistent and solid behaviour in all the above described characterizations. The frequent genetic alterations at the SKIN locus predict a mechanistic involvement of this gene in malignant transformation. If so, SKIN overexpression should confer a proliferative advantage to the cell and its functional ablation should revert this phenotype. In order to test this possibility, we selected six cell lines to perform SKIN knock down (KD) by siRNA. Three of the cell lines (HT-29, SKMEL5, and SKBR3) displayed SKIN overexpression (FIG. 6 B-C). Three other tumour cell lines (DLD1, SKMEL28, and MDA-MD415) showed normal levels of SKIN expression (FIG. 6 B-C). Of note, tumour cell lines were selected to represent matched samples (overexpressing/ not overexpressing) from the same type of tumour: colon carcinoma (HT29 and DLD1), melanoma (SKMEL28 and SKMEL5) and breast carcinoma (SKBR3, and MDA-MB-415). As shown in FIG. 6A, the KD of SKIN expression by siRNA dramatically reduced proliferation of all the overexpressing cell lines, whilst a control scrambled oligo had little, if any, effect. Importantly, SKIN KD did not inhibit proliferation of tumour lines displaying no overexpression of SKIN (FIG. 6A).

A survey of cancer microarray data, available in the public domain (oncomie.org), also revealed overexpression of some class-D genes in certain tumours. The results of a meta-analysis regarding class D genes, performed using the ONCOMINE web tool to check for significant regulation of Class-D genes in published expression profile experiments, are shown in FIG. 7. SKIN (flj23790) analysis could not be performed successfully, since the specific probeset for SKIN is present only in some of the more recent array versions (Affymetrix HG-U133 chip B and HG-U95 chip B) therefore drastically reducing the database size. TRPC4AP did not reach statistical significance.

Figures 8A, 8B:
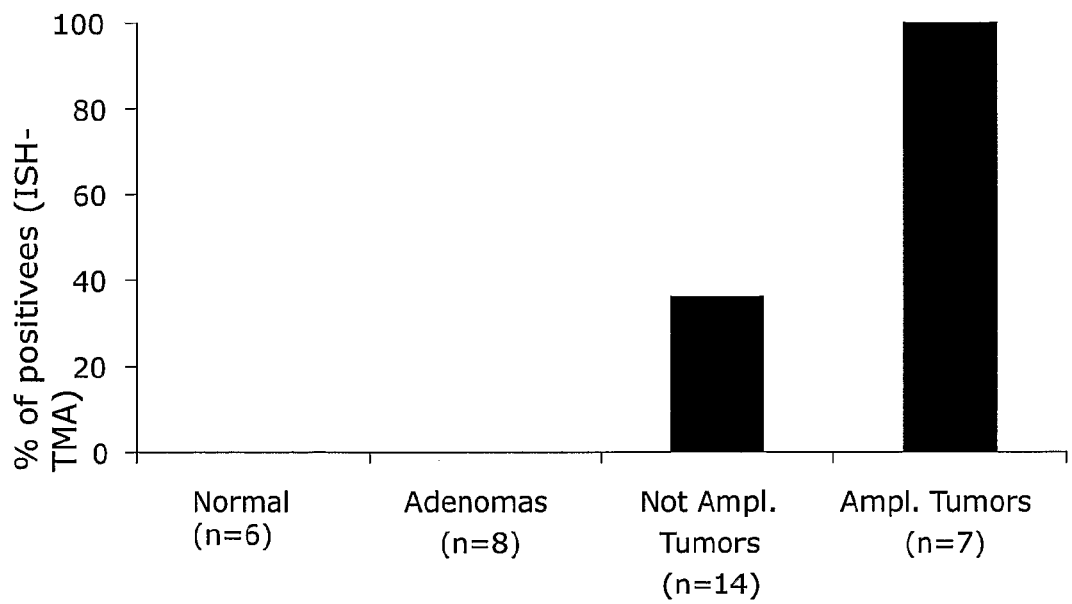
FIG. 8 shows that SKIN is amplified in colon cancers.

FISH Analysis of SKIN was also performed. Genetic alterations at the SKIN locus (on chromosome 8) were sought. Since overexpression is frequently due to increased gene dosage, we focused on SKIN gene amplification. Initially, several cell lines were screened by FISH on metaphase-blocked cells. Multiple SKIN-specific signals were detected in several tumour cells lines (FIG. 8A), independently of their state of aneuploidy. Moreover, SKIN amplification correlated well with its overexpression in the same cell lines, both at mRNA and protein levels, (FIG. 8A). Next, SKIN amplification was analysed directly on tumour tissues by in situ interphase FISH on colon specimens. In 6 samples of normal colonic mucosa and in 8 adenomas, no amplification (and no overexpression, as judged by ISH) of SKIN was detected (FIG. 8B). In colon carcinoma, SKIN amplification (>4 signals/cell) was detected in 7 of 21 cases (33%) (FIG. 8B). Amplification was restricted to the epithelial components of the sample (FIG. 8B). In all cases SKIN amplification was accompanied by overexpression, judged by ISH (FIG. 8B). Interestingly, in a sizable fraction of non-amplified cases (6/14, corresponding to 29% of all analyzed cases), overexpression of SKIN was detected by ISH (FIG. 8 B). Thus, SKIN overexpression can occur in the presence or absence of gene amplification.

Example 4

We conducted a further screen in the same experimental conditions as before (TD C2C12 myotubes infected with either the adenovirus dl520, expressing only the 12S mRNA of E1A, or the control adenovirus dl312, expressing no E1A mRNA). Instead of using a subtraction library technique, RNAs from control/E1A expressing cells were prepared, and profiled by Affymetrix Genechip technology using standard techniques.

1134 genes were identified using this approach (including 25/30 genes obtained in the subtraction screening approach).

From these genes, markers of particular value in the prognosis of breast cancer and NSCLC were identified as below:

Breast Cancer

We used the Affymetrix GeneChip technology (HG-U133 chip A+B) to perform gene expression profiling studies on RNAs prepared from biopsies of an initial group of 46 patients who were estrogen receptor positive with node negative primary carcinomas (N0) at the time of diagnosis, with a >10-year follow up.

This analysis included only patients who developed distant metastases within 5 years (20 cases) and patients presently disease-free (26 cases) after a 7.5-12 years period since the resection of the primary tumour.

The values of expression of more than 30,000 genes for each patient were stored and organised as "breast cancer" dataset, as follows.

The Human Genome U133 (HG-U133) Set, consisting of two GeneChip® arrays, contains almost 45,000 probe sets representing more than 39,000 transcripts derived from approximately 33,000 well-substantiated human genes. This set design uses sequences selected from GenBank®, dbEST, and RefSeq.

The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release). The HG-U133A Array includes representation of the RefSeq database sequences and probe sets related to sequences previously represented on the Human Genome U95Av2 Array. The HG-U133B Array contains primarily probe sets representing EST clusters.

Affymetrix® Microarray Suite version 5.0 was used to normalised and pre-filter the data, with the following procedure:

The detection algorithm of the software was used to calculate a Detection p-value (see Manual for further details) and assign a Present, Marginal, Absent call of the signal for each spot on the array. Features (gene) always called Absent in every arrays were excluded.

The intensity signal of each transcript probed on the array, should be more than 200 (the range of signal is normally between 10 and 20.000) after MASS computing and normalisation.

The median intensity of the signals of all the transcripts probed (probe pairs) on the array was computed (global median) and this value is used to divide again the signal of each probe pair. This procedure is called Chip normalisation.

The median value of a gene probed on different arrays is computed and used to divide the Chip normalised signal of the same gene. This procedure is repeated for every other gene. This is called Gene normalisation.

Having obtained the "breast cancer dataset" as described above, we reduced the initial list of 1134 E1A induced genes by filtering out all those genes showing a fold change <1.5 between the patients who developed metastasis within 5 years, and the patients still free of disease during the long-term follow up.

Then, we ranked the gene list based on their power to correctly classify the patient outcome (poor prognosis Vs. good prognosis) using the leave-one-out cross validation (KNN-9) statistical algorithm, as follows.

The 1134 gene list was reduced to a number of 200 genes, with the following procedure in Genespring 6.2® environment:

1. The class prediction isolates a gene.
2. For each sample, it calculates the probability of obtaining the observed number of samples from each class above and below that cutoff mark by chance, using Fisher's exact test (hypergeometric distribution).
3. Selects the smallest p-value calculated in step 2 and converts it into prediction strength by taking negative natural log of the p-value.
4. Repeats steps 1 to 3 until prediction strengths for all genes on selected gene list are calculated.
5. Ranks the genes according to their predictive strength for each class (200 genes).
6. Genes with highest predictive strength for each class are selected equally to generate a final list of best predictor genes. The final number of best predictors is user-specified (13 genes).

Genespring 6.2® (silicongenetics.com) was used to perform the analyses.

The top ranked 13 genes were then selected, and are shown in the table below.

A significant difference was found in the risk of metastasis in the two groups, using the Log-rank test to calculate P-values.

Using a dataset of 67 patients including those which are both estrogen receptor positive and negative (including the 46 patients previously described) the 13 gene predictor of the present invention is able to identify four more patients which went on to develop metastasis, as compared to the Van't Veer predictor. Using the 46 ER positive patients, it is able to correctly identify 6 more patients as compared to the Van't Veer dataset.

Using the Van't Veer dataset as a test dataset, the percentage of unsuccessfully classified samples has been found to be comparable between the two predictors.

It is important to note that the Van't Veer predictor comprises 70 genes, whereas the present predictor makes use of only 13. The ability to use a smaller set of genes without comprising accuracy is important in the clinical application of the predictor, diminishing costs and allowing a larger range of techniques to be used. Alternatively, more genes could be added to the set to provide a further improvement in accuracy.

The expression profile of the 13 breast gene predictor on 36 N0 breast cancer patients analysed by Affymetrix was further confirmed by Q-RT-PCR. The classifier performance was also confirmed by Q-RT-PCR. Q-RT-PCR reactions were performed using default settings suggested by Applied Biosystem.

Lung Cancer

Two of the most comprehensive NSCLCs screenings, with complete follow up information publicly retrievable (Beer, D. G., et al, 2002. Gene-expression profiles predict survival of patients with lung adenocarcinoma. Nat Med, 8: 816-824, Bhattacharjee, A., et al, 2001. Classification of human lung carcinomas by mRNA expression profiling reveals distinct adenocarcinoma subclasses. Proc Natl Acad Sci USA, 98: 13790-13795) were downloaded from the web (oncomie.org.). These two datasets contain RNA expression val-

TABLE 1

| UGCluster | Name | Symbol | LLID | UGRepAcc | LLRepProtAcc | Cytoband |
|---|---|---|---|---|---|---|
| Hs.444372 | GDNF family receptor alpha 1 | GFRA1 | 2674 | AF038421 | NP_665736 | 10q26 |
| Hs.125180 | growth hormone receptor | GHR | 2690 | NM_000163 | NP_000154 | 5p13-p12 |
| Hs.408182 | collagen, type II, alpha 1 (primary osteoarthritis, spondyloepiphyseal dysplasia, congenital) | COL2A1 | 1280; 4670 | NM_001844 | NP_149162 | 12q13.11-q13.2 |
| Hs.302634 | frizzled homolog 8 (*Drosophila*) | FZD8 | 8325 | AB043703 | NP_114072 | 10p11.22 |
| Hs.408658 | cyclin E2 | CCNE2 | 9134 | NM_057749 | NP_477097 | 8q22.1 |
| Hs.174312 | toll-like receptor 4 | TLR4 | 7099 | NM_003266 | NP_612567 | 9q32-q33 |
| Hs.23900 | Rac GTPase activating protein 1 | RACGAP1 | 29127 | NM_013277 | NP_037409 | 12q13.12 |
| Hs.305971 | solute carrier family 2 (facilitated glucose transporter), member 10 | SLC2A10 | 81031 | AF248053 | NP_110404 | 20q13.1 |
| Hs.165904 | epsin 3 | EPN3 | 55040 | AK000785 | NP_060427 | 17q21.33 |
| Hs.421337 | DEP domain containing 1B | DEPDC1B | 55789 | BC019075; NM_018369 | NP_060839 | 5q12.1 |
| Hs.512638 | TBP-interacting protein | TIP120A | 55832 | NM_018448 | NP_060918 | 12q14 |
| Hs.369055 | ATP-binding cassette, sub-family G (WHITE), member 1 | ABCG1 | 9619 | NM_207630 | NP_997513 | 21q22.3 |
| Hs.409034 | collagen, type XV, alpha 1 | COL15A1 | 1306 | NM_001855 | NP_001846 | 9q21-q22 |

The predictor is able to determine the risk to develop metastasis within 5 years.

Upregulation of one or more genes (e.g., of mRNA levels) in table 1 may be associated with worsening of the prognosis. For each of the 13 genes described herein, mRNA upregulation is associated with a poor prognosis. Patients were considered as having a "good" signature if they had lower values of at least 7 of the 13 genes, compared to other individuals in the sample (the "poor" group).

ues of patients with lung adenocarcinomas from two independent cohorts, and more precisely: the Beer dataset (Affymetrix GeneChip HU6800) is composed by 23 patients with disease-free-survival (DFS) more than 52 months and 18 patients with relapse time (Dead-of-disease) less than 29 months; the Bhattacharjee dataset (Affymetrix GeneChip HG-U95Av2.1) is composed by 33 patients with DFS more than 30 months and 27 with relapse time (Dead-of-disease) less than 25 months.

The datasets were processed as follows:

Affymetrix® Microarray Suite version 4.0 normalised datasets were downloaded from the web.

All the genes and ETSs showing a negative values after normalisation were excluded from further analysis.

We considered only the genes having signal on the chip in at least 25% of the patients in each dataset.

The median value for each gene present on the array was then calculated. We retain all those genes showing a variance of at least 1.5 fold compared to the corresponding median calculated.

The median intensity of the signals of all the transcripts probed (probe pairs) on the array was computed (global median) and this value is used to divide again the signal of each probe pair. This procedure is called Chip normalisation.

The median value of a gene probed on different arrays is computed and used to divide the Chip normalised signal of the same gene. This procedure is repeated for every other gene. This is called Gene normalisation.

The initial 1134 genes list were filtered as previously described (=>1.5 fold change): the two classes of patients considered in this case (as opposed to the breast cancer patients, where we evaluated the propensity to formation of metastatic tumours) are the Dead-of disease group, and the Disease-Free Survival group.

Then, on the filtered list, we ranked the genes according to their ability to discriminate between the two sets of patients, by Univariate t-test (p-value less than 0.05).

We performed the same analyses on both published datasets, and then we selected only the top ranked common genes found on both the datasets.

We repeated the same ranking analysis, but with a more stringent p-value cut-off (<0.001). Thus, we obtained a list of top ranked genes from the merged datasets. At the end, we reduced these lists of genes to a final list of 12 genes (lung predictor) by different Class prediction statistical algorithms (Analyses were performed using BRB ArrayTools).

The genes are shown in table 2, below.

Figure 9A:
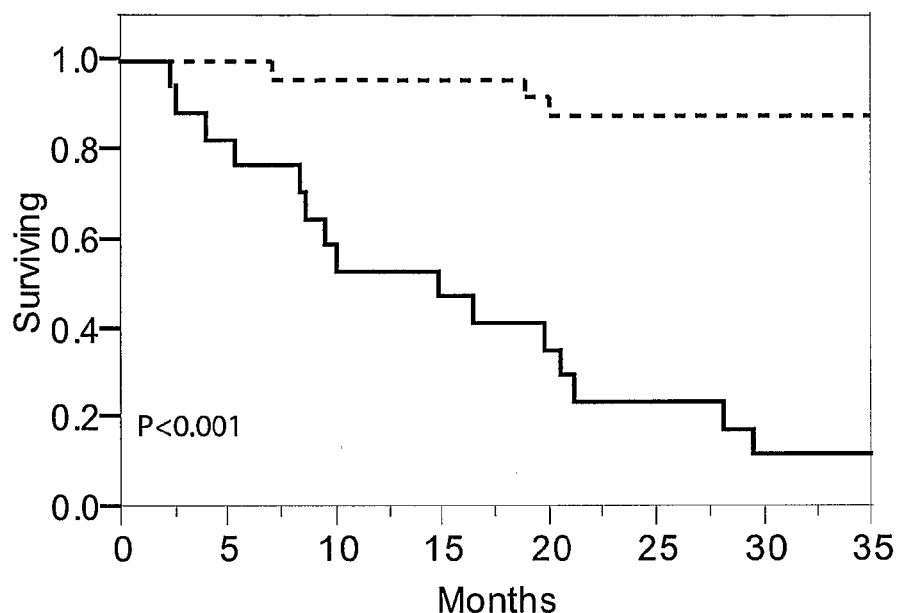
Figure 9B:
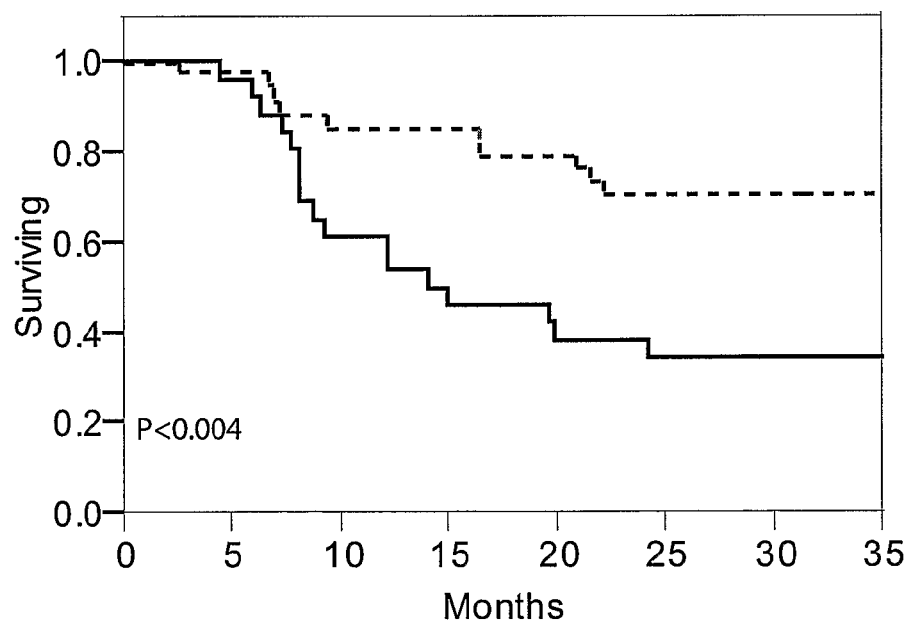
Figure 9C:
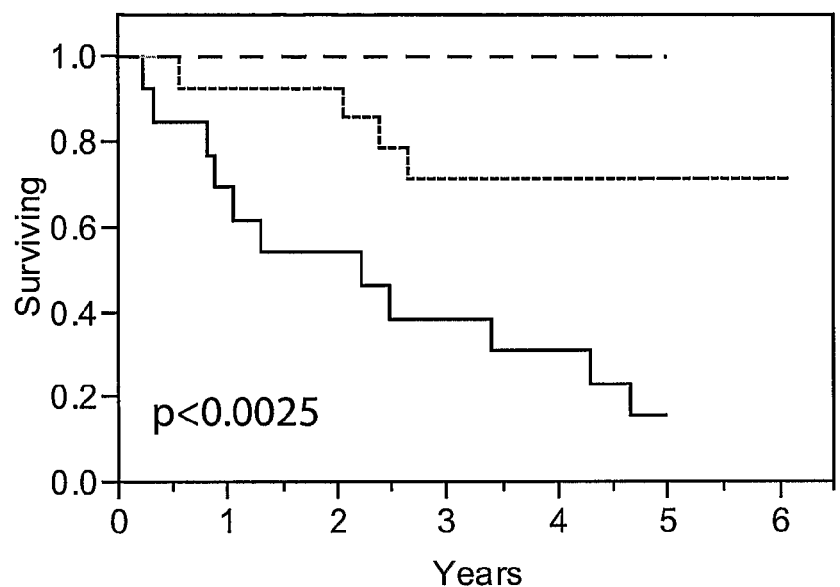
Figure 9D:
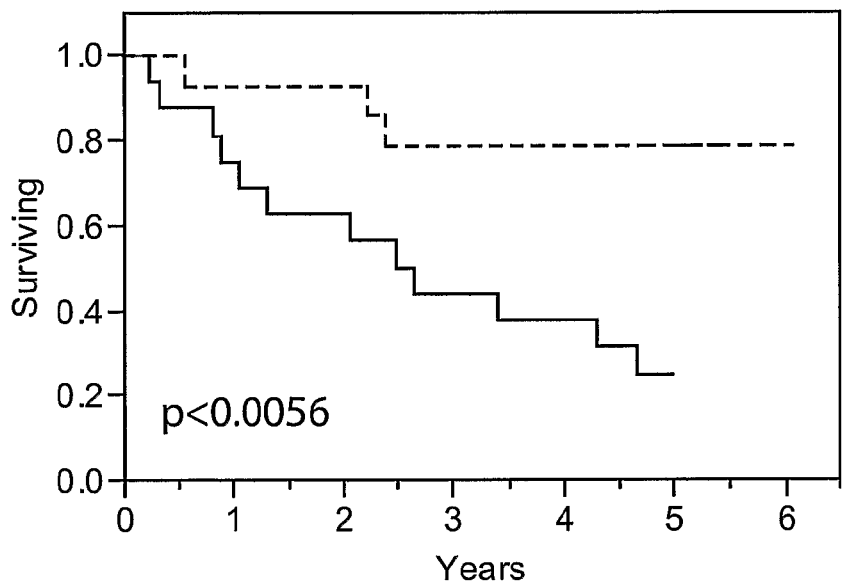

The predictor is able to determine the risk to death within 29 months. FIG. 9 shows the survival probability with a good or poor expression signature based on the NSCLC predictor, using the dataset of Beer et al (FIG. 9A) or the dataset of Bhattacharjee et al (FIG. 9B).

A significant difference was found between the probability of survival of the two groups, using the Log-rank test to calculate P-values.

In respect of table 2, downregulation of HLA-DQB1, LU, GNS, POLR2c, PBXIP1 and RAFTLIN and upregulation of E2F4, PAICS, PFN2, SERPINB5, HSPD1, and ARL4A (e.g., downregulation or upregulation of mRNA respectively) may be associated with a worsening of the prognosis.

In the present example, a good signature was considered to be one which has at least 7 out of the 12 genes (i.e., the majority of genes) which are:

1. For HLA-DQB1, LU, GNS, POLR2c, PBXIP1 and RAFTLIN upregulated compared to other individuals in the analysis (the poor prognosis group);

1. For E2F4, PAICS, PFN2, SERPINB5, HSPD1, and ARL4A downregulated compared to other individuals in the analysis (the poor prognosis group).

The individuals in the analysis were from both of the above datasets.

The expression profile of the 12 lung gene predictor on an independent set of patients composed of 30 tissue specimens (all stage I NSCLC adenocarcinomas) was also evaluated by Q-RT-PCR. The "test" set of patients was composed of 15 patients without evidence of disease (the good outcome group) and 15 patients died of disease (the poor outcome group). The results of the "test" screening confirmed the good performance of our 12 genes classifier (see FIG. 9C).

In addition, in order to test the predictive potential of other candidate genes, the Micro-fluidic Card (Applied Biosystem) technology was employed. Therefore, in this low density array card, in addition to the 12 genes of Table 2, other 38 genes selected from the list of top ranked genes from the merged data sets were also included. The results of the "test" screening showed that a combination of 21 genes (also including 5 of the previously identified 12 genes) (see Table 3 and FIG. 9D) displayed an improved performance in predicting NSCLC patients' outcome. Moreover, the 21 genes predictor appeared to be a novel prognosis predictor also for early stages NSCLC patients (stage I).

TABLE 2

| UGCluster | Name | Symbol | LLID | UGRepAcc | LLRepProtAcc | Cytoband |
|---|---|---|---|---|---|---|
| Hs.108371 | E2F transcription factor 4, p107/p130-binding | E2F4 | 1874 | NM_001950 | NP_001941 | 16q21-q22 |
| Hs.155048 | Lutheran blood group (Auberger b antigen included) | LU | 4059 | BC050450 | NP_005572 | 19q13.2 |
| Hs.245540 | ADP-ribosylation factor-like 4A | ARL4A | 10124 | NM_005738 | NP_997625 | 7p21-p15.3 |
| Hs.334534 | glucosamine (N-acetyl)-6-sulfatase (Sanfilippo disease IIID) | GNS | 2799 | NM_002076 | NP_002067 | 12q14 |
| Hs.409934 | major histocompatibility complex, class II, DQ beta 1 | HLA-DQB1 | 3119 | BM701265 | NP_002114 | 6p21.3 |
| Hs.436432 | raft-linking protein | RAFTLIN | 23180 | NM_015150 | NP_055965 | 3p25.1 |
| Hs.444439 | phosphoribosylaminoimidazole carboxylase, phosphoribosylaminoimidazole succinocarboxamide synthetase | PAICS | 10606 | BX538303 | NP_006443 | 4pter-q21 |
| Hs.505806 | pre-B-cell leukemia transcription factor interacting protein 1 | PBXIP1 | 57326 | NM_020524 | NP_065385 | 1q22 |
| Hs.55279 | serine (or cysteine) proteinase inhibitor, clade B (ovalbumin), member 5 | SERPINB5 | 5268 | BX640597 | NP_002630 | 18q21.3 |
| Hs.79037 | heat shock 60 kDa protein 1 (chaperonin) | HSPD1 | 3329 | BC047350 | NP_955472 | 2q33.1 |
| Hs.79402 | polymerase (RNA) II (DNA directed) polypeptide C, 33 kDa | POLR2C | 5432 | BC003159 | NP_116558 | 16q13-q21 |
| Hs.91747 | profilin 2 | PFN2 | 5217 | BC043646 | NP_444252 | 3q25.1-q25.2 |

TABLE 3

| UGCluster | Name | Symbol | LLID | UGRepAcc | LLRepProtAcc | Cytoband |
|---|---|---|---|---|---|---|
| Hs.96055 | E2F transcription factor 1 | E2F1 | 1869 | BC050369 | NP_005216 | 20q11.2 |
| Hs.438720 | MCM7 minichromosome maintenance deficient 7 (S. cerevisiae) | MCM7 | 4176 | NM_182776 | NP_877577 | 7q21.3-q22.1 |
| Hs.226390 | Ribonucleotide reductase M2 polypeptide | RRM2 | 6241 | AK123010 | NP_001025 | 2p25-p24 |
| Hs.460184 | MCM4 minichromosome maintenance deficient 4 (S. cerevisiae) | MCM4 | 4173 | NM_005914 | NP_877423 | 8q11.2 |
| Hs.444118 | MCM6 minichromosome maintenance deficient 6 (MIS5 homolog, S. pombe) (S. cerevisiae) | MCM6 | 4175 | NM_005915 | NP_005906 | 2q21 |
| Hs.550539 | NudC domain containing 1 | CML66 | 84955 | BC043406 | NP_116258 | 8q23 |
| Hs.471011 | Splicing factor 3b, subunit 1, 155 kDa | SF3B1 | 23451 | NM_012433 | NP_036565 | 2q33.1 |
| Hs.529609 | ATPase type 13A3 | ATP13A3 | 79572 | AJ306929 | NP_078800 | 3q29 |
| Hs.164021 | Chemokine (C—X—C motif) ligand 6 (granulocyte chemotactic protein 2) | CXCL6 | 6372 | BM994397 | NP_002984 | 4q21 |
| Hs.546852 | GA binding protein transcription factor, beta subunit 2, 47 kDa | GABPB2 | 2553 | BC036080 | NP_852092 | 15q21.2 |
| Hs.479728 | glyceraldehyde-3-phosphate dehydrogenase | GAPDH | 2597 | NM_002046 | NP_002037 | 12p13 |
| Hs.404321 | Glycyl-tRNA synthetase | GARS | 2617 | NM_002047 | NP_002038 | 7p15 |
| Hs.436181 | Homeo box B7 | HOXB7 | 3217 | AK223249 | NP_004493 | 17q21.3 |
| Hs.550478 | Heparan sulfate proteoglycan 2 (perlecan) | HSPG2 | 3339 | M85289 | NP_005520 | 1p36.1-p35 |
| Hs.360033 | DNA replication complex GINS protein PSF1 | KIAA0186 | 9837 | XM_375911 | NP_066545 | 20p11.21 |
| Hs.62492 | Secretoglobin, family 3A, member 1 | SCGB3A1 | 92304 | BU607563 | NP_443095 | 5q35-qter |
| Hs.108371 | E2F transcription factor 4, p107/p130-binding | E2F4 | 1874 | NM_001950 | NP_001941 | 16q21-q22 |
| Hs.409934 | major histocompatibility complex, class II, DQ beta 1 | HLA-DQB1 | 3119 | BM701265 | NP_002114 | 6p21.3 |
| Hs.436432 | raft-linking protein | RAFTLIN | 23180 | NM_015150 | NP_055965 | 3p25.1 |
| Hs.55279 | serine (or cysteine) proteinase inhibitor, clade B (ovalbumin), member 5 | SERPINB5 | 5268 | BX640597 | NP_002630 | 18q21.3 |
| Hs.91747 | profilin 2 | PFN2 | 5217 | BC043646 | NP_444252 | 3q25.1-q25.2 |

In respect of table 3, downregulation of HLA-DQB1, SCGB3A1 and RAFTLIN and upregulation of PFN2, SERPINB5, E2F4, E2F1, MCM7, RRM2, MCM4, MCM6, CML66, SF3B1, ATP13A3, CXCL6, GABPB2, GAPDH, GARS, HOXB7, HSPG2 and KIAA0186 (e.g., downregulation or upregulation of mRNA respectively) may be associated with a worsening of the prognosis.

In the present example, a good signature was considered to be one which has at least 11 genes out of the 21 genes (i.e., the majority of genes) which are:

1. For HLA-DQB1, SCGB3A1 and RAFTLIN, upregulated compared to other individuals in the analysis (the poor prognosis group).
2. For PFN2, SERPINB5, E2F4, E2F1, MCM7, RRM2, MCM4, MCM6, CML66, SF3B1, ATP13A3, CXCL6, GABPB2, GAPDH, GARS, HOXB7, HSPG2, KIAA0186 mRNA, downregulated compared to other individuals in the analysis (the poor prognosis group).

Summary

We have validated our initial hypothesis that a biased screening of cancer transcriptomes might lead to the identification of a bona fide cancer signature.

We have shown that a biased method of screening the cancer transciptome, looking at genes whose expression is modulated in response to E1A, can provide a good predictor of cancer progression, providing a significant difference in the risk of cancer progression between patients with a good and with a poor signature.

In respect of the class D genes, the precise molecular knowledge of both the starting and the end points of the identified pathway (E1A and class D genes, respectively) should now allow the identification of the genetic alterations, naturally occurring in a sizable fraction of human cancers, which are predicted to lie in a pathway activated by E1A, but independent of pocket proteins and E2Fs. We note that the interference with distal alterations, in a cancer subverted pathway, might prove rather advantageous for therapeutic purposes. In principle, the interference with an upstream genetic lesion might have undesirable consequences also in normal cells, while the selective intervention on distal branches of a signalling pathway might reduce this possibility, as also supported by the fact that the KD of SKIN specifically inhibited the proliferation of SKIN-overexpressing cells.

Class D genes encode for rather heterogeneous proteins, including proteins involved in RNA splicing (SAP1 and Smu-1), a nucleolar RNA helicase (DDX21), a microtubule-associated protein (Ch-TOG), a component of the TNF-R1 pathway leading to activation of NF-KB (TRPC4AP), and a previously unknown protein displaying no distinguishing dominial feature (SKIN). While this heterogeneity, albeit not surprising in a cancer transcriptional signature, cannot be immediately reconciled in a unifying scenario, we also note that recent results unexpectedly involved ribonuclear complexes containing splicing factors and RNA-binding proteins in cytoskeletal regulation leading to cell adhesion (de Hoog, C. L., et al, 2004, *Cell* 117: 649-662). Thus, it is possible that we have identified a cluster of genes whose regulation is important in determining phenotypes frequently altered in cancer, such as cell adhesion to the substrate and motility.

In additional, we have also shown that other classes of E1A-regulated genes can be used as predictors of the metastatic risk of cancer patients.

Example 5

Methods

Meta-Analysis of Expression Datasets from Microarray Analysis

The "original datasets" included the 86 adenocarcinomas analyzed by Beer et al. [as above, Michigan cohort], and 84 adenocarcinomas selected from a study by Bhattacharjee et al. [as above, the Harvard cohort]. The 84 adenocarcinomas of the Harvard cohort correspond to those selected by Beer et al., for the validation of their prognostic signature. Microarray expression datasets of the Michigan (obtained on the HU6800 Affymetrix chip) and of the Harvard cohorts (obtained on the HU95Av2 Affymetrix chip), and details of patient selection criteria and methods for data normalization can be downloaded from http://dot.ped.med.umich.edu: 2000/ourimage/pub/Lung/index.html.

Patients corresponding to the "original datasets" from the Michigan and Harvard cohorts were divided according to the clinical outcome: patients who died within 30 months were labeled as "bad prognosis"; and patients alive after at least 30 (Harvard cohort) or 50 months (Michigan cohort) were labeled as "good prognosis". Cut-off values were defined so as to obtain a roughly equal number of patients in the good and bad prognosis groups. A number of patients, who did not fit the cut-off criteria were, therefore, excluded from the analysis. This led to the definition of "reduced datasets" (N=41 and 60, for the Michigan and Harvard cohorts, respectively).

Microarray expression datasets of a study by Bild et al. obtained on the HU133 2.0 plus Affymetrix chip [Bild, A. H., Yao, G., Chang, J. T., Wang, Q., Potti, A., Chasse, D., Joshi, M. B., Harpole, D., Lancaster, J. M., Berchuck, A., et al. 2006. Oncogenic pathway signatures in human cancers as a guide to targeted therapies. Nature 439:353-357., the Duke cohort] were downloaded from the authors' webpage (http://data.cgt. duke.edu/oncogene.php). Affymetrix CEL format files were processed using Affymetrix Microarray Suite v.5 software (MAS 5).

Analyses of gene expression data were performed using BRB ArrayTools version 3.3.1 developed by Dr. Richard Simon and Amy Peng Lam. Microarray spot intensities below the minimum value of 10 (the BRB software default for Affymetrix array analysis) were excluded and arrays were then normalized (centered) using the median value of the signal over the entire array. When we derived the 49-gene signature for the Michigan and Harvard reduced datasets, genes were excluded if less than 20% of their expression data across the patients had at least a 1.5-fold change in either direction from the gene's median value. Genes were also excluded if the percentage of data missing or filtered out exceeded 75%. All data were log-transformed (base 2). The two-sample parametric t-test was used to select significant genes.

Class prediction analyses were performed with diagonal linear discriminant analysis (DLDA). We estimated the prediction efficiency of the classifiers using the leave one-out cross-validation, and the p-value of each classifier was evaluated by 2000 random permutations of the patient class labels.

Since data obtained with different microarray platforms were used in our study, the Affymetrix NETAFFX™ web analysis tool was used to match probesets to identical genes (affymetrix.com/analysis/netaffx/index.affx).

Patients and the IFOM Cohort

Clinicopathological data for all patient groups in the present study are below.

TABLE 4

Clinicopathological data

| | Michigan cohort (N = 41) | Harvard cohort (N = 60) | Duke cohort (N = 34) | IFOM Train. cohort (N = 25) | IFOM Val. cohort (N = 45) |
|---|---|---|---|---|---|
| Age - Years | | | | | |
| Median | 60 | 61 | 66 | 64 | 64 |
| Range | 41-80 | 33-88 | 43-83 | 51-72 | 48-81 |
| Mean ± SD | 61 ± 10 | 62 ± 11 | 65 ± 9 | 63 ± 6 | 64 ± 9 |
| Sex - No(%) | | | | | |
| Male | 16 (39) | 26 (43) | 17 (50) | 23 (92) | 41 (91) |
| Female | 25 (61) | 34 (57) | 17 (50) | 2 (8) | 4 (9) |
| Smoking (pack year) - No. (%) | | | | | |
| None | 3 (7) | 3 (5) | | | |
| ≤20 Yr | 5 (12) | 10 (17) | | | |
| 21-49 Yr | 13 (32) | 20 (33) | | | |
| ≥50 Yr | 17 (41) | 27 (45) | | | |
| N.R | 3 (7) | | | | |
| Stage - No. (%) | | | | | |
| I* | | 1 (2) | 4 (12) | | |
| IA | 16 (39) | 15 (25) | 21 (62) | 8 (32) | 13 (29) |
| IB | 12 (29) | 28 (46) | 9 (26) | 17 (68) | 32 (71) |
| IIA | | 2 (3) | | | |
| IIB | | 8 (13) | | | |
| IIIA | 13 (32) | 4 (7) | | | |
| IIIB | | 2 (3) | | | |
| Tumor stage - No. (%) | | | | | |
| 1 | 20 (49) | 19 (32) | 21 (62) | 8 (32) | 13 (29) |
| 2 | 16 (39) | 35 (58) | 9 (26) | 17 (68) | 32 (71) |
| 3 | 5 (12) | 3 (5) | | | |
| 4 | | 2 (3) | | | |
| N.A. | | 1 (2) | 4 (12) | | |

TABLE 4-continued

Clinicopathological data

|  | Michigan cohort (N = 41) | Harvard cohort (N = 60) | Duke cohort (N = 34) | IFOM Train. cohort (N = 25) | IFOM Val. cohort (N = 45) |
|---|---|---|---|---|---|
| Nodal status - No. (%) | | | | | |
| Negative | 28 (68) | 36 (60) | | | |
| Positive | 13 (32) | 12 (20) | | | |
| N.A. | | 12 (20) | | | |

(Data are reported for the patients included in the reduced datasets of the Michigan and Harvard cohorts, and for all patients of the other cohorts. *Tumor stage (A or B) was not available; N.A., not available)

Patients within the IFOM cohorts were selected within a consecutive series of 391 stage I (T1-2NOMO) NSCLC patients surgically treated at the Service of thoracic surgery, University of Pisa between 1994 and 1999. Patient stage at the time of diagnosis was determined according to guidelines of the American Joint Committee on Cancer. The 70 patients selected for this study (25 and 45 for the training and validation cohorts, respectively) were solely selected on the basis of the histotype (adenocarcinoma), availability of adequate tissue samples (>80% tumor cellularity) and complete follow-up data. Informed consent was obtained from all patients under study. Tumors were snap-frozen in liquid nitrogen within 10 minutes of excision and stored at −80° C. Total RNA was isolated with TRIzol (Invitrogen) according to manufacturer's instructions, and its quality was evaluated by gel electrophoresis and by 2100 Bioanalyzer (Agilent).

TaqMan Low Density Array Analysis.

TaqMan® Low Density arrays were purchased from Applied Biosystems. Total RNA (0.5 µg) was reverse transcribed with 200 units of Superscript II RT (Invitrogen) and 250 ng random examers, using manufacturer's instructions. A reaction mix containing 75 ng of cDNA and 50 µl of 2×PCR Master Mix (Euregentec) in a final volume of 100 µl was then prepared and loaded in the array. PCR conditions were as follows: 2 min at 50° C., 10 min at 94.5° C., followed by 45 cycles at 97° C. for 30 s and 59.7° C. for 1 min, on an Applied Biosystems 7900HT PCR System.

The expression level of each gene was measured in triplicate, and a panel of 8 reference genes (RPL14, RPL18, AGPAT1, ACTB, TBP, GUSB, PPIA, 18S) was used. GeNorm software (Vandesompele, J., et al, 2002. *Genome Biol* 3:RESEARCH0034) was used to evaluate the expression stability of the reference genes. The average Ct value of each target gene was normalized against the geometric mean of the Ct values of the 8 reference genes. Universal Reference RNA (Stratagene) was used as calibrator for all the samples analyzed. The relative fold change of gene expression in lung cancer patients was calculated as $2^{-\Delta\Delta Ct}$ ($\Delta\Delta Ct = \Delta Ct_{sample} - \Delta Ct_{univ-ref}$).

Data were then analyzed using BRB ArrayTools version 3.3.1. Definition of the classifier was performed with the diagonal linear discriminant analysis (DLDA) and leave-one-out cross-validation. The p-value was calculated by 2000 random permutations of the class labels. The 45 patients of the IFOM validation cohort were labeled as 'predict' in the BRB ArrayTools, to perform a completely 'blind' classification of the class labels (good and poor outcome). TaqMan® assay IDs (Applied Biosystems) were: NUDCD1/CML66-Hs00292614_m1, CXCL6-Hs00237017_m1, E2F1-Hs00153451_m1, E2F4-Hs00608098_m1, GABPB2-Hs00242573_m1, HLA-DQB1-Hs00409790_m1, HOXB7-Hs00270131_m1, HSPG2-Hs00194179_m1, MCM4-Hs00381533_m1, MCM6-Hs00195504_m1, MCM7-Hs00428518_m1, RAFTLIN-Hs00412084_m1, RRM2-Hs00357247_g1, SCGB3A1-Hs00369360_g1, SERPINB5-Hs00184728_m1, SF3B1-Hs00202782_m1.

Statistical Analysis

Univariate and multivariate analyses were performed using the Nominal Logistic Regression tool within the JMP IN 5.1 software (SAS). The p-values were calculated with the likelihood-ratio Chi-square test. Kaplan-Meier survival curves were generated using JMP IN 5.1 and are based on the DLDA classification results. Kaplan-Meier associated p-values were computed with the log-rank test.

Results

Overall Strategy

A further integrated analysis was undertaken which combined meta-analysis of published microarray expression data and expression profiling of E1A-modulated genes.

Initially, we performed meta-analyses on two published expression datasets of lung adenocarcinomas, including a total of 170 patients, from studies by Beer et al. [as above, henceforth the Michigan cohort] and by Bhattacharjee et al. [as above, henceforth the Harvard cohort].

Patients (see Methods) were divided into good and bad prognosis groups according to their clinical outcome (see Methods for criteria used). A number of patients, who did not fit the established prognostic criteria, were therefore excluded from the meta-analysis. We refer to the datasets from the initial 170 patients as "original datasets" and to those of the selected patients as "reduced datasets"; each of these datasets included patients with stage I, II and III tumours. The two reduced datasets (Michigan and Harvard) were then analyzed to obtain lists of genes that are differentially expressed between good and poor prognosis patients. A third cohort of patients, from an independent study comprising 34 stage I lung adenocarcinomas [Bild, A. H., et al, 2006 *Nature* 439: 353-357, henceforth the "Duke cohort"] was used for validation.

We also used a biased cancer signature of 28 genes, derived from an experimental model that mimics important cancer-related pathways (Nicassio, F., et al, 2005,—*J Clin Invest* 115:3015-3025) and tested/validated its predictive power on the above datasets.

Finally, we combined genes from the two analyses, and tested them in a Real Time PCR-based approach on a fourth cohort of patients (the IFOM cohort), to define a predictive model employing a limited number of genes, and a readily accessible technical platform.

Meta-Analysis of Two Lung Adenocarcinoma Expression Profile Datasets

Initially, we assumed that a reliable list of genes that are differentially regulated in the good vs. bad prognosis group, should be concomitantly found in independent analyses of the Michigan and Harvard datasets. Therefore, we performed a class comparison test and we identified 361 unique differentially expressed genes (p<0.05, parametric t-test) in the Michigan cohort, and 429 unique differentially expressed genes (p<0.05, parametric t-test) in the Harvard cohort. Twenty genes were shared between the two lists (p<0.05, parametric t-test).

In an alternative approach, we assumed that a reliable list of genes should not necessarily be shared by the two independent analyses. Hence, we searched for the most stably differentially expressed genes in each dataset, using a stringent p-value cut-off (p<0.001, parametric t-test). We found 21 unique genes in the Michigan cohort, and 12 unique genes in the Harvard cohort, for a total of 33 unique genes. In total, by combining the two approaches, we identified 49 unique genes (4 were common to both the Michigan and Harvard cohorts), which we refer to as the "49-gene model". The 49 genes are listed in table 8, source identified as "meta", and are shown separately in table 8b.

Next, we analyzed the prognostic predictive accuracy of the 49-gene model with the use of leave-one-out cross-validation (Table 5). Predictive accuracy on the "reduced datasets" was 90% and 72% on the Michigan and Harvard cohorts, respectively (Table 5). On the "original datasets", predictive accuracy was 69% and 71% on the Michigan and Harvard cohorts, respectively (Table 5). Of note, the 49-gene model performed well when compared with two signatures (of 50 and 100 genes, respectively) derived by Beer et al. from the Michigan cohort (Beer, D. G., et al, 2002, *Nat Med* 8:816-824). Our model was however more stable when analyzed on the Harvard cohort, as expected since it was derived from meta-analysis of both the Michigan and Harvard datasets (Table 5; see also table 6 for additional controls and analyses).

TABLE 5

Prognostic predictive accuracy of the 49-gene model.

Reduced Datasets

| Model | Michigan cohort N = 41 | | | Harvard cohort N = 60 | | |
|---|---|---|---|---|---|---|
| | Acc. (%) | Sen. (%) | Spec. (%) | Acc. (%) | Sen. (%) | Spec. (%) |
| 49-Gene | 90 | 89 | 91 | 72 | 67 | 76 |
| 50-gene | 73 | 50 | 91 | 63 | 67 | 61 |
| 100-gene | 80 | 72 | 87 | 63 | 59 | 67 |

Original datasets

| Model | Michigan cohort N = 86 | | | Harvard cohort N = 84 | | | Duke cohort N = 34 | | |
|---|---|---|---|---|---|---|---|---|---|
| | Acc. (%) | Sen. (%) | Spec. (%) | Acc. (%) | Sen. (%) | Spec. (%) | Acc. (%) | Sen. (%) | Spec. (%) |
| 49-gene | 69 | 67 | 69 | 71 | 71 | 72 | 82 | 93 | 74 |
| 50-gene | 81 | 58 | 90 | 60 | 60 | 58 | 74 | 80 | 69 |
| 100-gene | 81 | 75 | 84 | 58 | 63 | 53 | 76 | 80 | 74 |

Table 5: The 49-gene model was tested for prognostic predictive accuracy by leave-one-out cross-validation. Two other models of 50 and 100 genes, respectively, from Beer et al. (as above) were tested, as a comparison. Models were tested on the reduced datasets (top) and on the original datasets (bottom) from the Michigan, Harvard, and Duke cohorts (N, number of patients in the dataset).

Accuracy (Acc.), percentage of correctly predicted patients; sensitivity (Sen.), probability for a patient with poor prognosis to be predicted as with poor prognosis; specificity (Spec.), probability for a patient with good prognosis to be predicted as with good prognosis.

TABLE 6

Modified Reduced Datasets

| Model | Michigan cohort N = 66 | | | Harvard cohort N = 61 | | |
|---|---|---|---|---|---|---|
| | Accuracy (%) | Sensitivity (%) | Specificity (%) | Accuracy (%) | Sensitivity (%) | Specificity (%) |
| 49-gene | 79 | 83 | 77 | 74 | 70 | 77 |
| 50-gene | 85 | 56 | 96 | 67 | 67 | 68 |
| 100-gene | 83 | 72 | 88 | 64 | 56 | 71 |
| 71-gene | 85 | 83 | 85 | 74 | 67 | 79 |

Reduced Datasets

| Model | Michigan cohort N = 41 | | | Harvard cohort N = 60 | | |
|---|---|---|---|---|---|---|
| | Accuracy (%) | Sensitivity (%) | Specificity (%) | Accuracy (%) | Sensitivity (%) | Specificity (%) |
| 49-gene | 90 | 89 | 91 | 72 | 67 | 76 |
| 50-gene | 73 | 50 | 91 | 63 | 67 | 61 |
| 100-gene | 80 | 72 | 87 | 63 | 59 | 67 |
| 71-gene | 85 | 83 | 87 | 73 | 67 | 79 |

Original datasets

| Model | Michigan cohort N = 86 | | | Harvard cohort N = 84 | | | Duke cohort N = 34 | | |
|---|---|---|---|---|---|---|---|---|---|
| | Acc. (%) | Sen. (%) | Spec. (%) | Acc. (%) | Sen. (%) | Spec. (%) | Acc. (%) | Sen. (%) | Spec. (%) |
| 49-gene | 69 | 67 | 69 | 71 | 71 | 72 | 82 | 93 | 74 |
| 50-gene | 81 | 58 | 90 | 60 | 60 | 58 | 74 | 80 | 69 |
| 100-gene | 81 | 75 | 84 | 58 | 63 | 53 | 76 | 80 | 74 |
| 71-gene | 73 | 67 | 76 | 69 | 69 | 69 | 82 | 93 | 74 |

Table 6: In this Table, an additional control is shown, obtained by changing the cut-off criteria to define the good and bad prognosis groups. By changing the labeling criteria to: bad prognosis = death <30 months, good prognosis = alive >15 months (in both cohorts of patients), we obtained what is defined here as the "modified reduced datasets" These datasets, which included more patients than the "reduced datasets" (as defined in the methods section above), were subjected to meta-analysis, with a dual strategy identical to that described for the "reduced datasets" above. This led to the identification of a 71-gene prognostic signature (which shares 23 genes with the 49-gene signature). The performance of the 71-gene model in the leave-one-out cross-validation is shown here, in comparison to the 49-gene model and to the 50-and 100-gene models from Beer et al. (as above), for the modified reduced datasets, the reduced datasets, and the original datasets. As shown, the 71-gene model did not perform better than the 49-gene model, despite containing 22 additional genes.

Figure 13B:
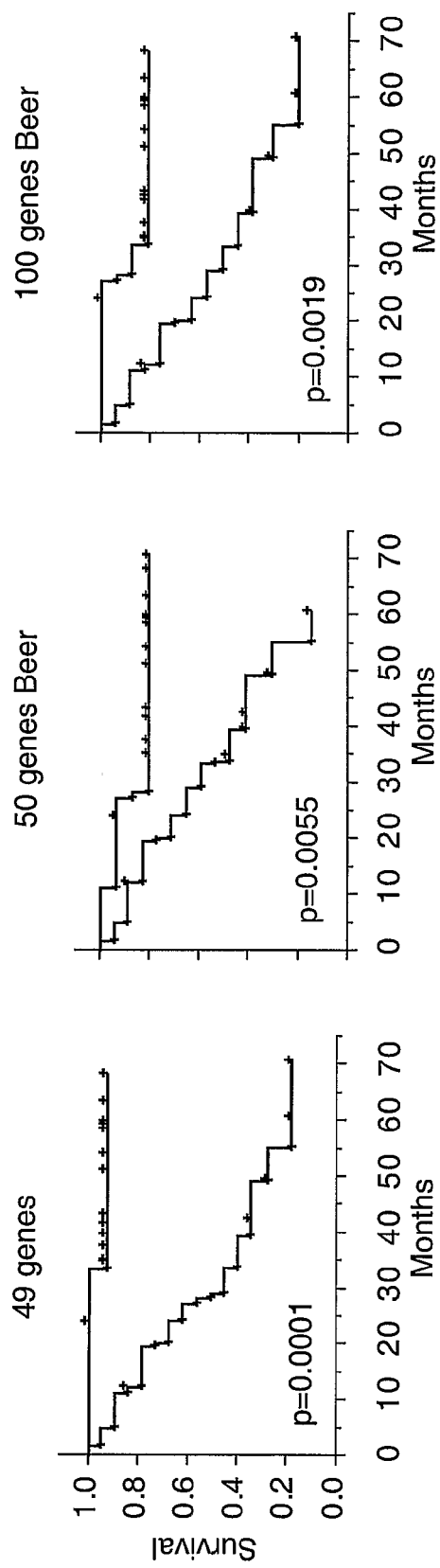

Finally, the performance of the 49-gene model was tested by Kaplan-Meier analysis on stage I adenocarcinomas (FIG. 10). The 49-gene model was very effective in predicting overall survival in the stage I patients both from the Michigan and Harvard cohorts (FIG. 10 and FIG. 13). In addition, when a dataset from a third independent expression profile study [the "Duke cohort"] was tested, the 49-gene model proved remarkably effective in predicting prognosis (Table 5, and table 6), and overall survival (FIG. 10, and FIG. 13). It is of note that the 49-gene model performed better that the 50- and 100-gene models (Beer et al) both in the prediction of prognosis (Table 5) and of overall survival (FIG. 13B), when tested on the Duke cohort, which might be considered as a validation cohort for the three models.

Analysis in Lung Adenocarcinoma of an In Vitro Derived Transcriptional Signature We have previously shown that a biased approach to cancer transcriptomes can lead to the identification of cancer signatures. In particular, a 28-gene biased signature was identified by profiling terminally differentiated myotubes forced to re-entry the cell cycle by the viral oncoprotein E1A. The expression of genes from this signature was frequently found to be altered in human neoplasia (Nicassio, F., et al, 2005, *J Chin*

*Invest* 115:3015-3025). Thus, we investigated whether the expression of these genes had predictive value in patient with stage I lung adenocarcinomas. We employed the data set from the Duke cohort, since it was the only one for which the expression data for all 28 of our genes was available. The 28 genes are identified in table 8 as having source "E1A" and are shown separately in table 8a.

Figure 11A:
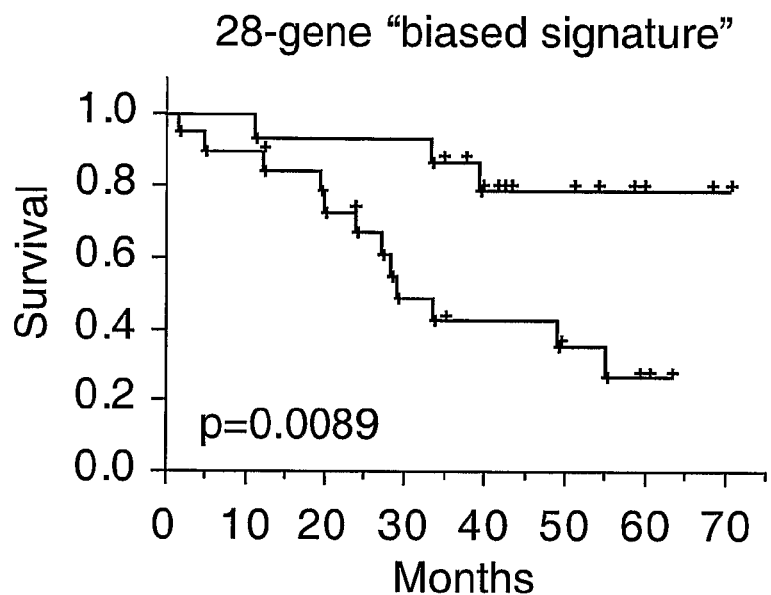

As shown in FIG. 11A, the biased signature could effectively predict overall survival, further confirming that a biased approach can lead to the discovery of cancer-relevant signatures (see also table 7, below).

significant regulation was found in the 5 genes present in the Stage I lung adenocarcinomas in the Michigan cohort, whereas, in the Duke cohort 15 of 28 genes were significantly regulated in the unfavorable prognosis vs. the good prognosis group.

A 10-Gene Prognostic Model in Stage I Lung Adenocarcinomas

The next step in our experimental approach was to integrate models derived from unbiased and biased screenings. Thus, we combined the 49-gene model and the 28-gene biased signature. We also added 3 genes (SCGB3A1, TERT,

TABLE 7

Differential expression of genes of the 28-gene biased signature in Stage I lung adenocarcinomas.

| Symbol/Gene | Probe set | FOLD RATIO tumor/normal | p-value | Acc. |
|---|---|---|---|---|
| *Michigan study* | | | | |
| NASP | m97856_at | 1.33 | 0.0105 | AY700118 |
| RRM2 | x59618_at | 4.93 | 0.0032 | AK123010 |
| E2F1 | s49592_s_at | 1.57 | <0.0001 | BC050369 |
| MCM4 | x74794_at | 2.11 | <0.0001 | NM_005914 |
| *Harvard study* | | | | |
| NASP | 33255_at | 1.37 | 0.0412 | AY700118 |
| G3BP2 | 35793_at | 1.20 | 0.0185 | NM_203505 |
| SF3BP1 | 39444_at | 2.02 | 0.0097 | NM_012433 |
| MCM4 | 981_at | 3.96 | 0.0003 | NM_005914 |
| CCNE2 | 35249_at | 3.87 | 0.0002 | NM_057749 |
| RRM2 | 36922_at | 4.17 | <0.0001 | AK123010 |
| MCM6 | 40117_at | 1.89 | <0.0001 | NM_005915 |

| Symbol/Gene | Probe set | FOLD RATIO bad/good | p-value | Acc |
|---|---|---|---|---|
| *Harvard study* | | | | |
| MCM6 | 40117_at | 1.44 | 0.0011 | NM_005915 |
| MCM7 | 947_at | 1.38 | 0.0080 | NM_182776 |
| *Duke study* | | | | |
| USP37/KIAA1594 | 226729_at | 1.72 | 0.0012 | BX538024 |
| RRM2 | 201890_at | 2.13 | 0.0028 | AK123010 |
| FLJ37562 | 1553108_at | 1.97 | 0.0032 | BC053677 |
| MCM7 | 210983_s_at | 1.93 | 0.0071 | NM_182776 |
| MCM4 | 222036_s_at | 2.63 | 0.0076 | NM_005914 |
| G3BP2 | 208841_s_at | 1.39 | 0.0160 | NM_203505 |
| SF3B1 | 201071_x_at | 1.26 | 0.0172 | NM_012433 |
| FAM91A1/FLJ23790/SKIN | 226294_x_at | 1.43 | 0.0187 | AL832999 |
| UHRF1 | 225655_at | 1.95 | 0.0216 | AB177623 |
| HAT1 | 203138_at | 1.79 | 0.0227 | AK127840 |
| TRPC4AP | 212059_s_at | 1.25 | 0.0277 | AL096738 |
| C3orf4 | 239146_at | 0.73 | 0.0351 | BX647535 |
| SYNCRIP/NSAP1 | 217832_at | 1.33 | 0.0352 | AB209098 |
| CKAP5/Ch-TOG | 1555278_a_at | 1.44 | 0.0374 | NM_001008938 |
| SCC-112/KIAA0648 | 212138_at | 1.28 | 0.0428 | BC114218 |

Table 7: These data are supplemental to those shown in FIG. 11A. Since datasets from the Michigan, Harvard and Duke studies were obtained on different generations of chips, not all of the 28 genes of the biased signature were present on the chips. In particular, only 5 and 11 genes of 28 were present on the chips used in the Michigan and Harvard studies, respectively. This prevented Kaplan-Meyer analysis on the Michigan and Harvard cohorts, which, on the other hand, could be meaningfully performed on the Duke cohorts, since all the 28 genes were present in the datasets (see FIG. 11A).

However, as shown in this Table (top), 4 of 5 genes, and 7 of 11 genes, were significantly overexpressed in tumor vs. normal tissues in the Michigan and Harvard study, respectively (it was not possible to perform the same analysis on the Duke datasets since no information were present as to expression levels in normal lungs).

Figure 11B:
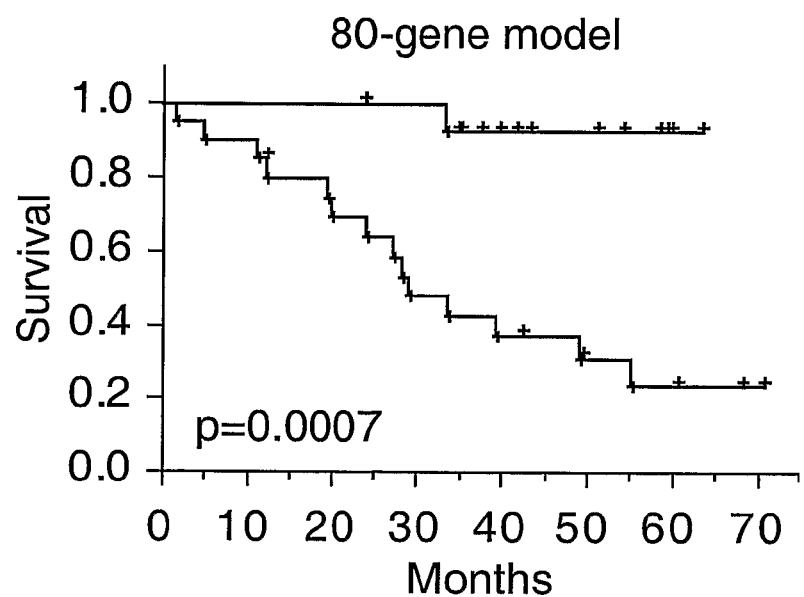

In addition (bottom part of the Table), in the Harvard cohort, 2 of 11 genes were significantly regulated in the comparison between good and bad prognosis patients. No EIF3S6) identified in the literature as individual prognostic markers for stage I lung adenocarcinoma (Buttitta, F. et al, 2005, *Clin Cancer Res* 11:3198-3204, Wang, L., et al, 2002, *Clin Cancer Res* 8:2883-2889, Marchetti, A., et al, 2004, *Clin Cancer Res* 10:1338-1343). This set of 80 genes demonstrated excellent predictive power for overall patient survival in Kaplan-Meyer analysis of the Duke cohort (the only one for which expression data for all 80 genes are available) (FIG. 11b and Table 8).

TABLE 8

Analysis of the 80-gene model in the, Michigan, Harvard and Duke cohort and in the IFOM training cohort.

| | | | | MICH. cohort | | HARV. cohort | | DUKE cohort | | IFOM cohort | | |
|---|---|---|---|---|---|---|---|---|---|---|---|---|
| Symbol | Gene | Acc | Source | FOLD RATIO | p-value | FOLD RATIO | p-value | FOLD | p-value | FOLD RATIO | p-value | TREND |
| SCGB3A1* | SCGB3A1 | BM921624 | Liter. | | | | | 0.48 | 0.314 | 0.03 | <0.001 | DOWN |
| †EIF3S6 | †EIF3S6 | AK124178 | Liter. | | | | | 1.28 | 0.087 | 1.38 | 0.425 | UP |
| †TERT | †TERT | AF018167 | Liter. | | | | | 1.31 | 0.126 | ND | ND | UP |
| BAT1 | BAT1 | AK127767 | E1A | | | | | 1.26 | 0.085 | | | UP |
| CLDND1 | C3orf4 | BX647535 | E1A | | | | | 0.73 | 0.035 | | | UP |
| CCNE1 | CCNE1 | BC035498 | E1A | | | | | 1.24 | 0.432 | 0.94 | 0.84 | UP |
| CCNE2 | CCNE2 | NM_057749 | E1A | | | 1.22 | 0.364 | 1.13 | 0.59 | 0.78 | 0.543 | UP |
| CKAP5 | ch-TOG | NM_001008938 | E1A | | | | | 1.44 | 0.037 | 1.03 | 0.988 | UP |
| DEPDC1B | XTP1 | BC019075 | E1A | | | | | 0.74 | 0.173 | | | UP |
| E2F1* | E2F1 | BC050369 | E1A | 1.01 | 0.949 | 1.12 | 0.060 | 1.17 | 0.288 | 1.79 | 0.012 | UP |
| FAM91A1 | FLJ23790/SKIN | AL832999 | E1A | | | | | 1.43 | 0.019 | 1.13 | 0.736 | UP |
| C5orf24 | FLJ37562 | BC053677 | E1A | | | | | 1.97 | 0.003 | | | UP |
| G3BP2 | G3BP2 | NM_203505 | E1A | | | 0.99 | 0.839 | 1.39 | 0.016 | | | UP |
| HAT1 | HAT1 | AK127840 | E1A | | | | | 1.79 | 0.023 | | | UP |
| LBR | LBR | NM_002296 | E1A | | | | | 1.36 | 0.143 | | | UP |
| MCM4* | MCM4 | NM_005914 | E1A | 1.36 | 0.153 | 1.10 | 0.562 | 2.63 | 0.008 | 1.51 | 0.317 | UP |
| MCM6* | MCM6 | NM_005915 | E1A | | | 1.44 | 0.001 | 1.45 | 0.058 | 2.07 | 0.022 | UP |
| MCM7* | MCM7 | NM_182776 | E1A | | | 1.39 | 0.008 | 1.93 | 0.007 | 1.62 | 0.138 | UP |
| NASP | NASP | AY700118 | E1A | 0.96 | 0.724 | 1.12 | 0.296 | 1.37 | 0.073 | 1.19 | 0.071 | UP |
| NUDCD1* | CML66 | BC043406 | E1A | | | | | 1.36 | 0.082 | 1.88 | 0.001 | UP |
| KLHL23 | MGC226792 | BC010437 | E1A | | | | | 1.37 | 0.093 | | | UP |
| PTBP2 | PTBP2 | AB209266 | E1A | | | | | 0.9 | 0.521 | | | UP |
| RRM2* | RRM2 | AK123010 | E1A | 1.38 | 0.151 | 0.93 | 0.812 | 2.13 | 0.003 | 5.29 | 0.049 | UP |
| SCC-112 | KIAA0648 | BC114218 | E1A | | | | | 1.28 | 0.043 | | | UP |
| SF3B1* | SF3B1 | NM_012433 | E1A | | | 1.04 | 0.705 | 1.26 | 0.017 | 1.14 | 0.033 | UP |
| SMU1 | SMU1 | NM_018225 | E1A | | | | | 1.23 | 0.309 | 1.25 | 0.863 | UP |
| SYNCRIP | SYNCRIP | AB209098 | E1A | | | | | 1.33 | 0.035 | | | UP |
| TAF3 | TAF3 | XM_291729 | E1A | | | | | 0.74 | 0.224 | | | UP |
| TRPC4AP | TRPC4AP | AL096738 | E1A | | | 0.98 | 0.938 | 1.25 | 0.028 | 1.08 | 0.194 | UP |
| UHRF1 | UHRF1 | AB177623 | E1A | | | | | 1.95 | 0.022 | | | UP |
| USP37 | KIAA1S94 | BX538024 | E1A | | | | | 1.72 | 0.001 | | | UP |
| ARL4A | ARL4A | NM_005738 | Meta. | 0.78 | 0.108 | 1.38 | 0.001 | 2.16 | 0.002 | | | UP |
| ATP13A3 | ATP13A3 | AJ306929 | Meta. | 1.23 | 0.236 | 1.40 | 0.003 | 1.37 | 0.067 | 1.12 | 0.164 | UP |
| BCAM | LU | BC050450 | Meta. | 0.51 | <0.001 | 0.62 | 0.007 | 1.22 | 0.288 | 0.81 | 0.316 | DOWN |
| †BFSP1 | †BFSP1 | AF039655 | Meta. | 1.04 | 0.860 | 1.52 | 0.071 | 1.27 | 0.378 | 1.05 | 0.78 | UP |
| †CTF1 | †CTF1 | BC036787 | Meta. | 0.71 | 0.055 | 0.87 | 0.121 | 1.45 | 0.093 | 0.75 | 0.663 | DOWN |
| CXCL6* | CXCL6 | U81234 | Meta. | 1.07 | 0.771 | 2.56 | 0.210 | 1.26 | 0.332 | 2.88 | 0.424 | UP |
| GINS1 | KIAA0186 | NM_021067 | Meta. | 0.93 | 0.716 | 2.28 | 0.001 | 0.82 | 0.445 | 1.36 | 0.234 | UP |
| E2F4* | E2F4 | NM_001950 | Meta. | 1.07 | 0.640 | 1.05 | 0.418 | 1.05 | 0.335 | 1.24 | 0.032 | UP |
| †FGF4 | †FGF4 | NM_002007 | Meta. | 1.22 | 0.344 | 1.37 | 0.005 | 0.68 | 0.258 | ND | ND | UP |
| †FLJ16124 | †FLJ16124 | AK131224 | Meta. | | | 0.76 | 0.001 | 0.8 | 0.275 | | | DOWN |
| †FUCA1 | †FUCA1 | NM_000147 | Meta. | 0.78 | 0.057 | 0.80 | 0.095 | 1.29 | 0.166 | 0.95 | 0.861 | DOWN |
| GABPB2* | GABPB2 | NM_005254 | Meta. | 0.80 | 0.197 | 0.92 | 0.255 | 0.79 | 0.075 | 1.57 | 0.046 | UP |
| GNS | GNS | NM_002076 | Meta. | 0.85 | 0.005 | 1.50 | 0.165 | 1.55 | 0.014 | 0.86 | 0.739 | DOWN |
| GAPDH | GAPDH | BF983396 | Meta. | 1.34 | 0.024 | 1.19 | 0.009 | 1.85 | 0.002 | 1.32 | 0.597 | UP |
| GARS | GARS | NM_002047 | Meta. | 1.01 | 0.925 | 1.37 | 0.001 | 1.38 | 0.003 | 1.47 | 0.13 | UP |
| †GAP43 | †GAP43 | AK091466 | Meta. | 1.04 | 0.186 | 1.35 | 0.250 | 0.87 | 0.175 | ND | ND | UP |
| †H2AFZ | †H2AFZ | AK056803 | Meta. | 1.23 | 0.149 | 1.35 | 0.005 | 1.52 | 0.065 | | | UP |
| HSPD1 | HSPD1 | NM_002156 | Meta. | 1.15 | 0.305 | 1.35 | 0.005 | 2.26 | <0.001 | | | UP |
| †HUWE1 | †HUWE1 | DQ097177 | Meta. | 1.00 | 0.983 | 1.02 | 0.791 | 1.35 | <0.001 | | | UP |
| HSPG2* | HSPG2 | M85289 | Meta. | 1.08 | 0.715 | 0.95 | 0.712 | 2.41 | 0.001 | 1.44 | 0.016 | UP |
| HOXB7* | HOXB7 | AK223249 | Meta. | 0.78 | 0.456 | 1.31 | 0.026 | 1.55 | 0.117 | 2.93 | 0.016 | UP |
| †HPRT1 | †HPRT1 | NM_000194 | Meta. | 1.03 | 0.811 | 1.35 | 0.008 | 1.46 | 0.045 | 1 | 0.736 | UP |
| †IRF2 | †IRF2 | BX648934 | Meta. | 0.81 | 0.209 | 0.90 | 0.152 | 0.74 | 0.246 | 1.07 | 0.803 | DOWN |
| †KRT6B | †KRT6B | BC110639 | Meta. | 1.25 | 0.488 | | | 0.7 | 0.365 | | | DOWN |
| †KIAA1128 | †KIAA1128 | NM_018999 | Meta. | 0.96 | 0.722 | 0.76 | 0.012 | 1.2 | 0.158 | 1.04 | 0.47 | DOWN |
| HLA-DQB1* | HLA-DQB1 | AB209580 | Meta. | 0.38 | 0.010 | 0.48 | 0.039 | 0.39 | 0.001 | 0.59 | 0.191 | DOWN |
| †3.8-1 | †3.8-1 | L29376 | Meta. | 0.70 | 0.131 | 1.02 | 0.918 | 0.82 | 0.269 | | | DOWN |
| †MAPRE2 | †MAPRE2 | BC007318 | Meta. | 0.89 | 0.370 | 0.86 | 0.197 | 1.72 | 0.189 | 0.86 | 0.723 | DOWN |
| †MYOM2 | †MYOM2 | BC052969 | Meta. | 1.05 | 0.842 | 1.45 | 0.183 | 0.69 | 0.269 | ND | ND | UP |
| †MYH10 | †MYH10 | AB210026 | Meta. | 0.77 | 0.055 | 0.92 | 0.591 | 0.8 | 0.326 | | | DOWN |
| †PGAM1 | †PGAM1 | BM542237 | Meta. | 1.13 | 0.251 | 1.35 | 0.005 | 1.57 | 0.227 | | | UP |
| PAICS | PAICS | NM_006452 | Meta. | 1.04 | 0.826 | 1.71 | 0.002 | 1.36 | 0.082 | 1.04 | 0.638 | UP |
| POLR2C | POLR2C | NM_032940 | Meta. | 0.73 | 0.043 | 1.09 | 0.396 | 1.37 | 0.093 | 1.03 | 0.495 | DOWN |
| †KCNJ12 | †KCNJ12 | NM_021012 | Meta. | 0.78 | 0.370 | 1.25 | 0.221 | 0.76 | 0.375 | 0.88 | 0.226 | DOWN |
| †KCNA5 | †KCNA5 | M55513 | Meta. | 1.11 | 0.744 | 1.01 | 0.895 | 1.25 | 0.368 | 1.18 | 0.875 | UP |
| PBXIP1 | PBXIP1 | NM_020524 | Meta. | 0.85 | 0.302 | 0.74 | 0.001 | 1.32 | 0.197 | 0.87 | 0.897 | DOWN |
| PFN2 | PFN2 | BC043646 | Meta. | 1.33 | 0.368 | 1.75 | 0.037 | 1.98 | 0.037 | 1.38 | 0.734 | UP |
| RFTN1* | RAFTLIN | NM_015150 | Meta. | 0.61 | <0.001 | 0.83 | 0.085 | 1.52 | <0.001 | 1.68 | 0.744 | DOWN |
| †SEPW1 | †SEPW1 | BF341549 | Meta. | 0.86 | 0.168 | 0.78 | 0.016 | 1.33 | 0.039 | 1.34 | 0.434 | DOWN |
| SERPINB5* | SERPINB5 | BX640597 | Meta. | 4.05 | 0.001 | 1.47 | 0.067 | 3.05 | 0.122 | 3.22 | 0.01 | UP |

TABLE 8-continued

Analysis of the 80-gene model in the, Michigan, Harvard and Duke cohort and in the IFOM training cohort.

| Symbol | Gene | Acc | Source | MICH. cohort FOLD RATIO | MICH. cohort p-value | HARV. cohort FOLD RATIO | HARV. cohort p-value | DUKE cohort FOLD | DUKE cohort p-value | IFOM cohort FOLD RATIO | IFOM cohort p-value | TREND |
|---|---|---|---|---|---|---|---|---|---|---|---|---|
| †SIAH1 | †SIAH1 | BX647064 | Meta. | 1.26 | 0.192 | 1.07 | 0.336 | 1.36 | 0.006 | | | UP |
| †ST8SIA1 | †ST8SIA1 | NM_003034 | Meta. | 0.83 | 0.233 | 0.65 | 0.010 | 0.97 | 0.927 | 1.07 | 0.876 | DOWN |
| †TDGF1 | †TDGF1 | NM_003212 | Meta. | 0.89 | 0.541 | 0.88 | 0.514 | 1.75 | 0.100 | | | UP |
| †TMSB4X | †TMSB4X | BF680512 | Meta. | 0.80 | 0.023 | 0.93 | 0.345 | 1.03 | 0.696 | | | DOWN |
| †TLE2 | †TLE2 | NM_003260 | Meta. | 0.60 | 0.058 | 0.89 | 0.179 | 1.31 | 0.25 | 0.81 | 0.692 | DOWN |
| †VIP | †VIP | NM_003381 | Meta. | 1.30 | 0.149 | 0.85 | 0.072 | 0.91 | 0.77 | ND | ND | DOWN |
| †CRK | †CRK | BC008506 | Meta. | 1.15 | 0.400 | 0.79 | 0.105 | 1.68 | 0.063 | 1.2 | 0.799 | UP |
| †ZMAT2 | †ZMAT2 | AK055683 | Meta. | 0.83 | 0.505 | | | 1.52 | 0.001 | 1.05 | 0.76 | UP |
| †U60269 | †U60269 | U60269 | Meta. | 1.05 | 0.661 | 0.54 | 0.001 | NO | NO | | | DOWN |

Table 8a

| Symbol | Gene | Acc | Source | MICH. FOLD RATIO | MICH. p-value | HARV. FOLD RATIO | HARV. p-value | DUKE FOLD | DUKE p-value | IFOM FOLD RATIO | IFOM p-value | TREND |
|---|---|---|---|---|---|---|---|---|---|---|---|---|
| BAT1 | BAT1 | AK127767 | E1A | | | | | 1.26 | 0.085 | | | UP |
| CLDND1 | C3orf4 | BX647535 | E1A | | | | | 0.73 | 0.035 | | | UP |
| CCNE1 | CCNE1 | BC035498 | E1A | | | | | 1.24 | 0.432 | 0.94 | 0.84 | UP |
| CCNE2 | CCNE2 | NM_057749 | E1A | | | 1.22 | 0.364 | 1.13 | 0.59 | 0.78 | 0.543 | UP |
| CKAP5 | ch-TOG | NM_001008938 | E1A | | | | | 1.44 | 0.037 | 1.03 | 0.988 | UP |
| DEPDC1B | XTP1 | BC019075 | E1A | | | | | 0.74 | 0.173 | | | UP |
| E2F1 | E2F1 | BC050369 | E1A | 1.01 | 0.949 | 1.12 | 0.060 | 1.17 | 0.288 | 1.79 | 0.012 | UP |
| FAM91A1 | FLJ23790/SKIN | AL832999 | E1A | | | | | 1.43 | 0.019 | 1.13 | 0.736 | UP |
| C5orf24 | FLJ37562 | BC053677 | E1A | | | | | 1.97 | 0.003 | | | UP |
| G3BP2 | G3BP2 | NM_203505 | E1A | | | 0.99 | 0.839 | 1.39 | 0.016 | | | UP |
| HAT1 | HAT1 | AK127840 | E1A | | | | | 1.79 | 0.023 | | | UP |
| LBR | LBR | NM_002296 | E1A | | | | | 1.36 | 0.143 | | | UP |
| MCM4 | MCM4 | NM_005914 | E1A | 1.36 | 0.153 | 1.10 | 0.562 | 2.63 | 0.008 | 1.51 | 0.317 | UP |
| MCM6 | MCM6 | NM_005915 | E1A | | | 1.44 | 0.001 | 1.45 | 0.058 | 2.07 | 0.022 | UP |
| MCM7 | MCM7 | NM_182776 | E1A | | | 1.39 | 0.008 | 1.93 | 0.007 | 1.62 | 0.138 | UP |
| NASP | NASP | AY700118 | E1A | 0.96 | 0.724 | 1.12 | 0.296 | 1.37 | 0.073 | 1.19 | 0.071 | UP |
| NUDCD1 | CML66 | BC043406 | E1A | | | | | 1.36 | 0.082 | 1.88 | 0.001 | UP |
| KLHL23 | MGC226792 | BC010437 | E1A | | | | | 1.37 | 0.093 | | | UP |
| PTBP2 | PTBP2 | AB209266 | E1A | | | | | 0.9 | 0.521 | | | UP |
| RRM2 | RRM2 | AK123010 | E1A | 1.38 | 0.151 | 0.93 | 0.812 | 2.13 | 0.003 | 5.29 | 0.049 | UP |
| SCC-112 | KIAA0648 | BC114218 | E1A | | | | | 1.28 | 0.043 | | | UP |
| SF3B1 | SF3B1 | NM_012433 | E1A | | | 1.04 | 0.705 | 1.26 | 0.017 | 1.14 | 0.033 | UP |
| SMU1 | SMU1 | NM_018225 | E1A | | | | | 1.23 | 0.309 | 1.25 | 0.863 | UP |
| SYNCRIP | SYNCRIP | AB209098 | E1A | | | | | 1.33 | 0.035 | | | UP |
| TAF3 | TAF3 | XM_291729 | E1A | | | | | 0.74 | 0.224 | | | UP |
| TRPC4AP | TRPC4AP | AL096738 | E1A | | | 0.98 | 0.938 | 1.25 | 0.028 | 1.08 | 0.194 | UP |
| UHRF1 | UHRF1 | AB177623 | E1A | | | | | 1.95 | 0.022 | | | UP |
| USP37 | KIAA1594 | BX538024 | E1A | | | | | 1.72 | 0.001 | | | UP |

Table 8b

| Symbol | Gene | Acc | Source | MICH. FOLD RATIO | MICH. p-value | HARV. FOLD RATIO | HARV. p-value | DUKE FOLD | DUKE p-value | IFOM FOLD RATIO | IFOM p-value | TREND |
|---|---|---|---|---|---|---|---|---|---|---|---|---|
| ARL4A | ARL4A | NM_005738 | Meta. | 0.78 | 0.108 | 1.38 | 0.001 | 2.16 | 0.002 | | | UP |
| ATP13A3 | ATP13A3 | AJ306929 | Meta. | 1.23 | 0.236 | 1.40 | 0.003 | 1.37 | 0.067 | 1.12 | 0.164 | UP |
| BCAM | LU | BC050450 | Meta. | 0.51 | <0.001 | 0.62 | 0.007 | 1.22 | 0.288 | 0.81 | 0.316 | DOWN |
| †BFSP1 | †BFSP1 | AF039655 | Meta. | 1.04 | 0.860 | 1.52 | 0.071 | 1.27 | 0.378 | 1.05 | 0.78 | UP |
| †CTF1 | †CTF1 | BC036787 | Meta. | 0.71 | 0.055 | 0.87 | 0.121 | 1.45 | 0.093 | 0.75 | 0.663 | DOWN |
| CXCL6 | CXCL6 | U81234 | Meta. | 1.07 | 0.771 | 2.56 | 0.210 | 1.26 | 0.332 | 2.88 | 0.424 | UP |
| GINS1 | KIAA0186 | NM_021067 | Meta. | 0.93 | 0.716 | 2.28 | 0.001 | 0.82 | 0.445 | 1.36 | 0.234 | UP |
| E2F4 | E2F4 | NM_001950 | Meta. | 1.07 | 0.640 | 1.05 | 0.418 | 1.05 | 0.335 | 1.24 | 0.032 | UP |
| †FGF4 | †FGF4 | NM_002007 | Meta. | 1.22 | 0.344 | 1.37 | 0.005 | 0.68 | 0.258 | ND | ND | UP |
| †FLJ16124 | †FLJ16124 | AK131224 | Meta. | | | 0.76 | 0.001 | 0.8 | 0.275 | | | DOWN |
| †FUCA1 | †FUCA1 | NM_000147 | Meta. | 0.78 | 0.057 | 0.80 | 0.095 | 1.29 | 0.166 | 0.95 | 0.861 | DOWN |
| GABPB2 | GABPB2 | NM_005254 | Meta. | 0.80 | 0.197 | 0.92 | 0.255 | 0.79 | 0.075 | 1.57 | 0.046 | UP |
| GNS | GNS | NM_002076 | Meta. | 0.85 | 0.005 | 1.50 | 0.165 | 1.55 | 0.014 | 0.86 | 0.739 | DOWN |
| GAPDH | GAPDH | BF983396 | Meta. | 1.34 | 0.024 | 1.19 | 0.009 | 1.85 | 0.002 | 1.32 | 0.597 | UP |
| GARS | GARS | NM_002047 | Meta. | 1.01 | 0.925 | 1.37 | 0.001 | 1.38 | 0.003 | 1.47 | 0.13 | UP |
| †GAP43 | †GAP43 | AK091466 | Meta. | 1.04 | 0.186 | 1.35 | 0.250 | 0.87 | 0.175 | ND | ND | UP |
| †H2AFZ | †H2AFZ | AK056803 | Meta. | 1.23 | 0.149 | 1.35 | 0.005 | 1.52 | 0.065 | | | UP |
| HSPD1 | HSPD1 | NM_002156 | Meta. | 1.15 | 0.305 | 1.35 | 0.005 | 2.26 | <0.001 | | | UP |
| †HUWE1 | †HUWE1 | DQ097177 | Meta. | 1.00 | 0.983 | 1.02 | 0.791 | 1.35 | <0.001 | | | UP |
| HSPG2 | HSPG2 | M85289 | Meta. | 1.08 | 0.715 | 0.95 | 0.712 | 2.41 | 0.001 | 1.44 | 0.016 | UP |
| HOXB7 | HOXB7 | AK223249 | Meta. | 0.78 | 0.456 | 1.31 | 0.026 | 1.55 | 0.117 | 2.93 | 0.016 | UP |
| †HPRT1 | †HPRT1 | NM_000194 | Meta. | 1.03 | 0.811 | 1.35 | 0.008 | 1.46 | 0.045 | 1 | 0.736 | UP |
| †IRF2 | †IRF2 | BX648934 | Meta. | 0.81 | 0.209 | 0.90 | 0.152 | 0.74 | 0.246 | 1.07 | 0.803 | DOWN |
| †KRT6B | †KRT6B | BC110639 | Meta. | 1.25 | 0.488 | | | 0.7 | 0.365 | | | DOWN |
| †KIAA1128 | †KIAA1128 | NM_018999 | Meta. | 0.96 | 0.722 | 0.76 | 0.012 | 1.2 | 0.158 | 1.04 | 0.47 | DOWN |
| HLA-DQB1 | HLA-DQB1 | AB209580 | Meta. | 0.38 | 0.010 | 0.48 | 0.039 | 0.39 | 0.001 | 0.59 | 0.191 | DOWN |
| †3.8-1 | †3.8-1 | L29376 | Meta. | 0.70 | 0.131 | 1.02 | 0.918 | 0.82 | 0.269 | | | DOWN |
| †MAPRE2 | †MAPRE2 | BC007318 | Meta. | 0.89 | 0.370 | 0.86 | 0.197 | 1.72 | 0.189 | 0.86 | 0.723 | DOWN |
| †MYOM2 | †MYOM2 | BC052969 | Meta. | 1.05 | 0.842 | 1.45 | 0.183 | 0.69 | 0.269 | ND | ND | UP |
| †MYH10 | †MYH10 | AB210026 | Meta. | 0.77 | 0.055 | 0.92 | 0.591 | 0.8 | 0.326 | | | DOWN |
| †PGAM1 | †PGAM1 | BM542237 | Meta. | 1.13 | 0.251 | 1.25 | 0.005 | 1.57 | 0.227 | | | UP |

TABLE 8-continued

Analysis of the 80-gene model in the, Michigan, Harvard and Duke cohort and in the IFOM training cohort.

| | | | | MICH. cohort | | HARV. cohort | | DUKE cohort | | IFOM cohort | | |
|---|---|---|---|---|---|---|---|---|---|---|---|---|
| Symbol | Gene | Acc | Source | FOLD RATIO | p-value | FOLD RATIO | p-value | FOLD | p-value | FOLD RATIO | p-value | TREND |
| PAICS | PAICS | NM_006452 | Meta. | 1.04 | 0.826 | 1.71 | 0.002 | 1.36 | 0.082 | 1.04 | 0.638 | UP |
| POLR2C | POLR2C | NM_032940 | Meta. | 0.73 | 0.043 | 1.09 | 0.396 | 1.37 | 0.093 | 1.03 | 0.495 | DOWN |
| †KCNJ12 | †KCNJ12 | NM_021012 | Meta. | 0.78 | 0.370 | 1.25 | 0.221 | 0.76 | 0.375 | 0.88 | 0.226 | DOWN |
| †KCNA5 | †KCNA5 | M55513 | Meta. | 1.11 | 0.744 | 1.01 | 0.895 | 1.25 | 0.368 | 1.18 | 0.875 | UP |
| PBXIP1 | PBXIP1 | NM_020524 | Meta. | 0.85 | 0.302 | 0.74 | 0.001 | 1.32 | 0.197 | 0.87 | 0.897 | DOWN |
| PFN2 | PFN2 | BC043646 | Meta. | 1.33 | 0.368 | 1.75 | 0.037 | 1.98 | 0.037 | 1.38 | 0.734 | UP |
| RFTN1 | RAFTLIN | NM_015150 | Meta. | 0.61 | <0.001 | 0.83 | 0.085 | 1.52 | <0.001 | 1.68 | 0.744 | DOWN |
| †SEPW1 | †SEPW1 | BF341549 | Meta. | 0.86 | 0.168 | 0.78 | 0.016 | 1.33 | 0.039 | 1.34 | 0.434 | DOWN |
| SERPINB5 | SERPINB5 | BX640597 | Meta. | 4.05 | 0.001 | 1.47 | 0.067 | 3.05 | 0.122 | 3.22 | 0.01 | UP |
| †SIAH1 | †SIAH1 | BX647064 | Meta. | 1.26 | 0.192 | 1.07 | 0.336 | 1.36 | 0.006 | | | UP |
| †ST8SIA1 | †ST8SIA1 | NM_003034 | Meta. | 0.83 | 0.233 | 0.65 | 0.010 | 0.97 | 0.927 | 1.07 | 0.876 | DOWN |
| †TDGF1 | †TDGF1 | NM_003212 | Meta. | 0.89 | 0.541 | 0.88 | 0.514 | 1.75 | 0.100 | | | UP |
| †TMSB4X | †TMSB4X | BF680512 | Meta. | 0.80 | 0.023 | 0.93 | 0.345 | 1.03 | 0.696 | | | DOWN |
| †TLE2 | †TLE2 | NM_003260 | Meta. | 0.60 | 0.058 | 0.89 | 0.179 | 1.31 | 0.25 | 0.81 | 0.692 | DOWN |
| †VIP | †VIP | NM_003381 | Meta. | 1.30 | 0.149 | 0.85 | 0.072 | 0.91 | 0.77 | ND | ND | DOWN |
| †CRK | †CRK | BC008506 | Meta. | 1.15 | 0.400 | 0.79 | 0.105 | 1.68 | 0.063 | 1.2 | 0.799 | UP |
| †ZMAT2 | †ZMAT2 | AK055683 | Meta. | 0.83 | 0.505 | | | 1.52 | 0.001 | 1.05 | 0.76 | UP |
| †U60269 | †U60269 | U60269 | Meta. | 1.05 | 0.661 | 0.54 | 0.001 | NO | NO | | | DOWN |

Table 8. Analysis of the 80-gene model in the Michigan, Harvard, Duke cohort and in the IFOM training cohort.
Legend to Table 8.
The genes of the 80-gene model are shown with their human gene symbol, name, human accession number and source (Liter., from literature; E1A, from the 28-gene biased signature; Meta., from meta-analysis of the reduced Michigan and Harvard datasets).
Table 8a simply separates out the genes having an E1A source;
Table 8b simply separates out the genes having a meta-analysis source.

Analysis in the Michigan, Harvard and Duke cohorts was performed on the available microarray datasets by selecting stage I NSCLC (67, 62 and 34 patients, respectively); in the IFOM training cohort, the analysis was performed by Real Time PCR (Q-PCR, see above for details). Fold ratio indicates the average fold mRNA increase (>1.0) or decrease (<1.0) in the bad prognosis group, compared to the good prognosis group (followed by its p-value). Asterisks indicate the 16 genes selected to develop the final prognostic model. ND, not detectable. NO, No probeset corresponding to the hypothetical U60269 gene was present on the HU133 2.0 plus chip used in the Duke analysis.

The column 'TREND' indicates the assigned regulation trend of each gene transcript in the poor prognosis group compared to the good prognosis group, based on the dominant trend, and is intended to provide an indication as to how these genes may be associated with worsening of prognosis. All the 28 E1A genes are considered to be up regulated in the poor prognosis class, based on the results of our previous E1A screening.

The major goal of our efforts was to identify a small number of genes, amenable to analysis with a readily available technology (such as Real Time PCR), which can constitute a prognostic model that can be rapidly transferred to the clinical laboratory. Thus, we used TaqMan® Low Density Arrays to profile a set of 25 patients with stage I lung adenocarcinomas (henceforth "the IFOM training cohort", see Methods). At the time of our analysis, TaqMan® Low Density Arrays were available for 53 of the 80 genes (see Table 8). The profiling results obtained using the IFOM training cohort are summarized in Table 8. From these results, we excluded a number of genes that did not show variability between the good and bad prognosis groups, and we then selected 16 genes for further analysis (p≤0.05 or fold change greater than ±1.5 range, as cutoff, Table 8).

The final prognostic model was obtained by the leave-one-out cross-validation procedure, with independent gene selection (p<0.05 as cutoff; parametric t-test). We found that a 10-gene model displayed a predictive accuracy of 84% (sensitivity, 90%; specificity, 80%) and a p-value of 0.004, after 2000 random permutations of class labels (Table 9).

TABLE 9

| Symbol | Gene | Acc | t-value | FOLD RATIO | p-value |
|---|---|---|---|---|---|
| NUDCD1 | CML66 | BC043406 | −3.95 | 1.80 | <0.001 |
| E2F1 | E2F1 | BC050369 | −2.63 | 1.78 | 0.016 |
| HOXB7 | HOXB7 | AK223249 | −2.59 | 2.53 | 0.017 |
| MCM6 | MCM6 | NM_005915 | −2.57 | 1.80 | 0.019 |
| SERPINB5 | SERPINB5 | BX640597 | −2.53 | 3.95 | 0.019 |
| E2F4 | E2F4 | NM_001950 | −2.51 | 1.37 | 0.019 |
| HSPG2 | HSPG2 | M85289 | −2.38 | 1.58 | 0.026 |
| SF3B1 | SF3B1 | NM_012433 | −2.32 | 1.24 | 0.029 |
| RRM2 | RRM2 | AK123010 | −2.16 | 2.56 | 0.041 |
| SCGB3A1 | SCGB3A1 | BM921624 | 5.54 | 0.01 | <0.001 |

Table 9: Final prognostic model obtained by the leave-one-out cross-validation procedure of the IFOM training cohort.

The genes of the 10-gene model are shown with their human gene symbol, name and accession number and sorted by the t-values derived from the parametric t-test. Fold ratio indicates the average mRNA fold increase (>1.0) or decrease (<1.0) in the bad prognosis group, compared to the good prognosis group (followed by its p-value).

Upregulation of all genes other than SCGB3A1, and downregulation of SCGB3A1 (e.g., upregulation or downregulation of mRNA respectively), may be associated with a worsening of the prognosis.

To confirm the robustness of this new prognostic model, we used it on an additional, independent cohort of 45 stage-I lung adenocarcinomas (henceforth "the IFOM validation cohort", see Methods). Univariate and multivariate analysis showed that the 10-gene model predicted survival of patients more accurately than tumor size, grading, age, sex or presence of mutated KRAS (Table 10).

TABLE 10

Univariate and multivariate analysis of various prognostic markers.

| Variable | Subset | IFOM Validation cohort (N = 45) | | IFOM Training + Validation Cohorts (N = 70) | | IFOM mutational analysis cases (N = 39) | |
|---|---|---|---|---|---|---|---|
| | | OD (95% CI) | P | OD (95% CI) | P | OD (95% CI) | P |
| Univariate analysis | | | | | | | |
| Age | ≥64/<64 | 0.96 (0.29-3.16) | 0.946 | 0.33 (0.24-1.61) | 0.336 | | |
| Differentiation | well + moderate/ poor | 0.64 (0.14-2.54) | 0.534 | 0.78 (0.29-2.07) | 0.621 | | |
| Size | ≤30 mm/>30 mm | 0.44 (0.10-1.66) | 0.234 | 1.14 (0.41-3.23) | 0.794 | | |
| KRAS | mut/wt | | | | | 2.00 (0.49-8.24) | 0.327 |
| 10-gene model | poor/good | 3.94 (1.17-14.4) | *0.026 | 7.22 (2.60-21.7) | *0.0002 | 4.00 (1.06-16.89) | *0.041 |
| Multivariate analysis | | | | | | | |
| Age | ≥64/<64 | 1.00 (0.26-3.90) | 0.995 | 0.51 (0.16-1.50) | 0.232 | | |
| Differentiation | well + moderate/ poor | 0.65 (0.13-2.92) | 0.584 | 0.79 (0.24-2.40) | 0.679 | | |
| Size | ≤30 mm/>30 mm | 0.38 (0.08-1.68) | 0.222 | 0.94 (0.28-3.05) | 0.922 | | |
| KRAS | mut/wt | | | | | 9.07 (1.27-187.9) | 0.058 |
| 10-gene model | poor/good | 3.98 (1.13-15.5) | *0.036 | 7.78 (2.72-24.8) | *0.0002 | 13.19 (2.06-261.4) | *0.021 |

Table 10. The 10-gene model was tested for prediction of survival in the indicated cohorts of patients, in comparison to other biological or biochemical parameters, in univariate and multivariate analysis.
Data are expressed as odds ratio (OD) at 95% confidence interval (95% CI). Asterisks indicate statistically significant values.
The "IFOM mutational analysis cases" include 39 cases from a total of 70 (of the IFOM training and validation cohorts combined) for which mutational analysis of the KRAS gene was available.

Figure 12A:
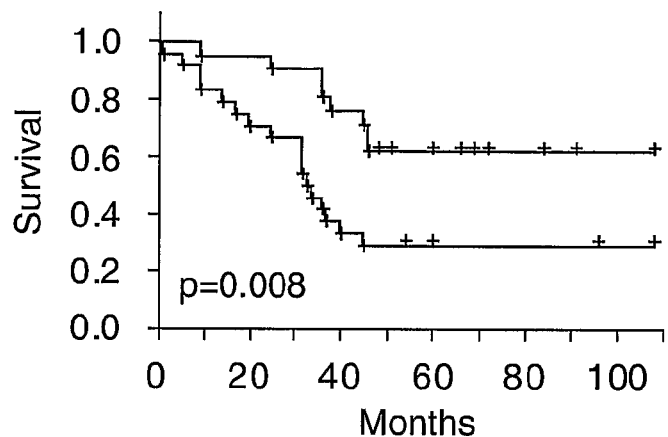
Figure 12A:
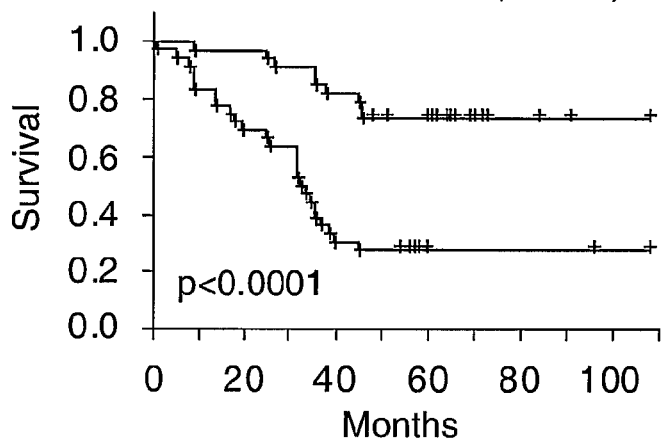
Figure 12A:
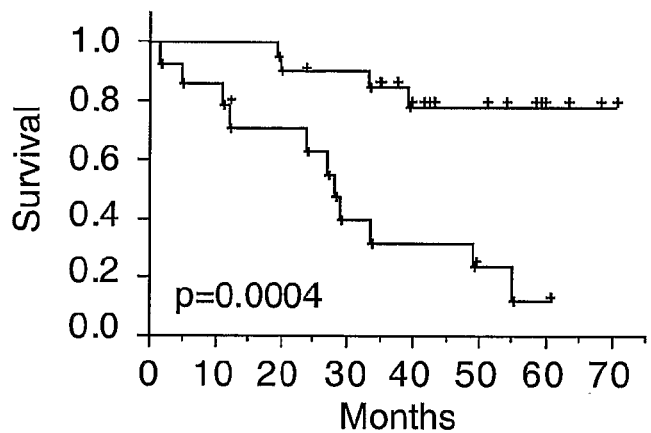

Kaplan-Meier survival curves showed a significant difference in the survival rate of patients stratified according to the 10-gene prognostic model (p=0.008; log-rank test) (FIG. 12A). It is also of note that, although our 10-gene model included only 4 genes derived from meta-analysis of expression profiles, it showed very good predictive power in Kaplan-Meyer analysis of the Duke cohort, for which expression data for all 10 genes were available (FIG. 12A; see also FIG. 14).

In this example, a poor prognosis patient was considered as one having 3 or more genes following the poor prognosis pattern, namely:
  upregulated in the poor prognosis compared to the good prognosis group for all genes except for SCGB3A1;
  downregulated in the poor prognosis group compared to the good prognosis group in the case of SCGB3A1.

Of course, depending on the purpose, patients could be considered "poor prognosis" having a different number of genes following the poor prognosis pattern. E.g., patients having 2 or more, or 4 or 5 or more genes following the "poor prognosis" pattern could be placed in the poor prognosis class.

Figure 12B:
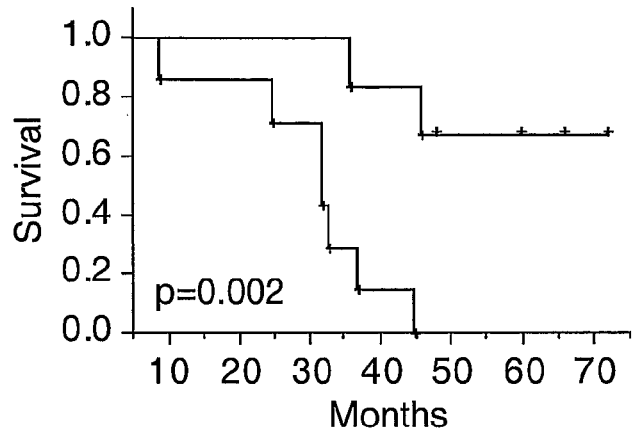
Figure 12B:
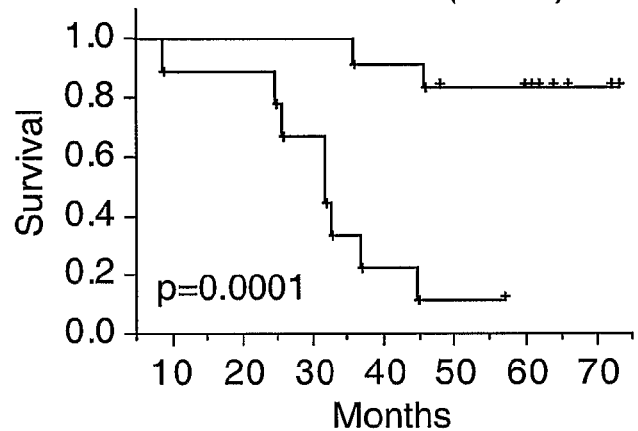
Figure 12B:
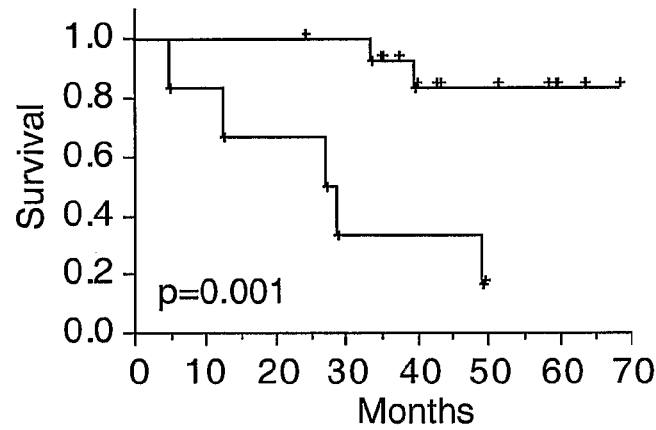

We also tested whether our 10-gene model had predictive power in stage IA lung adenocarcinoma. The 5-year survival rate of clinical stage IA lung cancer patients ranges from 67% to 77% (28-30) after surgery alone. Thus, in this group, molecular tools for patient stratification are greatly needed, to select high-risk patients eligible for adjuvant chemotherapy. As shown in FIG. 12B, our 10-gene model displayed very good predictive power both in the IFOM and in the Duke (stage IA) cohorts.

Moreover, the inventors measured performance of the 10-genes model compared to the 21-genes set of table 3.

The prognostic predictive accuracies of the 10-genes model, the 21-genes model and the 11-genes model (obtained after subtracting the 10 genes of the 10-genes model from the 21-genes set) on the training cohort (25 patients), testing cohort (45 patients) and the entire data set (70 patients, training+testing cohorts) were measured.

In the 'Training Cohort' the definition of the classifier was performed by applying diagonal linear discriminant analysis (DLDA) and leave-one-out cross-validation. In the 'Test Cohort' prediction of prognosis was performed by applying the diagonal linear discriminant analysis (DLDA) classification method using the gene expression values of the training cohort to train the classifier. The results are shown below. Remarkably, it can be seen that the reduced, ten gene dataset performs better than the 21 gene dataset despite containing fewer genes.

| Model | Acc. (%) | Sens. (%) | Spec. (%) |
|---|---|---|---|
| Training Cohort (25 patients) | | | |
| 10-gene | 84 | 90 | 80 |
| 21-gene | 76 | 90 | 67 |
| 11-gene | 64 | 50 | 73 |
| Testing Cohort (45 patients) | | | |
| 10-gene | 67 | 68 | 65 |
| 21-gene | 64 | 64 | 65 |
| 11-gene | 60 | 56 | 65 |

-continued

| Model | Acc. (%) | Sens. (%) | Spec. (%) |
|---|---|---|---|
| Training + Testing Cohort (70 patients) | | | |
| 10-gene | 73 | 74 | 71 |
| 21-gene | 69 | 71 | 66 |
| 11-gene | 60 | 54 | 69 |

Accuracy (Acc.), percentage of correctly predicted patients; sensitivity (Sen.), probability for a patient with poor prognosis to be predicted as with poor prognosis; specificity (Spec.), probability for a patient with good prognosis to be predicted as with good prognosis.

Discussion

We have identified a 10-gene signature that, by Real Time PCR technology, was remarkably effective in predicting prognosis and overall survival of patients with stage I lung adenocarcinomas.

The major difference between our approach and the widely employed, more traditional ones (Wigle, D. A., et al, 2002, *Cancer Res* 62:3005-3008, Beer et al, as above, Lu, Y., et al, 2006, *PLoS Med* 3:e467, Raponi, M., et al, 2006, *Cancer Res* 66:7466-7472, Endoh, H., et al, 2004, *J Clin Oncol* 22:811-819) consisted in merging a biased signature with those obtained by the unbiased analysis of microarray expression profiles. A biased approach to cancer transcriptomes relies on the assumption that a limited number of altered signaling pathways lead to the malignant state. Thus, molecular tools that cause transformation of cells in vitro might be used to circumvent the problems connected with unbiased transcriptome analysis, such as high individual genetic noise. We validated such an approach by showing that a signature, obtained in myotubes forced to re-enter the cell cycle by the E1A oncogene, contained genes overexpressed in human tumors that could predict unfavorable prognosis in breast cancer. We show in example 5 that the same biased signature can, by itself, predict clinical outcome in patients with stage I lung adenocarcinomas. It is of note that the genes of the 28-gene biased signature did not emerge from the analysis of lung cancer microarray datasets, either in this study or in other studies (Wigle, D. A., et al, 2002, *Cancer Res* 62:3005-3008, Beer, D. G., et al, 2002, *Nat Med* 8:816-824, Lu, Y., et al, 2006, *PLoS Med* 3:e467, Raponi, M., et al, 2006, *Cancer Res* 66:7466-7472, Endoh, H., et al, 2004, *J Clin Oncol* 22:811-819, Jiang, H., et al, 2004, *BMC Bioinformatics* 5:81, Chen, H. Y., et al, 2007, *N Engl J Med* 356:11-20) [the only exception is SYNCRIP, reported in a recent study (Potti, A., *N Engl J Med* 355:570-580)], thus confirming the power of the biased approach in revealing gene expression programs not otherwise easily identifiable. Finally, the composition of the final 10-gene prognostic model confirmed the hypothesized efficacy of our integrated approach, as it consisted of 5 genes derived from the E1A signature (NUDCD1, E2F1, MCM6, RRM2 and SF3B1), 4 genes from the metanalysis of microarray data (HOXB7, SERPINB5, E2F4 and HSPG2), and 1 gene (SCGB3A1) from the literature.

The references mentioned herein are all expressly incorporated by reference in their entirety.

The invention claimed is:

1. A method of treating a subject having stage I non-small cell carcinoma (NSCLC) comprising:
    providing an assay sample obtained from said subject;
    determining the expression level in said sample of seven or more genes selected from E2F1, RRM2, MCM6, SF3B1, NUDCD1, HOXB7, SerpinB5, E2F4, HSPG2 and SCGB3A1;
    identifying a subject as having a poor prognosis based on the expression levels of said seven or more genes, wherein E2F1, RRM2, MCM6, SF3B1, NUDCD1, HOXB7, SerpinB5, E2F4 and HSPG2 expression levels are up-regulated, and SCGB3A1 expression level is down-regulated in patients with a poor prognosis;
    and treating the subject with a poor prognosis with an adjuvant therapy selected from chemotherapy, radiotherapy, immunotherapy and hormone therapy.

2. The method of claim 1, wherein the subject has stage IA NSCLC.

3. The method of claim 1, wherein the subject has stage IB NSCLC.

4. The method of claim 1 wherein the NSCLC is an adenocarcinoma.

5. The method of claim 1, wherein the seven or more genes include the RRM2 gene.

6. The method of claim 1 wherein the seven or more genes include HOXB7, SerpinB5, E2F4, HSPG2, E2F1, MCM6 and RRM2 genes.

7. The method of claim 1 wherein the seven or more genes include E2F1, RRM2, MCM6, SF3B1, and NUDCD1 genes.

8. The method of claim 1 wherein the determining is by quantitative PCR.

9. The method of claim 1 wherein the determining comprises contacting the nucleic acids in the sample to a substrate bearing a plurality of immobilized nucleic acids.

10. The method of claim 1 wherein the determining comprises fluorescence in situ hybridization.

11. The method of claim 1, wherein the determining comprises contacting the sample with a nucleic acid which specifically hybridizes to the nucleic acid expression product of said genes.

12. The method of claim 1, wherein the determining comprises contacting the sample with nucleic acid primer pairs suitable for PCR amplification.

13. A method of treating stage I NSCLC (Non-Small Cell Lung Cancer) in a subject in need thereof, the method comprising:
    (i) providing an assay sample obtained from said subject;
    (ii) determining the expression level in said sample of seven or more genes selected from E2F1, RRM2, MCM6, SF3B1, NUDCD1, HOXB7, SerpinB5, E2F4, HSPG2 and SCGB3A1,
    (iii) identifying a subject as having a poor prognosis based on a change in the expression levels of said seven or more genes, wherein up-regulated expression levels of any of E2F1, RRM2, MCM6, SF3B1, NUDCD1, HOXB7, SerpinB5, E2F4 and HSPG2, and down-regulated expression level of SCGB3A1 occur in patients with a poor prognosis; and
    (iv) treating the subject with a poor prognosis with an adjuvant therapy.

14. The method of claim 13 wherein the detection comprises fluorescence in situ hybridization.

15. The method of claim 13 wherein the determining comprises contacting the sample with a nucleic acid which specifically hybridizes to the expression product.

16. The method of claim 13 wherein the determining comprises contacting the sample with nucleic acid primer pairs suitable for PCR amplification.

17. A method of treating stage I NSCLC (Non-Small Cell Lung Cancer) comprising administering adjuvant therapy to a subject previously assessed as having a poor NSCLC prognosis, as determined by expression of seven or more genes selected from E2F1, RRM2, MCM6, SF3B1, NUDCD1, HOXB7, SerpinB5, E2F4, HSPG2 and SCGB3A1; wherein a subject is identified as having a poor NSCLC prognosis based on a change in expression levels of said seven or more genes, wherein E2F1, RRM2, MCM6, SF3B1, NUDCD1, HOXB7, SerpinB5, E2F4 and HSPG2 expression levels are up-regulated, and SCGB3A1 expression level is down-regulated in a poor NSCLC prognosis in an assay sample obtained from said subject relative to a control.

18. The method of claim 17 wherein the measurement comprises fluorescence in situ hybridization.

19. The method of claim 17 wherein the determining comprises contacting the sample with a nucleic acid which specifically hybridizes to the expression product.

20. The method of claim 17 wherein the determining comprises contacting the sample with primer pairs suitable for PCR amplification.

* * * * *